(12) United States Patent
de los Pinos et al.

(10) Patent No.: US 12,029,794 B2
(45) Date of Patent: *Jul. 9, 2024

(54) VIRUS-LIKE PARTICLE CONJUGATES FOR DIAGNOSIS AND TREATMENT OF TUMORS

(71) Applicants: Aura Biosciences, Inc., Boston, MA (US); The United States of America, as represented by the Secretary, Department of Health and Human Serv., Bethesda, MD (US)

(72) Inventors: Elisabet de los Pinos, Brookline, MA (US); John Todd Schiller, Kensington, MD (US); Rhonda C. Kines, Washington, DC (US); John MacDougall, Hingham, MA (US)

(73) Assignees: Biosciences, Inc., Boston, MA (US); The United States of America, as represented by the Secretary, Department of Health and Human Serv., Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/540,549

(22) Filed: Dec. 2, 2021

(65) Prior Publication Data
US 2022/0088216 A1 Mar. 24, 2022

Related U.S. Application Data

(63) Continuation of application No. 17/395,369, filed on Aug. 5, 2021, which is a continuation of application
(Continued)

(51) Int. Cl.
*A61K 47/64* (2017.01)
*A61K 39/12* (2006.01)
(Continued)

(52) U.S. Cl.
CPC .......... *A61K 47/6901* (2017.08); *A61K 39/12* (2013.01); *A61K 41/0057* (2013.01);
(Continued)

(58) Field of Classification Search
CPC ...... C07K 1/13; C07K 14/025; C07K 16/084; A61K 47/64; A61K 47/6901
See application file for complete search history.

(56) References Cited

U.S. PATENT DOCUMENTS

| 4,625,014 A | 11/1986 | Senter et al. |
| 4,659,839 A | 4/1987 | Nicolotti |

(Continued)

FOREIGN PATENT DOCUMENTS

| CN | 1904012 A | 1/2007 |
| CN | 102481378 A | 5/2012 |

(Continued)

OTHER PUBLICATIONS

International Search Report and Written Opinion dated Aug. 18, 2011 for Application No. PCT/IB2010/002654.
(Continued)

Primary Examiner — Jeffrey E. Russel
(74) Attorney, Agent, or Firm — Wolf, Greenfield & Sacks, P.C.

(57) ABSTRACT

The present disclosure is directed to methods and compositions for the diagnosis and/or treatment of tumors, such as ocular tumors, using virus-like particles conjugated to photosensitive molecules.

28 Claims, 28 Drawing Sheets

Specification includes a Sequence Listing.

Related U.S. Application Data

No. 16/778,361, filed on Jan. 31, 2020, now Pat. No. 11,110,181, which is a continuation of application No. 16/143,147, filed on Sep. 26, 2018, now Pat. No. 10,588,984, which is a continuation of application No. 15/023,169, filed as application No. PCT/US2014/056412 on Sep. 18, 2014, now Pat. No. 10,117,947.

(60) Provisional application No. 61/879,627, filed on Sep. 18, 2013.

(51) Int. Cl.
| | |
|---|---|
| *A61K 41/00* | (2020.01) |
| *A61K 47/69* | (2017.01) |
| *A61N 5/06* | (2006.01) |
| *C07K 1/13* | (2006.01) |
| *C07K 14/025* | (2006.01) |
| *C07K 16/08* | (2006.01) |
| *C07K 16/32* | (2006.01) |
| *C12N 7/00* | (2006.01) |
| *A61K 39/00* | (2006.01) |

(52) U.S. Cl.
CPC .......... *A61K 41/0071* (2013.01); *A61K 47/64* (2017.08); *A61N 5/062* (2013.01); *C07K 1/13* (2013.01); *C07K 14/025* (2013.01); *C07K 16/084* (2013.01); *C07K 16/32* (2013.01); *C12N 7/00* (2013.01); *A61K 2039/545* (2013.01); *A61K 2039/585* (2013.01); *C07K 2317/33* (2013.01); *C07K 2317/76* (2013.01); *C12N 2710/20023* (2013.01); *C12N 2710/20033* (2013.01); *C12N 2710/20034* (2013.01)

(56) References Cited

U.S. PATENT DOCUMENTS

| | | | |
|---|---|---|---|
| 5,126,129 A | 6/1992 | Wiltrout et al. | |
| 5,290,551 A | 3/1994 | Berd | |
| 5,334,711 A | 8/1994 | Sproat | |
| 5,478,556 A | 12/1995 | Elliott et al. | |
| 5,667,764 A | 9/1997 | Kopia et al. | |
| 5,716,824 A | 2/1998 | Beigelman | |
| 6,022,522 A | 2/2000 | Sweet et al. | |
| 6,180,389 B1 | 1/2001 | Douglas et al. | |
| 6,416,945 B1 | 7/2002 | McCarthy et al. | |
| 6,599,720 B1 | 7/2003 | Lowy et al. | |
| 6,719,958 B1 | 4/2004 | Gozzini et al. | |
| 6,984,386 B2 | 1/2006 | Douglas et al. | |
| 6,991,795 B1 | 1/2006 | Lowe et al. | |
| 7,205,126 B2 | 4/2007 | Qiao et al. | |
| 7,351,533 B2 | 4/2008 | McCarthy et al. | |
| 7,951,379 B2 | 5/2011 | Kuroda et al. | |
| 8,394,411 B2 | 3/2013 | Roberts et al. | |
| 9,700,639 B2 | 7/2017 | de los Pinos et al. | |
| 9,724,404 B2 | 8/2017 | Coursaget et al. | |
| 9,855,347 B2 | 1/2018 | de los Pinos et al. | |
| 10,117,947 B2 | 11/2018 | de los Pinos et al. | |
| 10,179,168 B2 | 1/2019 | Coursaget et al. | |
| 10,300,150 B2 | 5/2019 | de los Pinos et al. | |
| 10,588,984 B2 | 3/2020 | de los Pinos et al. | |
| 10,596,275 B2 | 3/2020 | de los Pinos et al. | |
| 10,688,172 B2 | 6/2020 | Coursaget et al. | |
| 11,110,181 B2 | 9/2021 | de los Pinos et al. | |
| 2003/0129583 A1 | 7/2003 | Martin | |
| 2003/0206887 A1 | 11/2003 | Morrissey et al. | |
| 2004/0005338 A1 | 1/2004 | Bachmann et al. | |
| 2004/0028694 A1 | 2/2004 | Young et al. | |
| 2004/0115132 A1 | 6/2004 | Young et al. | |
| 2004/0121465 A1 | 6/2004 | Robinson | |
| 2004/0146531 A1 | 7/2004 | Antonsson et al. | |
| 2004/0152181 A1 | 8/2004 | McCarthy et al. | |
| 2005/0112141 A1 | 5/2005 | Terman | |
| 2005/0118191 A1 | 6/2005 | Robinson et al. | |
| 2005/0181064 A1 | 8/2005 | Kuroda | |
| 2006/0088536 A1 | 4/2006 | Kuroda | |
| 2006/0141042 A1 | 6/2006 | Kuroda | |
| 2006/0166913 A1 | 7/2006 | Suzuki | |
| 2006/0204444 A1 | 9/2006 | Young et al. | |
| 2006/0216238 A1 | 9/2006 | Manchester et al. | |
| 2006/0269954 A1 | 11/2006 | Lowy et al. | |
| 2007/0059245 A1 | 3/2007 | Young et al. | |
| 2007/0059746 A1 | 3/2007 | Kuroda | |
| 2007/0243157 A1 | 10/2007 | Tanaka et al. | |
| 2007/0258889 A1 | 11/2007 | Douglas et al. | |
| 2009/0012022 A1 | 1/2009 | Milner et al. | |
| 2009/0041671 A1 | 2/2009 | Young et al. | |
| 2010/0003326 A1* | 1/2010 | Vertommen | A61L 27/50 424/486 |
| 2010/0135902 A1 | 6/2010 | Roberts et al. | |
| 2011/0009601 A1* | 1/2011 | Yamauchi | C07K 16/32 530/410 |
| 2011/0052496 A1 | 3/2011 | Cid-Arregui | |
| 2011/0065173 A1 | 3/2011 | Kingsman et al. | |
| 2011/0104051 A1 | 5/2011 | Francis et al. | |
| 2012/0015899 A1 | 1/2012 | Lomonossoff et al. | |
| 2012/0171290 A1 | 7/2012 | Coursaget et al. | |
| 2012/0207840 A1 | 8/2012 | De Los Pinos | |
| 2013/0071414 A1 | 3/2013 | Dotti et al. | |
| 2013/0115247 A1 | 5/2013 | de los Pinos et al. | |
| 2013/0116408 A1 | 5/2013 | de los Pinos | |
| 2013/0136689 A1 | 5/2013 | Rohlff et al. | |
| 2013/0202645 A1 | 8/2013 | Barner et al. | |
| 2014/0306869 A1* | 10/2014 | Fujita | H10K 50/11 546/4 |
| 2014/0377170 A1 | 12/2014 | de los Pinos et al. | |
| 2015/0232880 A1 | 8/2015 | Hemminki et al. | |
| 2016/0024469 A1 | 1/2016 | Wu | |
| 2016/0228568 A1 | 8/2016 | de los Pinos et al. | |
| 2017/0274099 A1 | 9/2017 | de los Pinos et al. | |
| 2017/0368162 A1 | 12/2017 | Coursaget et al. | |
| 2018/0110883 A1 | 4/2018 | de los Pinos et al. | |
| 2018/0311269 A1 | 11/2018 | Lobb et al. | |
| 2018/0311374 A1 | 11/2018 | Lobb et al. | |
| 2019/0083647 A1 | 3/2019 | de los Pinos et al. | |
| 2019/0142925 A1 | 5/2019 | Coursaget et al. | |
| 2019/0275176 A1 | 9/2019 | de los Pinos et al. | |
| 2020/0188529 A1 | 6/2020 | de los Pinos et al. | |
| 2021/0290778 A1 | 9/2021 | de los Pinos et al. | |
| 2021/0393797 A1 | 12/2021 | de los Pinos et al. | |

FOREIGN PATENT DOCUMENTS

| | | |
|---|---|---|
| CN | 102573910 A | 7/2012 |
| CN | 105979967 A | 9/2016 |
| EP | 1491210 A1 | 12/2004 |
| JP | 2005-527493 A | 9/2005 |
| JP | 2007-65646 A | 3/2007 |
| JP | 2009-532564 A | 9/2009 |
| JP | 2012-523455 A | 10/2012 |
| JP | 2016-531591 A | 10/2016 |
| WO | WO 91/03162 A1 | 3/1991 |
| WO | WO 92/07065 A1 | 4/1992 |
| WO | WO 93/15187 A1 | 8/1993 |
| WO | WO 97/26270 A2 | 7/1997 |
| WO | WO 99/15630 A1 | 4/1999 |
| WO | WO 00/09673 A1 | 2/2000 |
| WO | WO 01/55393 A2 | 8/2001 |
| WO | WO 03/008573 A2 | 1/2003 |
| WO | WO 03/061696 A2 | 7/2003 |
| WO | WO 2005/051431 A1 | 6/2005 |
| WO | WO 2005/086667 A2 | 9/2005 |
| WO | WO 2006/125997 A1 | 11/2006 |
| WO | WO 2008/048288 A2 | 4/2008 |
| WO | WO 2008/054184 A1 | 5/2008 |
| WO | WO 2008/103920 A2 | 8/2008 |
| WO | WO 2008/140961 A2 | 11/2008 |
| WO | WO 2010/027827 A2 | 3/2010 |
| WO | WO 2010/120266 A1 | 10/2010 |
| WO | WO 2011/039646 A2 | 4/2011 |

(56) References Cited

FOREIGN PATENT DOCUMENTS

| WO | WO 2013/009717 A1 | 1/2013 |
|---|---|---|
| WO | WO 2013/080187 A1 | 6/2013 |
| WO | WO 2013/119877 A1 | 8/2013 |
| WO | WO 2014/039523 A1 | 3/2014 |
| WO | WO 2015/042325 A1 | 3/2015 |
| WO | WO 2015/075468 A1 | 5/2015 |
| WO | WO 2015/120363 A1 | 8/2015 |
| WO | WO 2015/142675 A2 | 9/2015 |
| WO | WO 2016/139362 A1 | 9/2016 |
| WO | WO 2017/031367 A1 | 2/2017 |

OTHER PUBLICATIONS

Supplementary European Search Report dated Apr. 4, 2017 for Application No. EP 14845738.5.
Extended European Search Report for Application No. EP 19156654.5 dated Jun. 27, 2019.
International Search Report and Written Opinion dated Dec. 29, 2014 for Application No. PCT/US2014/056412.
International Preliminary Report on Patentability dated Mar. 31, 2016 for Application No. PCT/US2014/056412.
[No Author Listed] Bac-to-Bac Baculovirus Expression System. An efficient site-specific transposition system to generate baculovirus for high-level expression of recombinant proteins. Sep. 4, 2010. Retrieved from the Internet on Sep. 23, 2013. 80 pages.
[No Author Listed] GenBank Accession No. P03101, Major Capsid Protein L1, Jan. 11, 2011.
Alvarez, Insertion de sequences peptidiques dans la proteine majeure de capside du papillomavirus de type 16: application au ciblage pulmonaire de vecteurs derives et a la production d'un vaccine chimerique. Thesis. Universite Francois Rabelais. Jun. 20, 2006. 203 pages.
Bergsdorf et al., Highly efficient transport of carboxyfluorescein diacetate succinimidyl ester into COS7 cells using human papillomavirus-like particles. FEBS Lett. Feb. 11, 2003;536(1-3):120-4.
Blackhall et al., Heparan sulfate proteoglycans and cancer. Br J Cancer. Oct. 19, 2001;85(8):1094-8. doi: 10.1054/bjoc.2001.2054.
Bousarghin et al., Inhibition of cervical cancer cell growth by human papillomavirus virus-like particles packaged with human papillomavirus oncoprotein short hairpin RNAs. Mol Cancer Ther. Feb. 2009;8(2):357-65. Epub Jan. 27, 2009.
Brasch et al., Encapsulation of phthalocyanine supramolecular stacks into virus-like particles. J Am Chem Soc. May 11, 2011;133(18):6878-81. doi: 10.1021/ja110752u. Epub Apr. 20, 2011.
Brumfield et al., Heterologous expression of the modified coat protein of Cowpea chlorotic mottle bromovirus results in the assembly of protein cages with altered architectures and function. J Gen Virol. Apr. 2004;85(Pt 4):1049-53.
Buck et al., Efficient intracellular assembly of papillomaviral vectors. J Virol. Jan. 2004;78(2):751-7.
Buck et al., Production of papillomavirus-based gene transfer vectors. Current Protocols in Cell Biology. 26.1.1-26.1.19, Dec. 2007.
Butz et al., siRNA targeting of the viral E6 oncogene efficiently kills human papillomavirus-positive cancer cells. Oncogene. Sep. 4, 2003;22(38):5938-45.
Canti et al., Photodynamic therapy with photoactivated aluminum disulfonated phthalocyanine and cellular immune response. Proc. SPIE 3254, Laser-Tissue Interaction IX (May 13, 1998); doi: 10.1117/12.308158. Event: BIOS '98 International Biomedical Optics Symposium, 1998, San Jose, CA, United States. Retrieved from the Internet: https://www.spiedigitallibrary.org/conference-proceedings-of-spie on Jul. 19, 2019. 8 pages.
Carpentier et al. Mutations on the FG surface loop of human papillomavirus type 16 major capsid protein affect recognition by both type-specific neutralizing antibodies and cross-reactive antibodies. J Med Viral. Dec. 2005;77(4):558-65. Abstract only.
Carpentier et al., Cell targeting for CF gene therapy: Identification of a new specific cell ligand and selection of infectious papillomavirus mutants. J Cystic Fibro. Jun. 1, 2009;8:S31.
Carpentier, Retargeting human papillomavirus-mediated gene transfer to human airway epithelial cells. J Cystic Fibro. Jun. 1, 2010;9:S17.
Carter et al., Identification of a human papillomavirus type 16-specific epitope on the C-terminal arm of the major capsid protein L1. J Virol. Nov. 2003;77(21):11625-32.
Carter et al., Identification of human papillomavirus type 16 L1 surface loops required for neutralization by human sera. J Virol. May 2006;80(10):4664-72.
Christensen et al. Surface conformational and linear epitopes on HPV-16 and HPV-18 L1 virus-like particles as defined by monoclonal antibodies. Virology. Sep. 1, 1996;223(1):174-84.
Cohen et al., Targeted in vitro photodynamic therapy via aptamer-labeled, porphyrin-loaded virus capsids. J Photochem Photobiol B. Apr. 5, 2013;121:67-74. doi: 10.1016/j.jphotobiol.2013.02.013. Epub Feb. 28, 2013.
Combita et al., Gene transfer using human papillomavirus pseudovirions varies according to virus genotype and requires cell surface heparan sulfate. FEMS Microbiol Lett. Oct. 16, 2001;204(1):183-8.
Cook et al., Purification of virus-like particles of recombinant human papillomavirus type 11 major capsid protein L1 from Saccharomyces cerevisiae. Protein Expr Purif. Dec. 1999;17(3):477-84.
Culp et al., Papillomavirus particles assembled in 293TT cells are infectious in vivo. J Virol. Nov. 2006;80(22):11381-4. Epub Aug. 30, 2006.
Davies et al., Distribution and clinical significance of heparan sulfate proteoglycans in ovarian cancer. Clin Cancer Res. Aug. 1, 2004;10(15):5178-86. doi: 10.1158/1078-0432.CCR-03-0103.
Douglas et al., Protein engineering of a viral cage for constrained nanomaterials synthesis. Adv Mater. Mar. 12, 2002;14(6):415-8.
Elbashir et al., Analysis of gene function in somatic mammalian cells using small interfering RNAs. Methods. Feb. 2002;26(2):199-213.
Ewers et al., GM1 structure determines SV40-induced membrane invagination and infection. Nat Cell Biol. Jan. 2010;12(1):11-20; sup pp. 1-12. doi: 10.1038/ncb1999. Epub Dec. 20, 2009.
Feltkamp et al., Vaccination with cytotoxic T lymphocyte epitope-containing peptide protects against a tumor induced by human papillomavirus type 16-transformed cells. Eur J Immunol. Sep. 1993;23(9):2242-9.
Finnen et al., Interactions between papillomavirus L1 and L2 capsid proteins. J Viral. Apr. 2003;77(8):4818-26.
Fleury et al., Identification of neutralizing conformational epitopes on the human papillomavirus type 31 major capsid protein and functional implications. Protein Sci. Jul. 2009;18(7):1425-38.
Gaden et al., Gene transduction and cell entry pathway of fiber-modified adenovirus type 5 vectors carrying novel endocytic peptide ligands selected on human tracheal glandular cells. J Virol. Jul. 2004;78(13):7227-47.
Gillitzer et al., Controlled ligand display on a symmetrical protein-cage architecture through mixed assembly. Small. Aug. 2006;2(8-9):962-6.
Hagensee et al. Self-assembly of human papillomavirus type 1 capsids by expression of the L1 protein alone or by coexpression of the L1 and L2 capsid proteins. Journal of virology. Jan. 1, 1993;67(1):315-22.
Jiang et al., Gel-based application of siRNA to human epithelial cancer cells induces RNAi-dependent apoptosis. Oligonucleotides. 2004 Winter;14(4):239-48.
Jiang et al., Selective silencing of viral gene E6 and E7 expression in HPV-positive human cervical carcinoma cells using small interfering RNAs. Methods Mol Biol. 2005;292:401-20.
Jiang et al., Selective silencing of viral gene expression in HPV-positive human cervical carcinoma cells treated with siRNA, a primer of RNA interference. Oncogene. Sep. 5, 2002;21(39):6041-8.
Jost et al., A novel peptide, THALWHT, for the targeting of human airway epithelia. FEBS Lett. Feb. 2, 2001;489(2-3):263-9.
Kawana et al., In vitro construction of pseudovirions of human papillomavirus type 16: incorporation of plasmid DNA into reassembled L1/L2 capsids. J Virol. Dec. 1998;72(12):10298-300.

(56) References Cited

OTHER PUBLICATIONS

Kines et al., An Infrared Dye-Conjugated Virus-like Particle for the Treatment of Primary Uveal Melanoma. Mol Cancer Ther. Feb. 2018;17(2):565-574. doi: 10.1158/1535-7163.MCT-17-0953. Epub Dec. 14, 2017.
Kines et al., Human papillomavirus capsids preferentially bind and infect tumor cells. Int J Cancer. Feb. 15, 2016;138(4):901-11. doi: 10.1002/ijc.29823. Epub Oct. 27, 2015.
Kirnbauer et al. Efficient self-assembly of human papillomavirus type 16 L1 and L1-L2 into virus-like particles. Journal of virology. Dec. 1, 1993;67(12):6929-36.
Kirnbauer et al. Papillomavirus L1 major capsid protein self-assembles into virus-like particles that are highly immunogenic. Proceedings of the National Academy of Sciences. Dec. 15, 1992;89(24):12180-4.
Lavelle et al., The disassembly, reassembly and stability of CCMV protein capsids. J Virol Methods. Dec. 2007;146(1-2):311-6. Epub Sep. 4, 2007.
Lee et al., Adaptations of nanoscale viruses and other protein cages for medical applications. Nanomedicine. Sep. 2006;2(3):137-49.
Leong et al., Intravital imaging of embryonic and tumor neovasculature using viral nanoparticles. Nat Protoc. Aug. 2005;5(8):1406-17. doi: 10.1038/nprot.2010.103. Epub Jul. 8, 2010.
Li et al., Expression of the human papillomavirus type 11 LI capsid protein in *Escherichia coli*: characterization of protein domains involved in DNA binding and capsid assembly. J Viral. Apr. 1997;71(4):2988-95.
Li et al., Trackable and Targeted Phage as Positron Emission Tomography (PET) Agent for Cancer Imaging. Theranostics. 2011;1:371-80. Epub Nov. 18, 2011.
Lin et al., Treatment of established tumors with a novel vaccine that enhances major histocompatibility class II presentation of tumor antigen. Cancer Res. Jan. 1, 1996;56(1):21-6.
Melero et al., Evolving synergistic combinations of targeted immunotherapies to combat cancer. Nat Rev Cancer. Aug. 2015;15(8):457-72. doi: 10.1038/nrc3973.
Mitsunaga et al., Cancer cell-selective in vivo near infrared photoimmunotherapy targeting specific membrane molecules. Nat Med. Nov. 6, 2011;17(12):1685-91. doi: 10.1038/nm.2554.
Mitsunaga et al., In vivo longitudinal imaging of experimental human papillomavirus infection in mice with a multicolor fluorescence mini-endoscopy system. Cancer Prev Res (Phila). May 2011;4(5):767-73. doi: 10.1158/1940-6207.CAPR-10-0334. Epub Mar. 23, 2011.
Oh et al., Enhanced mucosal and systemic immunogenicity of human papillomavirus-like particles encapsidating interleukin-2 gene adjuvant. Virology. Oct. 24, 2004;328(2):266-73.
Pedersen et al. Immunization of early adolescent females with human papillomavirus type 16 and 18 L1 virus-like particle vaccine containing AS04 adjuvant. Journal of Adolescent Health. Jun. 30, 2007;40(6):564-71.
Peng et al., Construction and production of fluorescent papillomavirus-like particles. J Tongji Med Univ. 1999;19(3):170-4, 180.
Pinto et al. Cellular immune responses to human papillomavirus (HPV)-16 L1 in healthy volunteers immunized with recombinant HPV-16 L1 virus-like particles. Journal of Infectious Diseases. Jul. 15, 2003;188(2):327-38.
Pyeon et al., Production of infectious human papillomavirus independently of viral replication and epithelial cell differentiation. Proc Natl Acad Sci U S A. Jun. 28, 2005;102(26):9311-6. Epub Jun. 15, 2005.
Raja et al., Hybrid virus-polymer materials. 1. Synthesis and properties of PEG-decorated cowpea mosaic virus. Biomacromolecules. May-Jun. 2003;4(3):472-6.
Rhee et al., Glycan-targeted virus-like nanoparticles for photodynamic therapy. Biomacromolecules. Aug. 13, 2012;13(8):2333-8. doi: 10.1021/bm300578p. Epub Jul. 24, 2012. Author manuscript.
Rose et al. Expression of human papillomavirus type 11 L1 protein in insect cells: in vivo and in vitro assembly of viruslike particles. Journal of Virology. Apr. 1, 1993;67(4):1936-44.
Rudolf et al., Human dendritic cells are activated by chimeric human papillomavirus type-16 virus-like particles and induce epitope-specific human T cell responses in vitro. J Immunol. May 15, 2001;166(10):5917-24.
Ruehlmann et al., MIG (CXCL9) chemokine gene therapy combines with antibody-cytokine fusion protein to suppress growth and dissemination of murine colon carcinoma. Cancer Res. Dec. 1, 2001;61(23):8498-503.
Ryding et al., Deletion of a major neutralizing epitope of human papillomavirus type 16 virus-like particles. J Gen Virol. Mar. 2007;88(Pt 3):792-802.
Sadeyen et al., Insertion of a foreign sequence on capsid surface loops of human papillomavirus type 16 virus-like particles reduces their capacity to induce neutralizing antibodies and delineates a conformational neutralizing epitope. Virology. Apr. 25, 2003;309(1):32-40.
Sanderson, Heparan sulfate proteoglycans in invasion and metastasis. Semin Cell Dev Biol. Apr. 2001;12(2):89-98. doi: 10.1006/scdb.2000.0241.
Schädlich et al., Refining HPV 16 L1 purification from *E. coli*: reducing endotoxin contaminations and their impact on immunogenicity. Vaccine. Mar. 4, 2009;27(10):1511-22. Epub Jan. 25, 2009.
Singh, Tumor targeting using canine parvovirus nanoparticles. Curr Top Microbiol Immunol. 2009;327:123-41.
Speir et al., Structures of the native and swollen forms of cowpea chlorotic mottle virus determined by X-ray crystallography and cryo-electron microscopy. Structure. Jan. 15, 1995;3(1):63-78.
Stephanopoulos et al., Dual-surface modified virus capsids for targeted delivery of photodynamic agents to cancer cells. ACS Nano. Oct. 26, 2010;4(10):6014-20. doi: 10.1021/nn1014769.
Touze et al., In vitro gene transfer using human papillomavirus-like particles. Nucleic Acids Res. Mar. 1, 1998;26(5):1317-23.
Touze et al., The L1 major capsid protein of human papillomavirus type 16 variants affects yield of virus-like particles produced in an insect cell expression system. J Clin Microbiol. Jul. 1998;36(7):2046-51.
Touzé et al., The nine C-terminal amino acids of the major capsid protein of the human papillomavirus type 16 are essential for DNA binding and gene transfer capacity. FEMS Microbiol Lett. Aug. 1, 2000;189(1):121-7.
Uchida et al., Biological Containers: Protein Cages as Multifunctional Nanoplatforms. Adv Mater. 2007;19:1025-42.
Varsani et al., Chimeric human papillomavirus type 16 (HPV-16) L1 particles presenting the common neutralizing epitope for the L2 minor capsid protein of HPV-6 and HPV-16. J Virol. Aug. 2003;77(15):8386-93.
Vaysse et al., Improved transfection using epithelial cell line-selected ligands and fusogenic peptides. Biochim Biophys Acta. Jul. 26, 2000;1475(3):369-76.
Wang et al., Insertion of a targeting peptide on capsid surface loops of human papillomavirus type-16 virus-like particles mediate elimination of anti-dsDNA Abs-producing B cells with high efficiency. J Immunother. Jan. 2009;32(1):36-41.
Wang et al., Expression of Human Papillomavirus Type 6 L1 and L2 Isolated in China and Self Assembly of Virus-like Particles by the Products. Acta Biochimica et Biophysica Sinica. 2003;35(1):27-34. 10 pages.
Wang et al., Human papillomavirus type 6 virus-like particles present overlapping yet distinct conformational epitopes. J Gen Virol. Jun. 2003;84(Pt 6):1493-7.
White et al., Genetic modification of adeno-associated viral vector type 2 capsid enhances gene transfer efficiency in polarized human airway epithelial cells. Hum Gene Ther. Dec. 2008;19(12):1407-14.
Willits et al., Effects of the cowpea chlorotic mottle bromovirus beta-hexamer structure on virion assembly. Virology. Feb. 15, 2003;306(2):280-8.
Xu et al., Papillomavirus virus-like particles as vehicles for the delivery of epitopes or genes. Arch Virol. Nov. 2006;151(11):2133-48. Epub Jun. 22, 2006.
Yoshinouchi et al., In vitro and in vivo growth suppression of human papillomavirus 16-positive cervical cancer cells by E6 siRNA. Mol Ther. Nov. 2003;8(5):762-8.

(56) References Cited

OTHER PUBLICATIONS

Zhang et al. Expression of Human Papillomavirus Type 16 L1 Protein in *Escherichia coli*: Denaturation, Renaturation, and Self-Assembly of Virus-like Particlesin Vitro. Virology. Apr. 10, 1998;243(2):423-31.

Zhou et al. Expression of vaccinia recombinant HPV 16 L1 and L2 ORF proteins in epithelial cells is sufficient for assembly of HPV virion-like particles. Virology. Nov. 1, 1991;185(1):251-7.

U.S. Appl. No. 13/264,213, filed Mar. 2, 2012, Granted U.S. Pat. No. 9,724,404.

U.S. Appl. No. 15/636,112, filed Jun. 28, 2017, Granted, U.S. Pat. No. 10,179,168.

U.S. Appl. No. 16/204,019, filed Nov. 29, 201, Granted, U.S. Pat. No. 10,688,172.

U.S. Appl. No. 14/376,408, filed Aug. 1, 2014, Granted, U.S. Pat. No. 9,700,639.

U.S. Appl. No. 15/615,485, filed Jun. 6, 2017, Granted, U.S. Pat. No. 9,855,347.

U.S. Appl. No. 15/824,685, filed Nov. 28, 2017, Granted U.S. Pat. No. 10,300,150.

U.S. Appl. No. 16/376,435, filed Apr. 5, 2019, Granted, U.S. Pat. No. 10,596,275.

U.S. Appl. No. 15/023,169, filed Mar. 18, 2016, Granted, U.S. Pat. No. 10,117,947.

U.S. Appl. No. 16/143,147, filed Sep. 26, 2018, Granted, U.S. Pat. No. 10,588,984.

U.S. Appl. No. 16/778,361, filed Jan. 31, 2020, Granted, U.S. Pat. No. 11,110,181.

U.S. Appl. No. 17/395,369, filed Aug. 5, 2021, Published, 2021-0393797.

U.S. Appl. No. 16/604,790, filed Oct. 11, 2019, Published, 2021-0290778.

PCT/IB2010/002654, Aug. 18, 2011, International Search Report and Written Opinion.

EP 14845738.5, Apr. 4, 2017, Extended European Search Report.

EP 19156541.5, Jun. 27, 2019, Extended European Search Report.

PCT/US2014/056412, Dec. 29, 2014, International Search Report and Written Opinion.

PCT/US2014/056412, Mar. 31, 2016, International Preliminary Report on Patentability.

Extended European Search Report for Application No. EP 22157548.3 dated Augus 11, 2022.

Shitara, Clinical Trials of Combination Therapy to Potentiate Efficacy of Immune Check Point Inhibitors. Journal of Clinical and Experimental Medicine, 2016;258(5):471-479.

\* cited by examiner

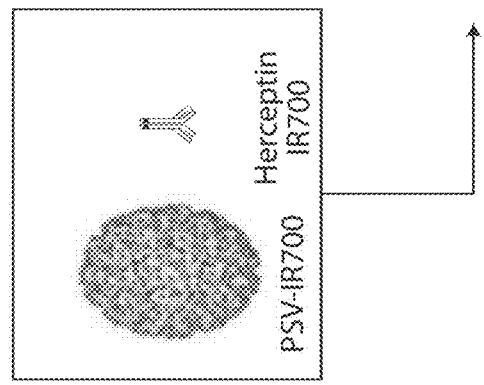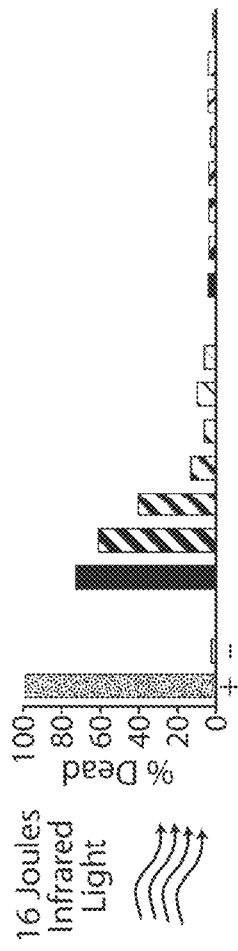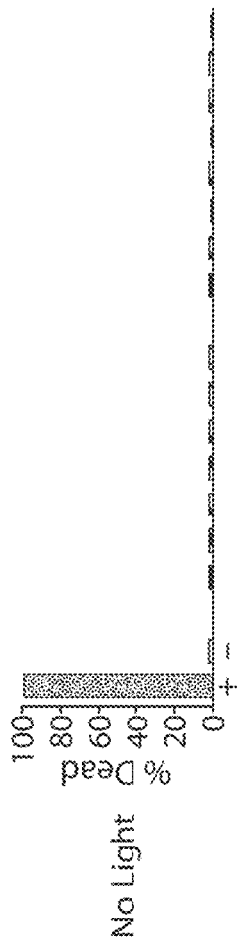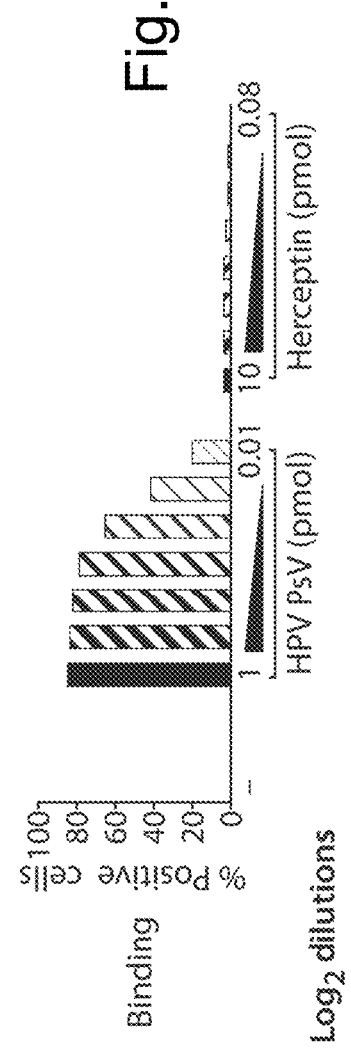
Fig. 7A
Fig. 7B
Fig. 7C

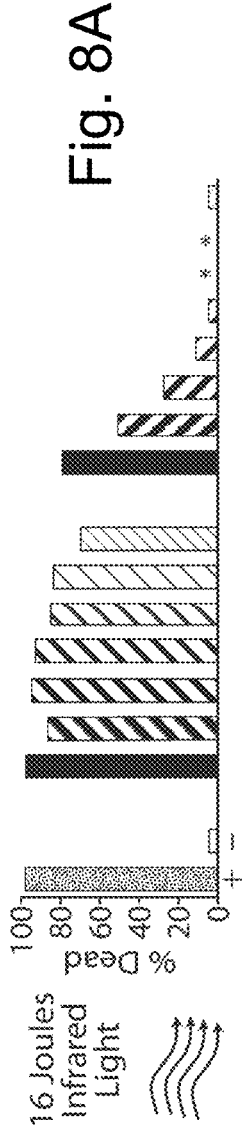
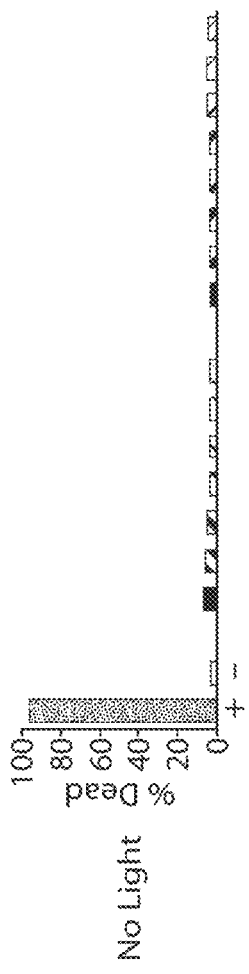
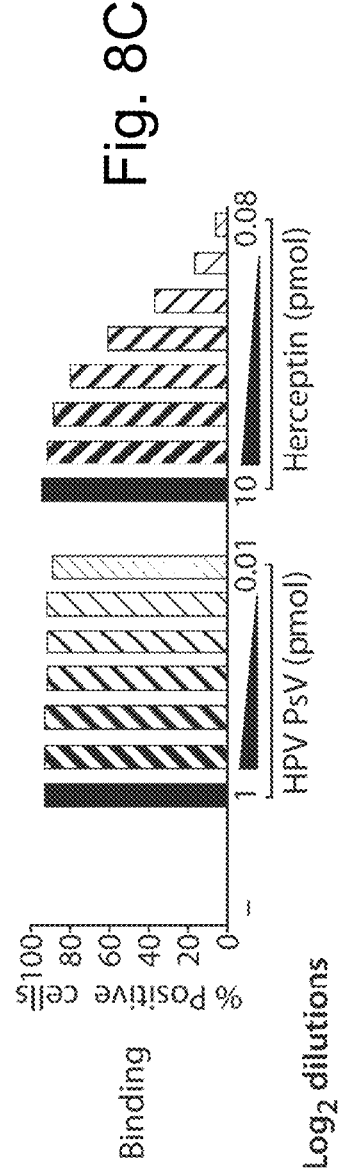
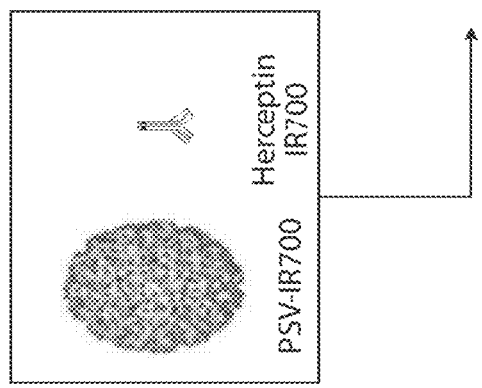

VIRUS-LIKE PARTICLE CONJUGATES FOR DIAGNOSIS AND TREATMENT OF TUMORS

RELATED APPLICATION

This application is a continuation of U.S. application Ser. No. 17/395,369, filed Aug. 5, 2021, which is a continuation of U.S. application Ser. No. 16/778,361, now U.S. Pat. No. 11,110,181, filed Jan. 31, 2020, which is a continuation of U.S. application Ser. No. 16/143,147, now U.S. Pat. No. 10,588,984, filed Sep. 26, 2018, which is a continuation of U.S. application Ser. No. 15/023,169, now U.S. Pat. No. 10,117,947, filed Mar. 18, 2016, which is a national stage filing under 35 U.S.C. § 371 of international application number PCT/US2014/056412, filed Sep. 18, 2014, which was published under PCT Article 21(2) in English and claims the benefit under 35 U.S.C. § 119(e) of U.S. provisional application Ser. No. 61/879,627, filed Sep. 18, 2013, each of which is herein incorporated by reference in its entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Dec. 2, 2021, is named A091570012US05-SEQ-HJD and is 5,072 bytes in size.

FIELD OF THE INVENTION

This disclosure relates to the field of tumor diagnostics and therapeutics.

BACKGROUND OF THE INVENTION

Although numerous treatments are available for cancer, many forms of cancer remain incurable, untreatable or become resistant to standard therapies and effective treatments for many cancers have undesirable side effects. Ocular cancers, such as ocular melanoma and retinoblastoma, are particularly challenging to treat. A patient diagnosed with ocular melanoma, depending on the size of the tumor, has few treatment options, including: (1) surgical procedures such as resection, enucleation or exenteration, all of which are highly invasive and mainly involve the removal of the eye and part of the optic nerve (after surgery the patient is usually fitted for an artificial eye); and (2) plaque brachytherapy, a type of radiation therapy, where a thin piece of metal (e.g., gold) with radioactive seeds covering one side is sewn onto the outside wall of the eye with the seeds aimed at the tumor. The thin piece of metal is removed at the end of treatment, which usually lasts for several days. Severe radioactive related complications include: cataract formation, which is the most common, followed by vitreous hemorrhage. Other complications include dry eye, keratitis, radiation-induced iris neovascularization, neovascular glaucoma, radiation-induced retinopathy, radiation-induced optic neuropathy, episcleral deposits, scleral necrosis and/or extraocular muscle alterations. Radiation retinopathy has been reported to occur in 10-63% of patients treated with plaque brachytherapy, and the mean time from treatment to the development of maculopathy is approximately 25.6 months.

SUMMARY OF THE INVENTION

The present disclosure provides, at least in in part, methods and compositions for detecting and/or selectively targeting tumor cells, for example, for the diagnosis and/or treatment of cancer (e.g., ocular cancer). In some instances, the methods and compositions provided herein can be used to selectively kill cancerous tumor cells without damaging healthy cells. For example, viral-like nanoparticles that comprise (e.g., are conjugated to) photosensitive molecules may be selectively delivered to tumor cells and photoactivated by exposure to light. When photoactivated, a photosensitive molecule absorbs photons, and that absorbed energy produces molecular changes that cause toxicity (e.g., cellular toxicity). A "photosensitive viral-like nanoparticle," (also referred to herein as a "photosensitive virus-like particle") refers to a viral-like nanoparticle conjugated to a photosensitive molecule. Surprisingly, conjugation of photosensitive molecules to viral-like nanoparticles does not interfere with the tissue/tumor tropism of the nanoparticles (e.g., the specificity of the viral-like nanoparticles for a particular host tumor tissue or tumor cell).

Viral-like nanoparticles (also referred to as virus-like particles (VLPs)) of the present disclosure, generally, are assembled from L1 capsid proteins, or a combination of L1 and L2 capsid proteins, and the photosensitive molecules, in some embodiments, are conjugated to a capsid protein that forms the viral-like nanoparticle. Thus, various aspects of the disclosure provide tumor-targeting viral-like nanoparticles that comprise photosensitive molecules conjugated to capsid proteins.

Some aspects of the disclosure also provide tumor-targeting virus-like particles that comprise about 50 to about 500, about 50 to about 600, about 50 to about 700, about 50 to about 800, about 50 to about 900, or about 50 to about 1000 photosensitive molecules per particle. In some embodiments, tumor-targeting virus-like particles comprise about 400, about 500, about 600, about 700, about 800, about 900 or about 1000 photosensitive molecules per particle. In some embodiments, tumor-targeting virus-like particles comprise 500 photosensitive molecules or 1000 photosensitive molecules per particle.

In some embodiments, the capsid proteins are papilloma virus capsid proteins. For example, in some embodiments, the papilloma virus capsid proteins are non-human papilloma virus capsid proteins, such as bovine papilloma virus capsid proteins. In some embodiments, the virus-like particles comprise human papilloma virus capsid proteins and do not cross-react with human papilloma virus (HPV) 16, HPV 18 or pre-existing antibodies specific for HPV.

In some embodiments, the virus-like particles comprise papilloma L1 or L1/L2 proteins (e.g., of human, bovine, or other species). In some embodiments, the L1 or L1/L2 VLPs do not cross-react with neutralizing antibodies to human papilloma virus (HPV) 16, HPV 18 or pre-existing antibodies specific for other HPVs. However, in some embodiments, the virus-like particles comprise human papilloma virus capsid proteins of HPV16.

In some embodiments, the photosensitive molecules are conjugated to surface-exposed peptides of capsid proteins.

In some embodiments, the virus-like particles comprise L1 capsid proteins or a combination of L1 and L2 capsid proteins. In some embodiments, the virus-like particles consist of L1 capsid proteins.

In some embodiments, a virus-like particle comprises BPV L1 capsid protein (e.g., SEQ ID NO: 2), a combination of BPV L1 and BPV L2 capsid proteins. In some embodiments, a virus-like particle comprises HPV L1 capsid proteins, or a combination of HPV L1 and HPV L2 capsid proteins. In some embodiments, the HPV L1 capsid protein is a variant HPV16/31 L1 protein having modified immunogenicity and/or antigenicity (e.g., SEQ ID NO: 1). Thus, in some embodiments, a virus-like particle comprises or consists of variant HPV16/31 L1 capsid proteins or a combination of variant HPV16/31 L1 capsid proteins (e.g., SEQ ID NO: 1) and HPV L2 capsid proteins.

In some embodiments, the capsid proteins of a virus-like particle have modified immunogenicity and/or antigenicity. A non-limiting example of such a capsid protein is HPV16/31 L1 capsid proteins (e.g., SEQ ID NO: 1). Virus-like particles that contain modified capsid proteins may be referred to herein as virus-like particles that contain modified immunogenicity and/or antigenicity compared to wild-type virus-like particles.

In some embodiments, the photosensitive molecules are covalently conjugated to capsid proteins. In some embodiments, the photosensitive molecules are conjugated to an amino acid of the capsid proteins. In some embodiments, the photosensitive molecules are conjugated to an amine group (e.g., primary aliphatic amine) of an amino acid of the capsid proteins. In some embodiments, the photosensitive molecules are conjugated to amine groups of lysine residues (e.g., side chain amine of lysine) of the capsid proteins. In some embodiments, the photosensitive molecules are conjugated to amine groups of arginine and/or histidine residues) of the capsid proteins. The present disclosure provides methods for conjugating photosensitive molecules to lysine and other amino acids that contain amine groups.

In some embodiments, the photosensitive molecules do not compromise (e.g., prevent, interfere with or inhibit) binding of the virus-like particle to the surface of tumor cells. In some embodiments, the photosensitive molecules do not compromise (e.g., prevent, interfere with or inhibit) binding of the virus-like particle to heparan sulphate proteoglycans or other polysaccharides on the surface of tumor cells.

In some embodiments, the virus-like particles comprise about 10 to about 1000 photosensitive molecules. In some embodiments, the virus-like particles comprise about 50 to about 1000 photosensitive molecules. In some embodiments, the virus-like particles comprise about 100 to about 1000 photosensitive molecules. In some embodiments, the virus-like particles comprise about 100 to about 500 photosensitive molecules. In some embodiments, the virus-like particles comprise about 500 to about 1000 photosensitive molecules, or more.

In some embodiments, the virus-like particles comprise about 10 to about 1000 photosensitive molecules that are conjugated to lysine residues or other amino acid residues of L1 capsid proteins, L2 capsid proteins, or a combination of L1 capsid proteins and L2 capsid proteins.

In some embodiments, the photosensitive molecules are activated by infrared, near-infrared or ultraviolet light. A photosensitive molecule is considered to be "activated" when the molecule absorbs photons, and that absorbed energy produces molecular changes that cause toxicity, as described elsewhere herein.

In some embodiments, the photosensitive molecules comprise a fluorescent dye, an infrared dye, a near infrared dye, a porphyrin molecule, a chlorophyll molecule, or a combination of any two or more of the foregoing.

In some embodiments, the photosensitive molecules are porphyrin molecules. Examples of porphyrin molecules for use in accordance with the present disclosure include, without limitation, HpD (hematoporphyrin derivative), HpD-based, BPD (benzoporphyrin derivative), ALA (5-aminolevulinic acid) and texaphyrins. In some embodiments, the porphyrin molecule is verteporfin (Visudyne®)

In some embodiments, the photosensitive molecules are chlorophyll molecules. Examples of chlorophyll molecules for use in accordance with the present disclosure include, without limitation, chlorins, purpurins and bacteriochlorins.

In some embodiments, the photosensitive molecules are dyes. Examples of dyes for use in accordance with the present disclosure include, without limitation, phthalocyanine and naphthalocyaninc.

In some embodiments, the phthalocyanine dye is both a fluorescent molecule and a near infrared molecules. For example, in some embodiments, the phthalocyanine dye is IR700 dye (e.g., IRDye® 700DX, LI-COR®). An IR700 dye is a fluorescent dye that has an absorption and emission wavelengths in the near-infrared (NIR) spectrum typically between 680 nm and 800 nm. Other fluorescent dyes having an absorption and emission wavelengths in the NW spectrum are provided herein.

In some embodiments, photosensitive molecules are selected from phthalocyanine dyes (e.g., IR700 dye such as IRDye® 700DX), porphyrin molecules (e.g., verteporfin such as Visudyne®) and a combination of phthalocyanine dyes and porphyrin molecules.

Some aspects of the disclosure provide methods that comprise administering, to a subject having a tumor, any one of the virus-like particles, or photosensitive virus-like particles, provided herein. In some embodiments, the methods comprise activating the photosensitive molecules of a virus-like particle at a wavelength of light that permits visualization of the light sensitive molecules. Thus, in some embodiments, the photosensitive molecules of the present disclosure are used as imaging agents and/or diagnostic agents. In some embodiments, the methods comprise activating the photosensitive molecules at a wavelength of light that causes the molecule to be cytotoxic. In some embodiments the methods comprise activating the photosensitive molecules at a wavelength of light generating an energy transfer within the tumor cell that creates direct and irreversible cell damage leading to necrosis. Thus, in some embodiments, the photosensitive molecules of the present disclosure are used as therapeutic and/or prophylactic agents.

Some aspects of the disclosure provide methods that comprise administering, to a subject having a tumor, a tumor-targeting virus-like particle comprising photosensitive molecules conjugated to capsid proteins. In some embodiments, the methods comprise activating photosensitive molecules of the virus-like particles at a wavelength that renders the molecules visible. That is, the photosensitive molecules re-emit light upon light excitation. In some embodiments, the methods comprise activating photosensitive molecules at a wavelength that renders the molecules cytotoxic, thereby killing cells of the tumor. That is, the photosensitive molecules undergo a molecular change upon light excitation that results in the photosensitive molecules become toxic to cells.

Some aspects of the disclosure provide methods that comprise administering, to a subject having a tumor, a tumor-targeting virus-like particle comprising about 50 to about 1000, about 50 to 500, or about 500 to 1000 photosensitive molecules. In some embodiments, methods comprise administering, to a subject having a tumor, a tumor-targeting virus-like particle comprising about 100, 200, 300, 400, 500, 600, 700, 800, 900, 1000 or more photosensitive molecules. In some embodiments, the methods comprise activating photosensitive molecules at a wavelength that renders the molecules visible. In some embodiments, the methods comprise activating photosensitive molecules at a wavelength that renders the molecules cytotoxic, thereby killing cells of the tumor.

In some embodiments, the photosensitive molecules are laser activated. In some embodiments, the laser is an infrared, near-infrared or ultraviolet laser. In some embodiments, the infrared laser is 5 Joules (J) to 100 J (or J/cm$^2$) (e.g., 5 J, 6 J, 7 J, 8 J, 9 J, 10 J, 11 J, 12 J, 13 J, 14 J. 15 J, 16 J, 17 J. 18 J, 19 J, 20 J, 21 J, 22 J, 23 J, 24 J, 25 J, 26 J. 27 J, 28 J, 29 J. 30 J, 31 J, 32 J, 33 J, 34 J, 35 J, 36 J, 37 J, 38 J, 39 J, 40 J, 41 J, 42 J, 43 J, 44 J, 45 J, 46 J, 47 J. 48 J, 49 J, 50 J. 51 J, 52 J, 53 J, 54 J, 55 J, 56 J, 57 J, 58 J, 59 J, 60 J, 61 J, 62 J, 63 J, 64 J, 65 J. 66 J, 67 J, 68 J. 69 J, 70 J, 71 J, 72 J, 73 J, 74 J, 75 J, 76 J, 77 J, 78 J, 79 J, 80 J. 81 J, 82 J, 83 J. 84 J, 85 J, 86 J, 87 J, 88 J, 89 J, 90 J, 91 J, 92 J. 93 J, 94 J, 95 J. 96 J, 97 J, 98 J, 99 J or 100 J (or J/cm$^2$)). In some embodiments, the laser is applied for about 5 seconds to about 5 minutes.

In some embodiments, the photosensitive molecules are activated at about 30 minutes to about 48 hours after administering the virus-like particles to a subject. For example, the photosensitive molecules may be activated at 30 minutes after administering the virus-like particles to a subject. In some embodiments, the photosensitive molecules are activated 1 hour, 2 hours (h), 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 or 24 h after administering the virus-like particle to a subject. In some embodiments, the photosensitive molecules are activated 1 day, 2 days or 3 days after administering the virus-like particle to a subject.

In some embodiments, the tumor is an ocular tumor or a tumor that has metastasized to the eye. For example, in some embodiments, the ocular tumor is located in the vitreous, choroidal space, iris, ciliary body, sclera, fovea, retina, optic disk or optic nerve.

In some embodiments, the tumor is located in a lung, pleura, liver, pancreas, stomach, esophagus, colon, breast, ovary, prostate, brain, meninges, testis, gastrointestinal tract, kidneys or bladder.

In some embodiments, the tumor is accessible without surgical intervention.

In some embodiments, the tumor is located in the head, neck, cervix, larynx or skin.

In some embodiments, the tumor is an orphan or rare disease.

In some embodiments, the tumor is cancerous. In some embodiments, the tumor is metastatic. In some embodiments, the tumor is pre-cancerous or dysplastic.

In some embodiments, the virus-like particles are administered by injection. For example, the virus-like particles may be administered by injection intraocularly, into the vitreous, or intravenously. In some embodiments, the virus-like particles are administered with a hollow or coated needle, mini-needle or micro-needle. In some embodiments, the virus-like particles are administered topically. In some embodiments, the virus-like particles are administered by implantation.

In some embodiments, the capsid proteins are papilloma virus capsid proteins. For example, in some embodiments, the papilloma virus capsid proteins are non-human papilloma virus capsid proteins, such as bovine papilloma virus (BPV) capsid proteins. In some embodiments, the virus-like particles comprise human papilloma virus capsid proteins and do not cross-react with human papilloma virus (HPV) 16, HPV 18 or pre-existing antibodies specific for HPV. In some embodiments, the virus-like particles comprise human papilloma virus type 16 capsid proteins. In some embodiments the VLPs do not bind antibodies specific for human papilloma virus (HPV) 16, HPV 18 VLPs or pre-existing antibodies specifically induced by HPV infection.

Some aspects of the disclosure provides methods of detecting, in a subject, tumors (e.g., ocular tumors and malignant nevi), the methods comprising administering to the subject (e.g., to the eye of the subject) any one of the virus-like particle provided herein, such as a virus-like particle comprising a photosensitive molecule (e.g., fluorescent dye or infrared dye), and detecting the location of the tumor. In some embodiments, the methods comprise detecting the location of the tumor by illuminating the subject (e.g., eye of the subject) with a laser (e.g., ultra-violet or infrared laser). In some embodiments, the methods comprise identifying the subject suspected of having a tumor before administering the virus-like particle. In some embodiments, the methods comprise diagnosing and/or treating the tumor by administering photosensitive virus-like particles to a tumor of the subject or to the a subject having or suspected of having a tumor.

Other aspects of the disclosure provide methods of selectively inhibiting proliferation or killing of cancerous cells without inhibiting proliferation or viability of non-cancerous (e.g., normal, healthy) cells, the methods comprising administering to a tumor of a subject (e.g., to an ocular tumor of the subject) any one of the tumor-targeting virus-like particles provided herein, such as virus-like particles comprising photosensitive molecules (e.g., infrared dye), and irradiating cancerous cells of the tumor by subjecting the tumor to an infrared laser (e.g., at a wavelength of about 660 nm to 740 nm and at a dose of at least 8 Joules), effectively.

In some embodiments, the present disclosure provides a viral-like nanoparticle (also referred to as a virus-like particle) comprising photosensitive molecules conjugated to papilloma virus L1 proteins (e.g., bovine papilloma virus L1 proteins). In some embodiments, the viral-like nanoparticles are 20 to 60 nanometers (e.g., 10, 25, 30, 35, 40, 45, 50, 55 or 60 nanometers) in diameter. In some embodiments, a viral-like nanoparticle contains 300 to 500 L1 (e.g., BPV L1) capsid proteins, for example 360 L1 capsid proteins (e.g., based on icosahedral symmetry). It should be appreciated that in some embodiments, viral-like nanoparticles each contain about 300, 310, 320, 330, 340, 350, 360, 370, 380, 390, 400, 410, 420, 430, 440, 450, 460, 470, 480, 490 or 500 L1 (e.g., BPV L1) capsid proteins. However, in some embodiments, a viral-like nanoparticle contains less than 300 L1 (e.g., BPV L1) capsid proteins.

In some embodiments, the present disclosure provides a bovine papilloma virus viral-like nanoparticle covalently conjugated to 100 to 1000 photosensitive molecules (e.g., 100, 200, 300, 400, 500, 600, 700, 800, 900 or 1000 molecules). In some embodiments, the capsid proteins of the bovine papilloma virus (BPV) viral-like nanoparticle comprise or consist of BPV L1 capsid proteins or a combination of BPV L1 and BPV L2 capsid proteins. In some embodiments, the photosensitive molecules are conjugated to the viral-like nanoparticles (or to capsid proteins of the viral-like nanoparticles) through a covalent bond formed by reacting an ester group in the photosensitive molecules with an amine group in the capsid proteins, thereby forming an amide bond. Thus, in some embodiments, capsid proteins of viral-like nanoparticles of the present disclosure are conjugated to photosensitive molecules through amide bonds.

In some embodiments, the present disclosure provides a viral-like nanoparticle comprising 300 to 500 BPV L1 capsid proteins and/or a diameter of 20 60 nm, at least some of which (e.g., 10%, 20%, 30%, 40%, 50%, 60%, 70%, 80%, 90% or 100%) are covalently conjugated (e.g., through an amide bond) to 1 to 5 (e.g., 1, 2, 3, 4 or 5) photosensitive molecules (e.g., IR700 dye such as IRDye® 700DX). The present disclosure also provide methods of producing viral-like nanoparticles and methods of administering viral-like nanoparticles to a subject as a diagnostic, therapeutic or prophylactic agent.

BRIEF DESCRIPTION OF THE DRAWINGS

FIGS. 7A-7C show graphs of cell death of a human epidermal growth factor receptor 2 negative (HER2) ocular melanoma cell line (92.1), comparing the effectiveness of bivalent agents (e.g., antibodies) and multivalent agents (e.g., photosensitive VLPs, also referred to as VLP conjugates, designated POI in the figure).

FIGS. 8A-8C show graphs of cell death of an human epidermal growth factor receptor 2 positive (HER2*) ovarian cancer cell line (SKOV-3), comparing the effectiveness of bivalent agents (e.g., antibodies) and multivalent agents (e.g., photosensitive VLPs, also referred to as VLP conjugates, designated PsV in the figure).

FIG. 18 (bottom panel) shows percentage of dead cells for each of the six test conditions.

DETAILED DESCRIPTION OF THE INVENTION

Figure 1:
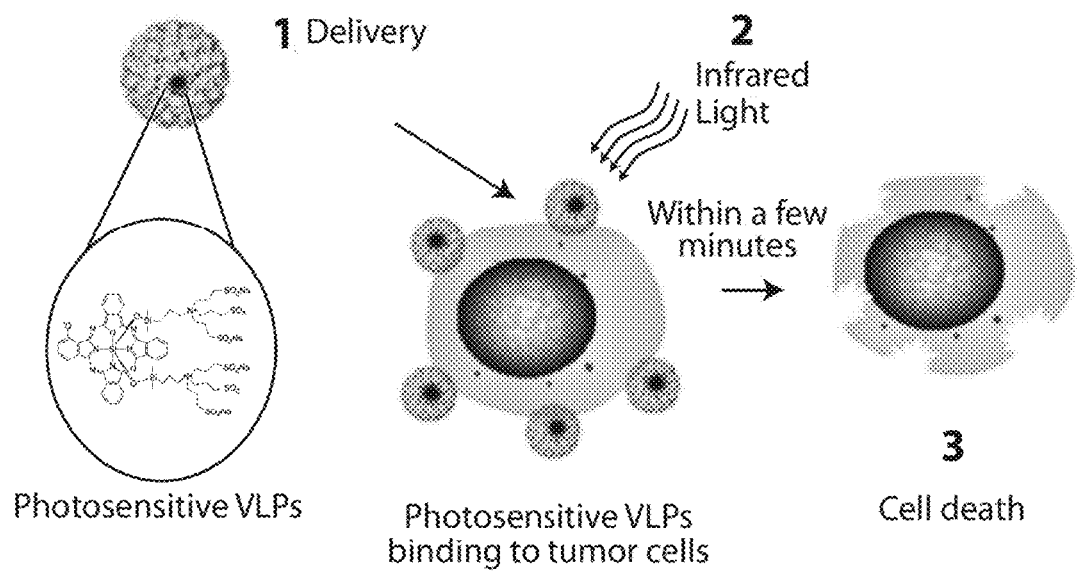
FIG. 1 shows a mechanism for inducing eel death using a virus-like particle (VLP) conjugated to a photosensitive molecule.
Figure 2:
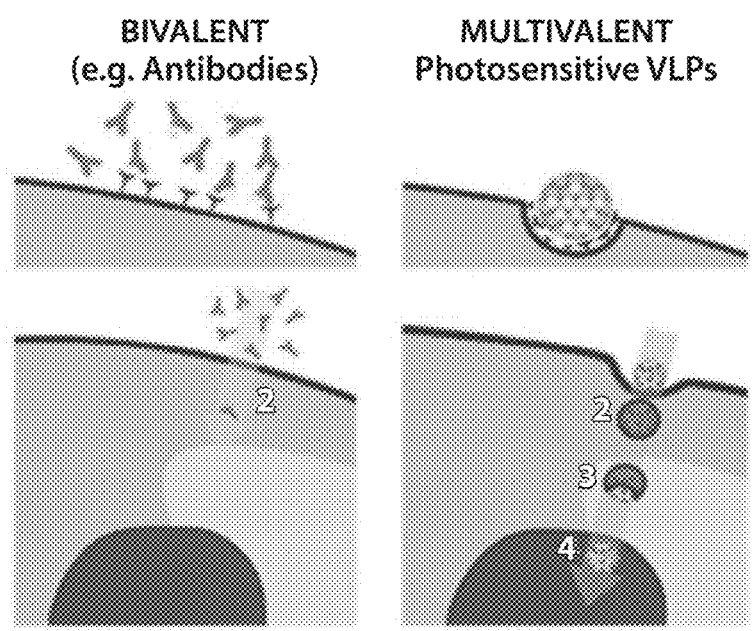
FIG. 2 shows a comparison of bivalent targeting, e.g., by an antibody, and multivalent targeting, e.g., by a VLP.

Photodynamic therapy (PDT) is a form of phototherapy using nontoxic photosensitive molecules that, when selectively exposed to light, become toxic, and target and/or kill, malignant and other diseased cells. A challenge posed by PDT in the treatment of cancer is the delivery of high concentrations of photosensitive molecules exclusively to tumor cells. To achieve targeted delivery, antibodies can be used, though they are limited by their delivery capacity, which is in the range of 2-8 photosensitive molecules per antibody. Further, there are important tumors that lack an identified tumor receptor molecule and, thus, cannot be targeted with an antibody. As a consequence, multiple tumors remain untreatable (e.g., ocular melanoma). In addition, many of the molecules (e.g., EGFR) targeted by antibody/dye conjugates are also found on the surface of non-tumor cells, leading to unwanted off target effects.

The present disclosure is based, in part, on the unexpected discovery that virus-like particles (VLPs) (e.g., papilloma VLPs) (also referred to herein as viral-like nanoparticles) can be chemically modified to carry many photosensitive molecules (e.g., IR700) without losing their tumor-targeting capability or structural stability. For example, in some embodiments, VLPs can be chemically modified to carry more than 50 molecules, more than 100 molecules, or more than 1000 molecules (or about 1000 photosensitive molecules). Virus-like particles assembled from L1, or L1 and L2 capsid proteins, can selectively bind to and infect cancer cells without affecting non-cancerous cells, thereby minimizing the cytotoxicity of treatments (see U.S. Patent Application Publication No. US20100135902A1, the entirety of which is incorporated by reference herein). Further, in some instances, the delivery of high amounts of photosensitive molecules per particle enables the selective killing of tumor cells upon light radiation with extremely small amounts of drug (e.g., picomolar concentrations).

A key cell binding characteristic of a VLP is the presence of a high number of heparin binding sites on the capsid proteins (e.g., L1). Conjugation of photosensitive molecules to surface amino acids (e.g., conjugation via an amide bond to surface amino acids such as surface lysine residues, arginine residues and histidine residues), surprisingly, does not compromise binding of the VLP to heparan sulphate proteoglycans (HSPGs) on the surface of tumor cells. Although, the present disclosure describes conjugation of photosensitive molecules to surface-exposed peptides of capsid proteins, it should be understood that photosensitive molecules may be conjugated to any peptides of capsid proteins. That is, photosensitive molecules may be conjugated to L1 proteins only or to a combination of L1 and L2 proteins. The protein and amino acid residue to which a photosensitive molecule is conjugated can depend on the composition of the virus-like particle.

The foregoing discoveries have important implications for the development of novel targeted cancer treatments. For example, the photosensitive VLPs (also referred to as VLP conjugates) of the present disclosure provide an advantage relative to other targeting molecules such as antibodies, which have a very limited delivery capacity. In addition, the photosensitive VLPs of the present disclosure are useful for targeting a wide range of tumors that otherwise cannot be targeted by antibodies or other targeting molecules (e.g., ocular tumors) because suitable tumor-surface specific determinants have not been identified. Further, the photosensitive VLPs are useful for treating distant metastases. In addition the photosensitive VLPs are useful for diagnosis and treatment of early malignant or pre-cancerous lesions (e.g., ocular nevi that are transformed, pre-malignant or malignant).

A "virus-like particle" (VLP), as used herein, refers to an organized capsid-like structure (e.g., roughly spherical or cylindrical in shape) that comprises self-assembling ordered arrays of L1 or L1 and L2 capsomers and does not include a viral genome. Virus-like particles are morphologically and antigenically similar to authentic virions, but they lack viral genetic material (e.g., viral nucleic acid), rendering the particles non-infectious. A VLP may be used to deliver to a recipient cell an agent (e.g., prophylactic agent, therapeutic agent or diagnostic agent) or an enclosed circular or linear DNA or RNA molecule. It should be understood that the terms "virus-like particle," or "VLP" and "pseudovirus," or "PsV" may be used interchangeably herein and may also be used interchangeably with the term "viral-like nanoparticle."

A "tumor-targeting virus-like particle," as used herein, refers to a VLP that targets tumor (e.g., cancerous) cells without targeting non-tumor (e.g., non-cancerous, otherwise normal, healthy) cells (e.g., in intact tissue).

VLPs in accordance with the present disclosure may have a modified immunogenicity and/or antigenicity with respect to the wild type papillomavirus VLPs. The VLPs may, for example, be assembled from capsomers having a variant capsid protein with modified immunogenicity and/or antigenicity. A variant capsid protein with "modified immunogenicity and/or antigenicity" is one that is modified naturally or synthetically (e.g., mutated, substituted, deleted, pegylated or inserted) at an amino acid to reduce or prevent recognition of the capsid protein by pre-existing (e.g., endogenous) viral serotype-specific antibodies. A variant capsid protein may be a human papillomavirus (HPV) L1 variant, a non-human papillomavirus L1 variant, or a papillomavirus L1 variant based on a combination of amino acids from different HPV serotypes. For example, an L1 variant with modified immunogenicity and/or antigenicity may be a recombinant protein based on HPV serotype 16 and HPV serotype 31 (referred to herein as a "variant HPV16/31 L1 protein"—SEQ ID NO: 1), which is described in International Pub. No. WO/2010/120266, the entirety of which is incorporated by reference herein.

In some embodiments, a VLP is a papilloma virus VLP. The VLP may be a human papilloma virus VLP (e.g., derived from a virus that can infect human), while in other embodiments, the VLP is a non-human papilloma virus VLP. Examples of non-human VLPs include those derived from, without limitation, bovine papilloma viruses, murine papilloma viruses, cotton-rabbit papilloma viruses and macaque or rhesus papilloma virus particles. In some embodiments, the VLPs are bovine papilloma virus viral-like nanoparticles (e.g., type 1 viral-like nanoparticles) (e.g., assembled from BPV L1 capsid proteins or a combination of BPV L1 and BPV L2 capsid proteins).

A "capsid protein," as used herein, refers to a protein monomer, several of which form a capsomer oligomer. A "capsomer," as used herein, refers to the basic oligomeric structural unit of a viral capsid, which is an outer covering of protein that protects the genetic material of a virus such as, for example, human papillomavirus (HPV). The capsid proteins of the present disclosure include papillomavirus L1 major capsid proteins and papillomavirus L2 minor capsid proteins. In some embodiments, the VLPs of the present disclosure contain only L1 capsid proteins, while in other embodiments, the VLPs contain a mixture (or combination) of L1 and L2 capsid proteins.

In some embodiments, the percentage of L1 capsid proteins in a virus-like particle is greater than the percentage of L2 capsid proteins in the virus-like particle. For example, in some embodiments, the percentage of L1 capsid proteins in a virus-like particle is 80% to 100% (of the total number of capsid proteins in the virus-like particle). In some embodiments, the percentage of L1 capsid proteins in a virus-like particle is 80%, 85%, 90%, 91%, 92%, 93%, 94%, 95%, 96%, 97%, 98%, 99% or 100%. In some embodiments, the percentage of L2 capsid proteins in a virus-like particle is 1% to 25% (of the total number of capsid proteins in the virus-like particle). For example, some embodiments, the percentage of L2 capsid proteins in a virus-like particle is 1%, 2%, 3%, 4%, 5%, 6%, 7%, 8%, 9%, 10%, 11%, 12%, 13%, 14%, 15%, 16%, 17%, 18%, 19% or 20%.

In some embodiment, a virus-like particle contains 12 to 72 L2 proteins. In some embodiment, a virus-like particle contains 360 L1 proteins and 12 to 72 L2 proteins. In some embodiments, capsid proteins assemble into viral-like nanoparticles having a diameter of 20 to 60 nm. For example, capsid proteins may assemble into viral-like nanoparticles having a diameter of 20, 25, 30, 35, 40, 45, 50, 55 or 60 nm.

An "external capsid protein," as used herein, refers to a capsid protein that is exposed at the surface of a VLP. In some embodiments, external capsid proteins (e.g., L1 proteins) are conjugated to a (e.g., at least one) photosensitive molecule.

A "photosensitive molecule," as used herein, refers to a nontoxic molecule that, when exposed selectively to light, becomes "activated" (also referred to as "photoactivated"). In some embodiments, an activated photosensitive molecule re-emits light upon light excitation (e.g., a fluorophore). In some embodiments, an activated photosensitive molecule can become toxic, or can produce toxic molecules, upon light excitation. For example, a class of photosensitive molecules, referred to as photosensitizers, can be promoted to an excited state upon absorption of light and undergo intersystem crossing with oxygen to produce singlet oxygen. This singlet oxygen rapidly attacks any organic compounds it encounters, thus is highly cytotoxic.

In accordance with various aspects of the present disclosure, photosensitive molecules may be conjugated to capsid proteins (e.g., L1 and/or L2 capsid proteins) of the VLPs. In some embodiments, the photosensitive molecules are covalently conjugated to capsid proteins of the VLPs. In some embodiments, the photosensitive molecules are covalently conjugated to lysine residues of capsid proteins of the VLPs. VLPs that are conjugated to photosensitive molecules may be referred to herein as "VLP conjugates" or "photosensitive VLPs." In some embodiments, the photosensitive molecules comprise an NHS (N-Hydroxysuccinimide) ester group that reacts with an amine group of the capsid protein (e g amine group of lysine or other amino acid) to form a covalent amide bond.

The ratio of photosensitive molecule (PM) to VLP may vary. In some embodiments the ratio of VLP:PM is about 1:10 to about 1:1000, about 1:10 to about 1:500, about 1:50 to about 1:500, or about 1:50 to about 1:1000. That it, in some embodiments, a VLP may comprise about 10 to about 1000 photosensitive molecules. In some embodiments, the ratio of VLP:PM is 1:10, 1:15, 1:20, 1:25, 1:50, 1:75, 1:100, 1:150, 1:200, 1:250, 1:300, 1:350, 1:400, 1:450, 1:500, 1:550, 1:600, 1:650, 1:700, 1:750, 1:800. 1:850, 1:900, 1:950 or 1:1000. In some embodiments, the VLP may comprise 10, 15, 20, 50, 75, 100, 150, 200, 250, 300, 350, 400, 450, 500, 550, 600, 650, 700, 750, 800, 850, 900, 950 or 1000 photosensitive molecules. In some embodiments, the VLP may comprise more than 1000 photosensitive molecules or less than 10 photosensitive molecules.

More than one photosensitive molecule may be conjugated to a single capsid protein. For example, a single capsid protein (e.g., L1 or L2 capsid protein) may be conjugated to 1 to 5 (e.g., 1, 2, 3, 4 or 5) photosensitive molecules. Thus, more than one amino acids of a capsid protein may be conjugated to a photosensitive molecule. In some embodiments, a single capsid protein may be conjugated to 1 to 2, 1 to 3, or 2 to 3 photosensitive molecules. Thus, a photosensitive molecule may be conjugated to 1, 2, 3, 4 or 5 different amino acids (e.g., lysine, arginine and/or histidine, or other amino acid) of a single capsid protein.

Examples of photosensitive molecules for use in accordance with the present disclosure include, without limitation, fluorescent dyes, infrared dyes, near infrared dyes, porphyrin molecules and chlorophyll molecules.

Examples of fluorescent dyes for use in accordance with the present disclosure include, without limitation, acridine orange, acridine yellow, Alexa Fluor, 7-Aminoactinomycin D, 8-Anilinonaphthalene-1-sulfonic acid, ATTO dyes, auramine-rhodamine stain, benzanthrone, bimane, 9,10-Bis(phenylethynyl)anthracene, 5,12-Bis(phenylethynyl)naphthacene, bisbenzimide, blacklight paint, calcein, carboxyfluorescein, carboxyfluorescein di acetate succinimidyl ester, carboxyfluorescein succinimidyl ester, 1-chloro-9,10-bis(phenylethynyl)anthracene, 2-chloro-9,10-bis(phenylethynyl)anthracene, 2-chloro-9,10-diphenylanthracene, coumarin, DAPI, dark quencher, DiOC6, DyLight Fluor, Fluo-3, Fluo-4, FluoProbes, fluorescein, fluorescein isothiocyanate, fluorescence image-guided surgery, fluorojade stain, fura-2, fura-2-acetoxymethyl ester, GelGreen, GelRed, green fluorescent protein, heptamethine dyes, Indian yellow, Indo-1, Lucifer yellow, luciferin, MCherry, Merocyanine, Nile blue, Nile red, optical brightener, perylene, phloxine, phycobilin, phycocrythrin, phycocrythrobilin, propidium iodide, pyranine, rhodamine, rhodamine 123, Rhodamine 6G, RiboGreen, RoGFP, rubrene, (E)-stilbene. (Z)-stilbene, sulforhodamine 101, sulforhodamine B, SYBR Green I, synapto-pHluorin, tetraphenyl butadiene, tetrasodium tris(bathophenanthroline disulfonate)ruthenium (II), Texas Red, Titan yellow, TSQ, umbelliferone, yellow fluorescent protein and YOYO-1.

Examples of photosensitizing dyes for use in accordance with the present disclosure include, without limitation, HpD, Porfimer sodium(Photofrin®, Photogem®, Photosan Hemporfin®), m-THPC, Temoporfin (Foscan®), Verteporfin (Visudyne®), HPPH (Photochlor®), Palladium-bacteria-pheophorbide (Tookad®,) 5-ALA, 5 aminolevulinic acid (Levulan®), 5-ALA methylester (Metvix®), 5-ALA henzylester (Benzvix®), 5-ALA hexylester (Hexvix®), lutetium (III)-texaphyrin or Motexafin-lutetium (Lutex®, Lutrin®, Angrin®, Optrin®), SnET2, Tin (IV) ethyl etiopurpurin (Purlytin®, Photrex®), NPe6, mono-L-aspartyl chlorine e6, talaporfin sodium (Talporfin®, Laserphyrin®), BOPP, boronated protoporphyrin (BOPP®), Zinc phthalocyanine (CGP55847®), silicon phthalocyanine (Pc40), mixture of sulfonated aluminium phthalocyanine derivatives (Photosens®), ATMPn, Acetoxy-tetrakis (beta-methoxyethyl-)porphycene), TH9402 and dibromorhodamine methyl ester.

Examples of photosensitizing dyes for use in accordance with the present disclosure include those that can be used in fluorescence imaging (e.g., near infrared (NIR) fluorescent dyes) such as La Jolla Blue® and IRDye® 700DX.

The present disclosure also provides methods of administering, to a subject having a tumor, a tumor-targeting virus-like particle comprising photosensitive molecules conjugated to capsid proteins, or administering, to a subject having a tumor, a tumor-targeting virus-like particle comprising about 50 to about 1000 (e.g., 50, 100, 150, 200, 250, 300, 350, 400, 450, 500, 550, 600, 650, 700, 750, 800, 850, 900, 950, or 1000) photosensitive molecules.

In some embodiments, the subject is a mammal, such as a human.

The mode of administration can be by injection, infusion, implantation, topical administration, or by any other means typically used to deliver virus-like particles. In some embodiments, hollow needles, coated needles, mini-needles or micro-needles are used, depending on the area of injection. In some embodiments, the mode of administration is by injection into the intraocular space or into the vitreous of an eye (e.g., to target ocular tumors or tumors that have metastasized to the eye).

Examples of reagents that may be used to deliver virus-like particles of the present disclosure include, without limitation, saline, $MgCl_2$, trehalose, sodium hyaluronate, polysorbate 20, polysorbate 80 or any combination of two or more of the foregoing reagents.

Photosensitive molecules of the disclosure can be activated at a suitable wavelength. In some embodiments, activation of the photosensitive molecules renders them cytotoxic or able to produce a cytotoxic molecule. Suitable wavelengths include, without limitation, ultraviolet wavelengths, visible wavelengths, infrared wavelengths and near infrared wavelengths. In some embodiments, the photosensitive molecules are activated and become cytotoxic at a wavelength of 600 nm to 800 nm, or 660 nm to 740 nm. In some embodiments, the photosensitive molecules are activated and become cytotoxic at a wavelength of about 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, 750 nm, 760 nm, 770 nm, 780 nm, 790 nm or 800 nm. In some embodiments, the photosensitive molecules are activated at a wavelength of less than 600 nm or more than 800 nm. Suitable wavelengths for photosensitive molecule activation will depend on the particular molecule used.

The photosensitive molecules of the disclosure, depending on the type of molecule, can be activated by infrared, near-infrared or ultraviolet light. For example, an infrared, near-infrared or ultraviolet laser may be used, in some embodiments, to activate the photosensitive molecules of VLP conjugates. The energy delivered by the laser may range from about 5 J to about 100 J, about 5 Joules (J) to about 50 J, or about 8 J to about 36 J. In some embodiments, the energy delivered by the laser is 8 J, 9 J, 10 J, 11 J, 12 J, 13 J. 14 J, 15 J, 16 J, 17 J, 18 J, 19 J, 20 J, 21 J. 22 J, 23 J, 24 J. 25 J, 26 J, 27 J, 28 J, 29 J, 30 J, 31 J, 32 J, 33 J, 34 J, 35 J, 36 J, 37 J, 38 J, 39 J, 40 J. 41 J, 42 J, 43 J. 44 J, 45 J, 46 J. 47 J, 48 J, 49 J. 50 J, 51 J, 52 J, 53 J, 54 J, 55 J, 56 J, 57 J, 58 J, 59 J, 60 J, 61 J, 62 J, 63 J, 64 J, 65 J, 66 J, 67 J. 68 J, 69 J, 70 J. 71 J, 72 J, 73 J, 74 J or 75 J. In some embodiments, the energy delivered by the laser is 10 J, 20 J, 30 J, 40 J, 50 J, 60 J, 70 J, 80 J. 90 J or 100 J.

A light or laser may be applied to the photosensitive molecules (or photosensitive VLPs) from about 5 seconds to about 5 minutes. For example, in some embodiments, the light or laser is applied to the photosensitive molecules for 5, 10, 15, 20, 25, 30, 35, 40, 45 50 or 55 seconds to activate the molecules. In some embodiments, the laser is applied to the photosensitive molecules for 1, 1.5, 2, 2.5, 3, 3.5, 4, 4.5 or 5 minutes, or more. It should be understood that the length of time a light or laser is applied to a photosensitive molecule can vary depending, for example, on the energy (e.g., wattage) of the later. For example, lasers with a lower wattage may be applied to a photosensitive molecule for a longer period of time in order to activate the molecule.

A light or laser may be applied to the photosensitive molecules (or VLP conjugates) about 30 minutes to about 48 hours after administering the VLP conjugates. For example, in some embodiments, the light or laser is applied to the photosensitive molecules 30, 35, 40, 45, 50 or 55 minutes after administering the VLP conjugates. In some embodiments, the light or laser is applied to the photosensitive molecules 1, 2, 3, 4, 5, 6, 7, 8, 9, 10, 11, 12, 13, 14, 15, 16, 17, 18, 19, 20, 21, 22, 23 or 24 hours after administering the VLP conjugates. In some embodiments, the light or laser is applied to the photosensitive molecules 36 or 48 hours after administering the VLP conjugates.

The light or laser may be applied directly to the site of the tumor. For example, VLP conjugates targeting ocular tumors may be activated by illuminating the eye.

Any type of tumor can be targeting in accordance with the present disclosure. Examples of tumors include, without limitation, those located in the eye, lung, pleura, liver, pancreas, stomach, esophagus, colon, breast, ovary, prostate, brain, meninges, testis, kidneys, bladder, head, neck, cervix, larynx and/or skin.

In some embodiments, the tumor is an ocular tumor. The ocular tumor may be located in the vitreous, choroidal space, iris, ciliary body, sclera, fovea, retina, optic disk or optic nerve.

The tumor, in some embodiments, is cancerous or malignant. In some embodiments, the tumor is metastatic. Other tumors may also be targeted. For example, the present application provides methods and compositions for targeting cervical cancer cells, ovarian cancer cells, melanoma cancer cells, lung cancer cells, head and/or neck cancer cells, and bladder cancer cells.

Compositions

The virus-like particles (viral-like nanoparticles) of the present disclosure are, in some embodiments, photosensitive molecule-conjugated viral-like nanoparticles. The viral-like nanoparticles contain one or two types of capsid proteins from papilloma virus. In some embodiments, the capsid proteins are modified. Capsid proteins typically self-assemble into "empty" proto-capsids approximately 55 nm in diameter (e.g., spherical-like particles containing a hollow core). After maturation of the proto-capsids to form viral-like nanoparticles (virus-like particles), viral-like nanoparticles are then chemically conjugated with a photosensitive molecule (e.g., IR700 dye such as IRDye® 700DX, an infrared dye manufactured by LI-COR®).

In some embodiments, the photosensitive viral-like nanoparticles are provided in a sterile, solution (e.g., 1 or 2 ml) in single use vials (e.g., borosilicate glass vials). In some embodiments, the photosensitive viral-like nanoparticles are provided in a sterile solution of water that optionally includes NaCl, KCl, $Na_2HPO_4 \cdot 2H_2P$, $KH_2PO_4$, or any combination of two or more of the foregoing. In some embodiments, NaCl may be present in the solution at a concentration of 400 to 600 mMol (e.g., 500 mMol). In some embodiments, KCl may be present in the solution at a concentration of 2 to 6 mMol (e.g., 2.7 mMol). In some embodiments, $Na/HPO_4 \cdot 2H_2O$ may be present in the solution at a concentration of 5 to 15 mMol (e.g., 10 mMol). In some embodiments, $KH_2PO_4$ may be present in the solution at a concentration of 1 to 3 mMol (e.g., 2 mMol).

It some embodiments, photosensitive viral-like nanoparticles are diluted and administered intra-ocularly using a sterile syringe and needle commonly used in ophthalmic procedures. The present disclosure also provides other routes of administration and administration to other tumors and/or metastases, as described elsewhere herein.

In some embodiments, each viral-like nanoparticle comprises 12-72 capsomers with each capsomere containing 5 molecules of L1 capsid protein (e.g., 55-56 kD each) and 1 molecule of L2 capsid protein (e.g., 52 kD each). In some embodiments, each viral-like nanoparticle comprises 12-72 capsomers with each capsomere containing only L1 capsid proteins (e.g., 5 molecules of L1 protein per capsomere).

In some embodiments, each viral-like nanoparticle is chemically conjugated (e.g., via an amide bond) with 10 to 1000 molecules (e.g., 500 molecules) of photosensitive molecule (IR700 dye such as IRDye® 700DX) to at least one amino acid (e.g., lysine amino acid) of the protein.

Methods of Producing Virus-Like Particles

Figure 23A:
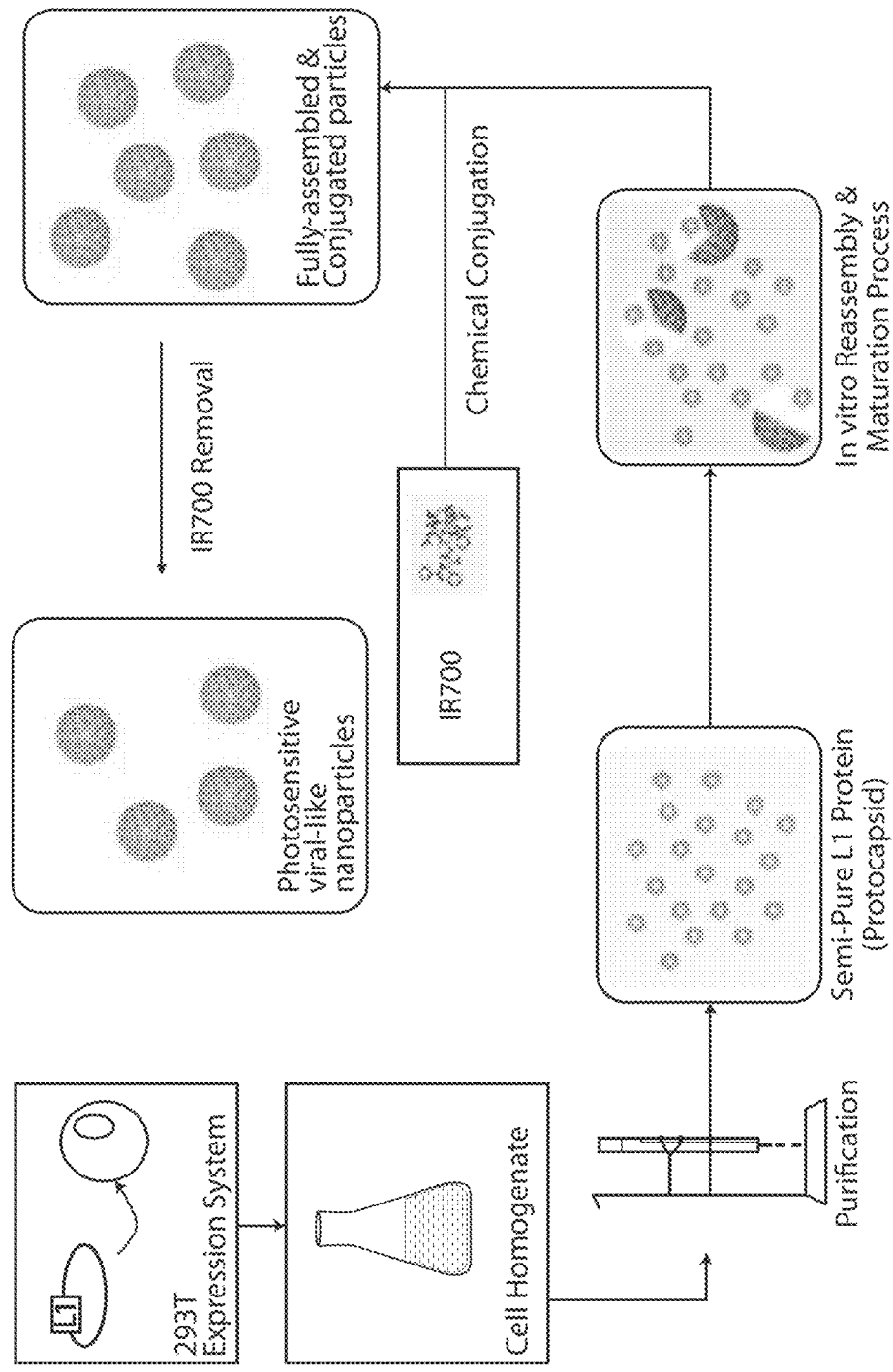
FIGS. 23A and 23B depict examples of a photosensitive viral-like nanoparticle production process of the present disclosure (e.g., as described in Example 20).
Figure 23B:
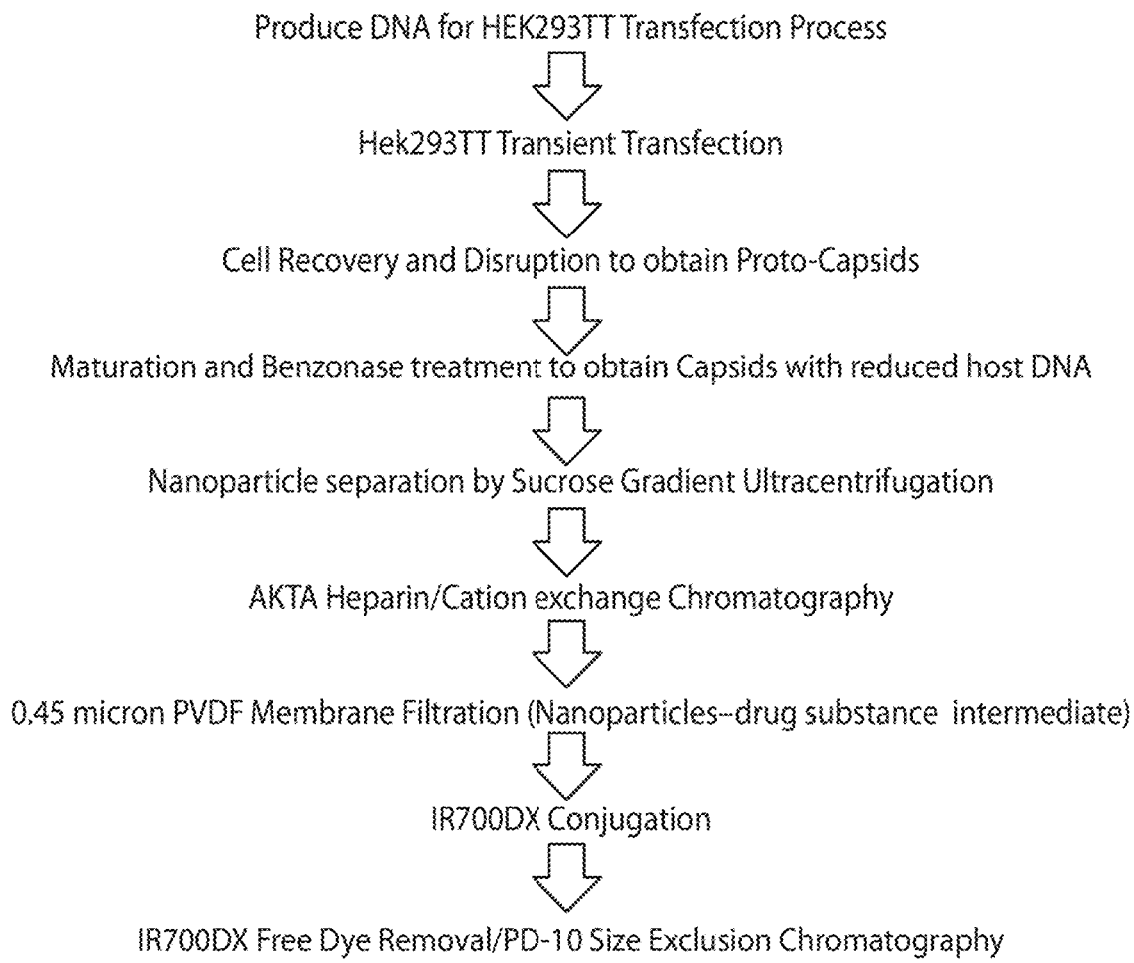

To produce photosensitive viral-like nanoparticles of the present disclosure, mammalian cells, such as 293T cells (e.g., HEK293F cells) may be grown (e.g., in suspension culture) and transiently transfected with a nucleic acid (e.g., bi-cistronic plasmid DNA) encoding BPV or HPV L1 (or L1 and L2) capsid proteins. This induces the formation of proto-capsids (e.g., as described in Buck et. al. Current Protocols in Cell Biology 26.1.1-26.1.19, December 2007). Following cell mass recovery and disruption, the proto-capsids may be subjected to host DNA clearance with benzonase treatment and a subsequent maturation process in vitro to form stable viral-like nanoparticles. Following purification, the viral-like nanoparticles may be chemically conjugated with photosensitive molecules (e.g., IR700 NHS ester) to produce the photosensitive viral-like nanoparticles. FIG. 23 shows a schematic representation of an example of a production process provided herein.

Thus, in some aspects, provided herein are methods of producing photosensitive molecules, comprising (a) transiently transfecting cells with a nucleic acid that encodes one or more capsid proteins, thereby forming proto-capsids, (b) collecting the proto-capsids and subjecting the proto-capsids to a maturation process in vitro, thereby forming stable viral-like nanoparticles, and (c) chemically conjugating the viral-like nanoparticles to 50 to 1000 photosensitive molecules. In some embodiments, the viral-like nanoparticles are conjugated to 500 photosensitive molecules. In some embodiments, the viral-like nanoparticles are conjugated to photosensitive molecules through an amide bond (e.g., by reacting an ester group of a photosensitive molecule with an amine group of an amino acid the capsid protein of a viral-like nanoparticle).

EXAMPLES

Example 1—Conjugation of IRDye® 700DX

Figure 10A:
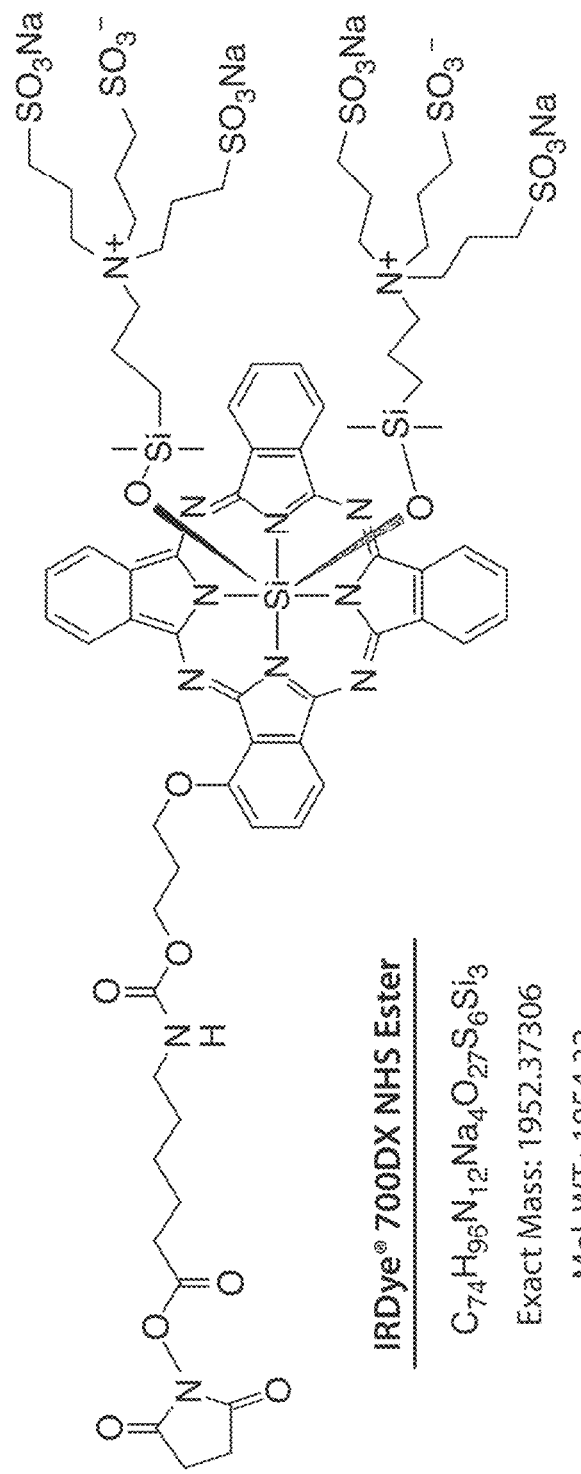
FIG. 10A shows a chemical structure of IR Dye 700DX NHS ester.

The procedure of chemical conjugation of VLPs (e.g., viral-like nanoparticles containing a combination of variant HPV16/31 L1 proteins and HPV L2 proteins) to a photosensitive molecule (e.g., IRDye® 700DX) is as follows. Typically, solutions of VLPs were maintained at a concentration of 1 mg/ml in PBS, pH=7.2 and 0.3 to 0.5 M NaCl. The IR700 (e.g., IRDye® 700DX) molecules were supplied from the manufacturer as dry NHS (N-Hydroxysuccinimide) esters (NHS-esters react with amine groups on proteins to form covalent amide bonds) (FIG. 10A). Available amine groups on proteins are the amino terminus of the protein or the ε-amino group on the amino acid (e.g., lysine). The dry solid IR700-NHS ester was dissolved in DMSO at a concentration of 5 mg/ml and stored frozen. Typically, different ratios of VLP:dye were achieved by mixing different amounts of IR700-NHS to a fixed amount of VLP, usually 1 ml of 1 mg/ml solution in PBS. The typical ratios and the amounts of IR700-NHS are listed in the following table:

TABLE 1

| Ratio of IR700-NHS:VLP | Mass of IR700-NHS for 1 mg of VLP | Volume of IR700-NHS solution for 1 mg of VLP |
|---|---|---|
| 200:1 | 16 µg | 3.2 µl |
| 500:1 | 40 µg | 8 µl |
| 1000:1 | 80 µg | 16 µl |

To make a 200:1 ratio, 1 ml of VLP at 1 mg/ml in PBS was mixed with 3.2 µl of the IR700-NHS ester solution. These reactions were run for 2-4 hours at room temperature. Following the completion of the reaction, the VLPs were purified by heparin affinity column chromatography to separate the unbound IR700-NHS from the newly formed VLP-IR700 conjugate (also referred to as a photosensitive VLP).

Example 2—Conjugation of Visudyne®

Figure 10B:
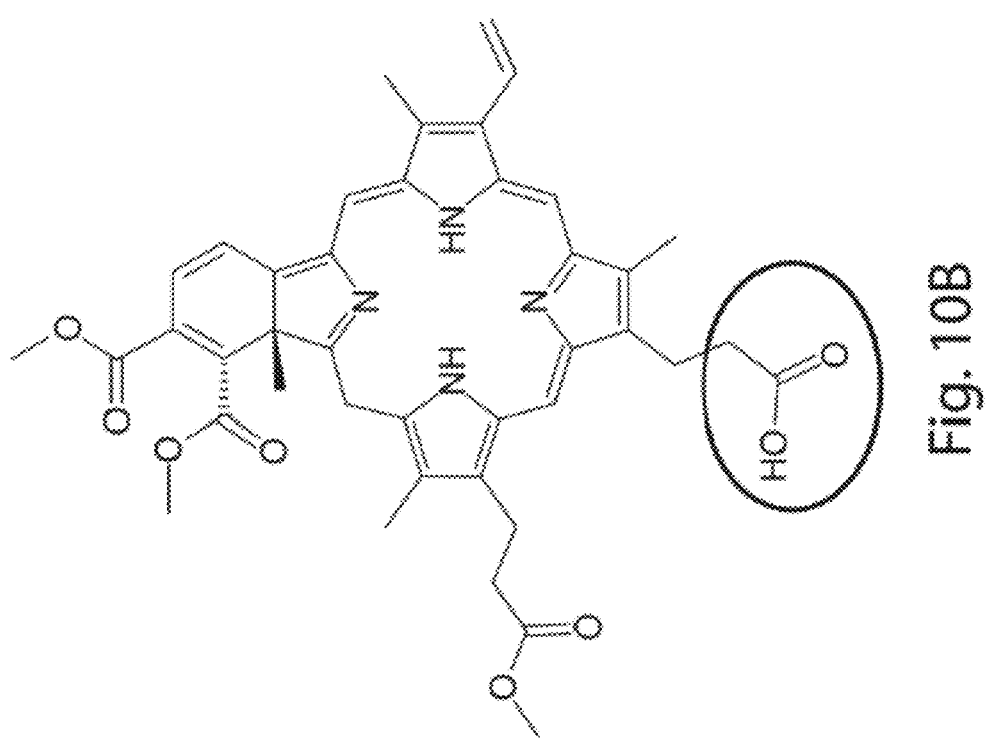
FIG. 10B shows a chemical structure of Visudyne® with a reactive carboxyl group circled.
Figure 11:
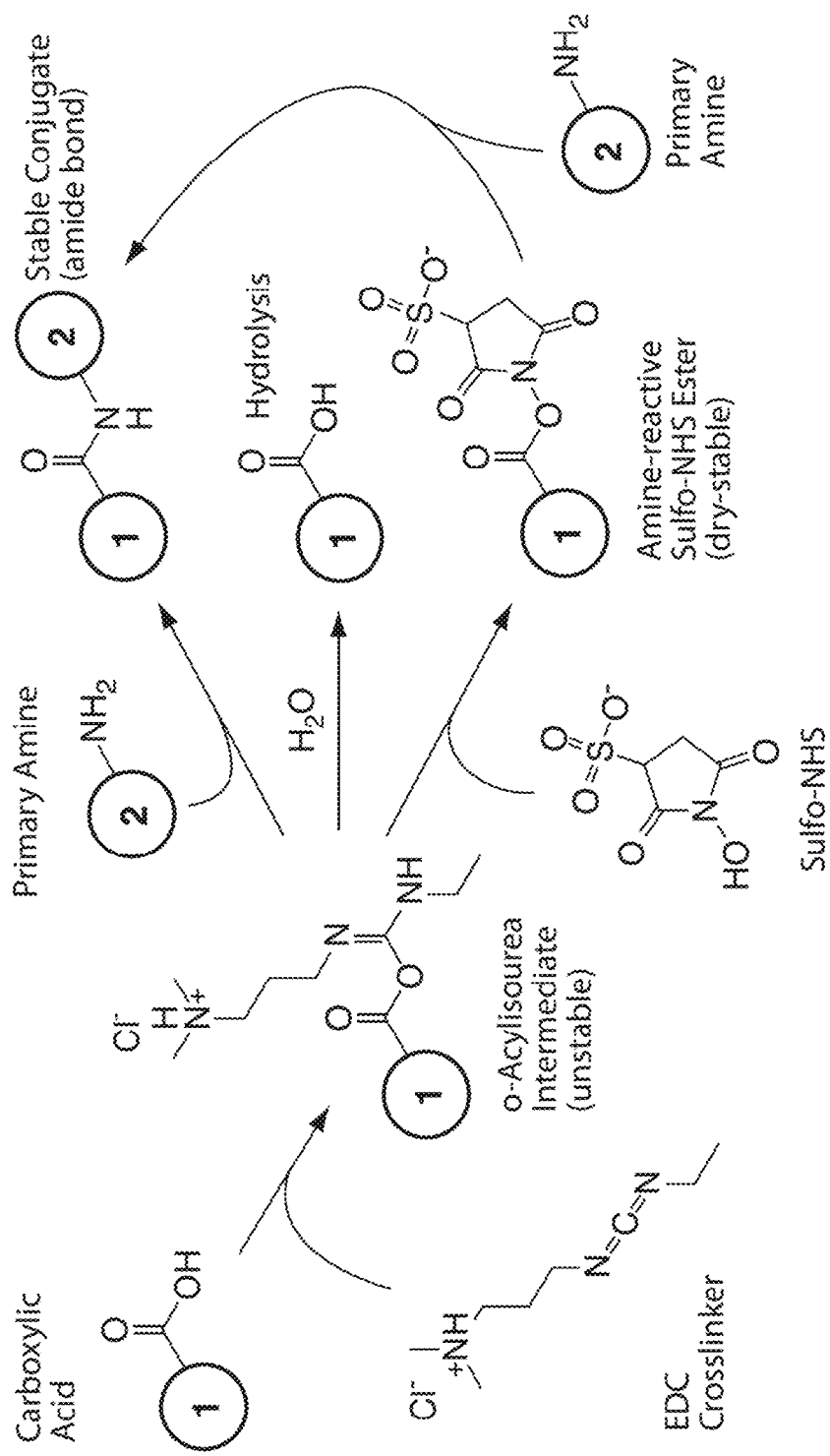
FIG. 11 shows a reaction scheme involving (1-ethyl-3-(3-dimethylaminopropyl) carbodiimide hydrochloride) (EDC) and sulfo-N-Hydroxysuccinimide (sulfo-NHS) mediated linking of Visudyne® and VLP. In this scheme, ① represents Visudyne® and ② represents VLP. Note that there are 2 routes to the desired end product. The presence of sulfo-NHS tends to stabilize the reaction and enhances the production of the desired product.

The conjugation of Visudyne® to the VLPs followed a slightly different protocol relative to the IR700-NHS. Visudyne® molecules required functionalization to NHS, prior to conjugation to VLPs. This functionalization was achieved through the use of EDC (1-ethyl-3-(-3-dimethylaminopropyl) carbodiimide hydrochloride). EDC was used to functionalize molecules that have a free carboxylic acid molecule, such as Visudyne® (see FIG. 10B; circled), and in the presence of sulfo-NHS effectively transfer the NHS moiety to this agent. This reaction scheme is outlined in FIG. 11. Briefly, approximately 2 mM of EDC and a 2× molar excess of sulfo-NHS was reacted with varying amounts of Visudyne®. After 15 minutes at room temperature, the reactions were stopped with the addition of 2-mercaptoethanol to a final concentration of 20 mM. This reaction mixture was added to 1 mg of VLPs at a concentration of 1 mg/ml in PBS, pH=7.2+0.3–0.5 M NaCl and incubated for 2-4 hours at room temperature. Finally, the unreacted components were separated from VLP-conjugates by heparin affinity column chromatography.

Figure 3:
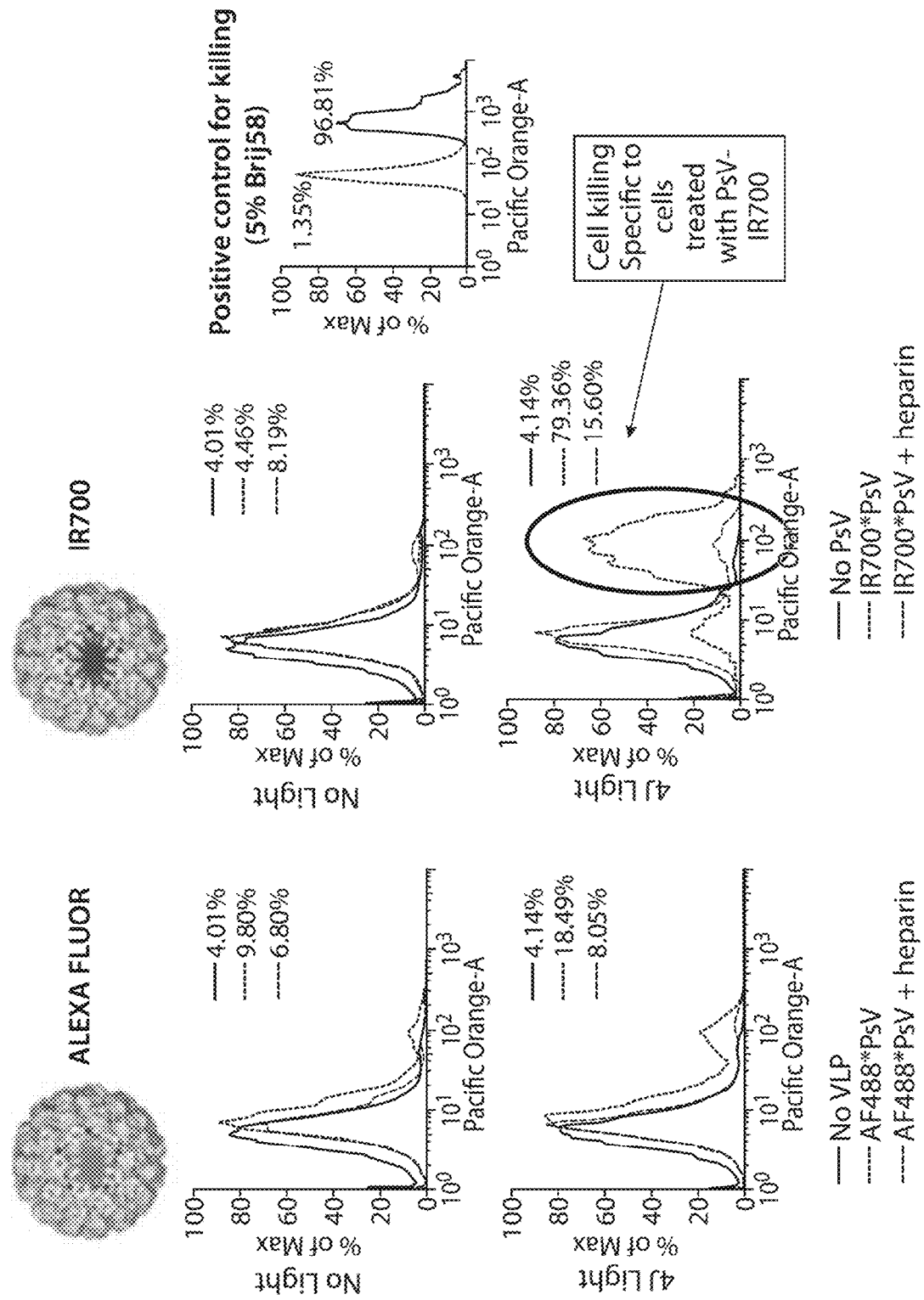
FIG. 3 shows a graph demonstrating that specificity of VLP binding to cells is mediated by heparan sulfate proteoglycan (HSPG) interactions and is inhibited by heparin. It further shows specific killing of tumor cells only when the photosensitive VLPs are bound to the cell and the cells subjected in infrared irradiation.

Example 3—VLP Binding Specificity is Mediated by HSPG and Inhibited by Heparin SK-OV-3 cells in suspension were treated under the following conditions: no VLP (e.g., viral-like nanoparticles containing a combination of variant HPV16/31 L1 proteins and HPV L2 proteins), VLP conjugated to either Alexa Fluor® 488 (FIG. 3, "AF488*PsV") or IR700 (FIG. 3, "IR700*PsV"), or the same VLP conjugates incubated in the presence of HSPG. Following incubation, these cultures were subjected to 4 joules of 690 mm near infrared light. A parallel set of non-light irradiated cells acted as a control. Following irradiation, the cultures were assessed for the extent of cell death. FIG. 3 shows that the only condition under which there was substantial cell killing was cell exposure to IR700*PsV and 4 joules of light. Similar cell death was not observed with exposure to AF488*PsV, revealing that cell death is specific to the IR700 dye conjugates. Moreover, cell death is almost completely abrogated in the presence of HSPG, revealing that VLP binding to the cell is critical to IR700-mediated cell death.

Example 4—Cell Death Depends on Infrared Radiation and the Amount of VLP and IR700

Figure 4:
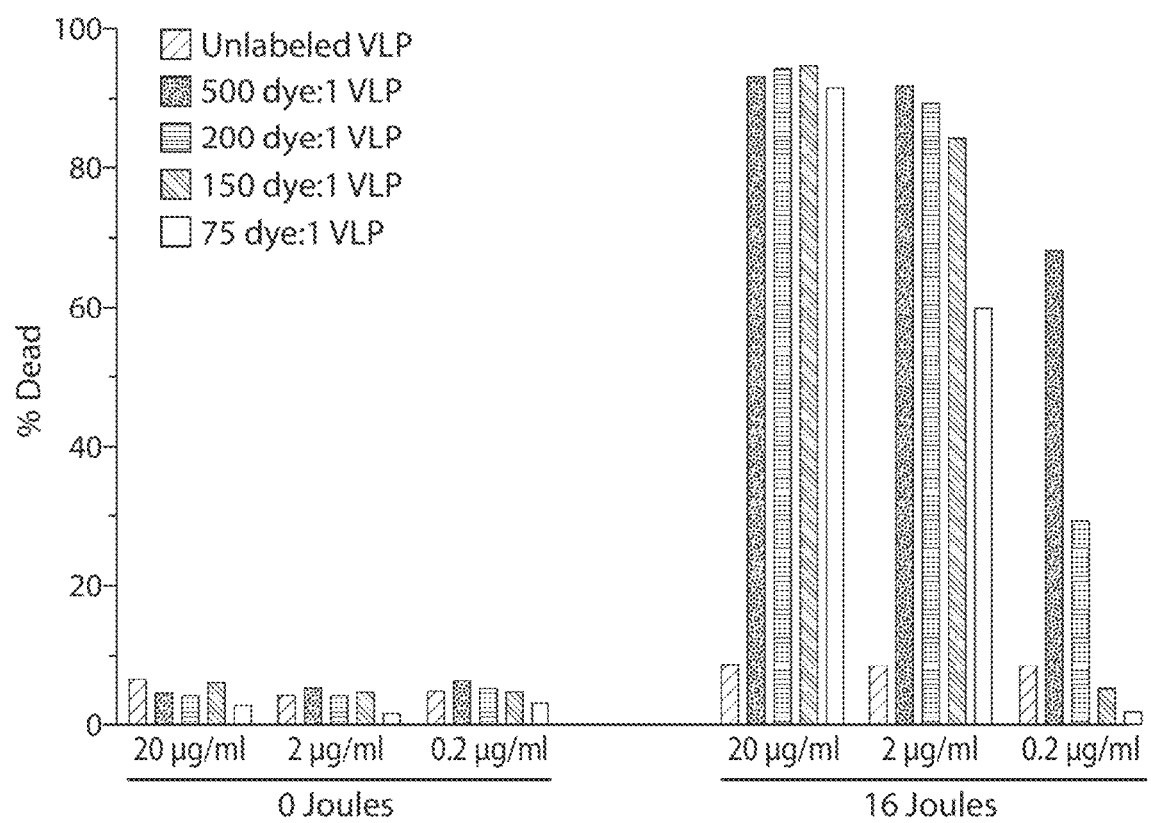
FIG. 4 shows a graph demonstrating that cell death depends on the dose of infrared radiation and the amount of the VLP and photosensitive molecule (e.g., dye) delivered.

SK-OV-3 cells in suspension were treated with differing concentrations of VLP (e.g., viral-like nanoparticles containing a combination of variant HPV16/31 L1 proteins and HPV L2 proteins) had been conjugated with differing amounts of IR700 dye (e.g., IRDye® 700DX). VLP without conjugation to IR700 dye was used as a control. Following incubation, these cultures were subjected to 0 or 16 joules of 690 nm near-infrared light. Following the light treatment, the extent of cell death was assessed. FIG. 4 shows that cell death is dependent on both the presence of IR700 dye and light treatment. This is supported by the observation that cell death depends on both VLP concentration and the IR700 dye conjugation ratio.

Example 5—In Vitro Cell Death of SKOV-3 Cells Upon Irradiation Following Treatment with VLPs Conjugated to IR700

Figure 5:
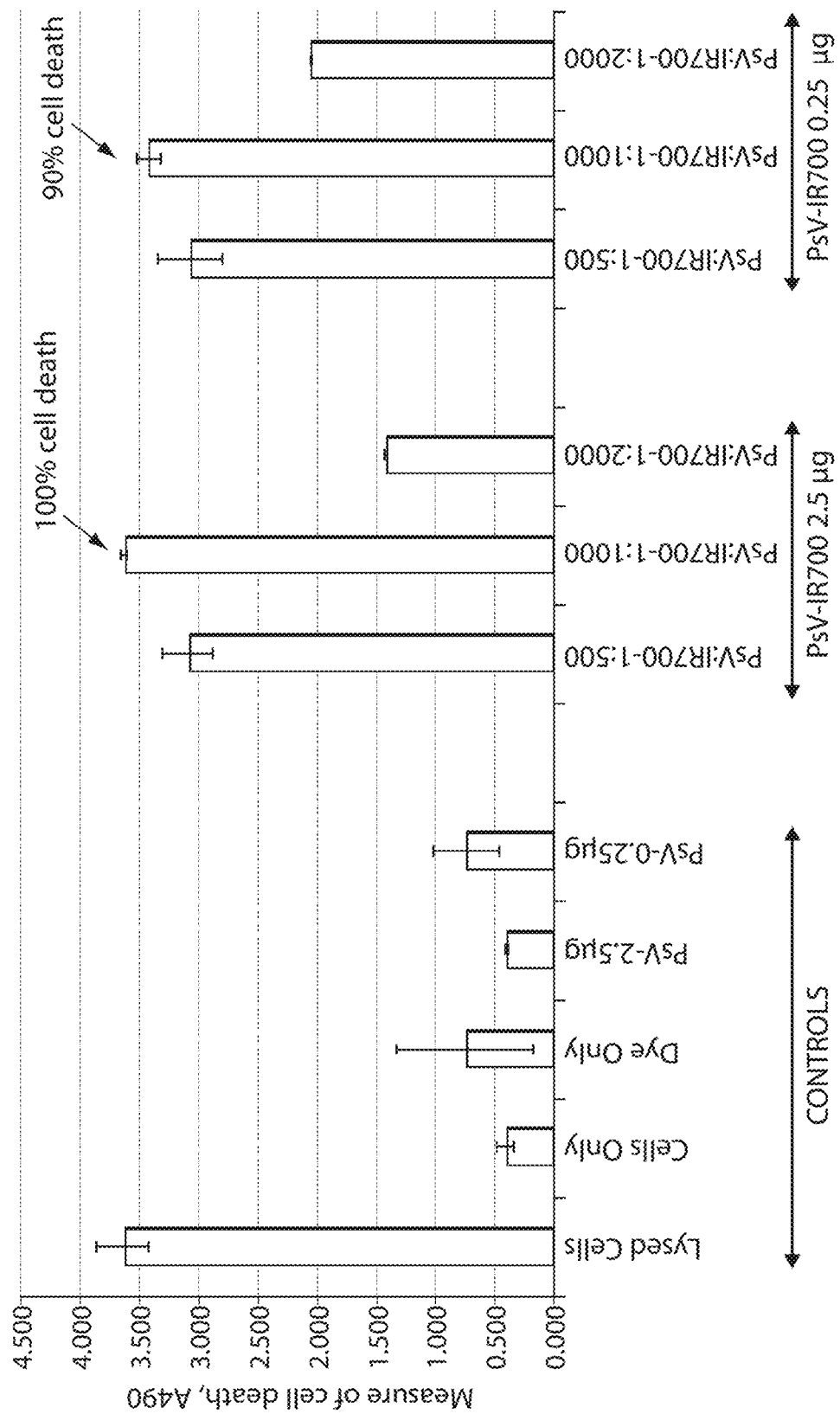
FIG. 5 shows a graph demonstrating in vitro ovarian cancer cell (SKOV-3) death upon irradiation with VLPs (designated NV in the figure) conjugated to IR700.

SKOV-3 ovarian cancer cells were plated on a 24-well plate and treated with two different concentrations of photosensitive VLP particles (e.g., viral-like nanoparticles containing a combination of variant HPV16/31 L1 proteins and HPV L2 proteins conjugated to IR700 dye), 2.5 μg (red) and 0.25 μg (blue), for 1 h at 37° C. Upon binding, the cells were washed, followed by treatment with 4 J of light. Cell death was determined upon enzymatic estimation of LDH release (determined by measuring absorbance at 490 nm). Three different molar ratios of VLP:IR700 conjugation were tested: 1:500, 1:1000 and 1:2000, respectively. FIG. 5 shows that maximum efficacy of cell death was observed at a 1:1000 ratio of VLP:IR700 ("PsV:IR700") for both concentrations tested. Detergent-mediated cell lysis was used as a positive control.

Example 6—Structural Evaluation of IR700-PsV Complexes

Figure 6A:
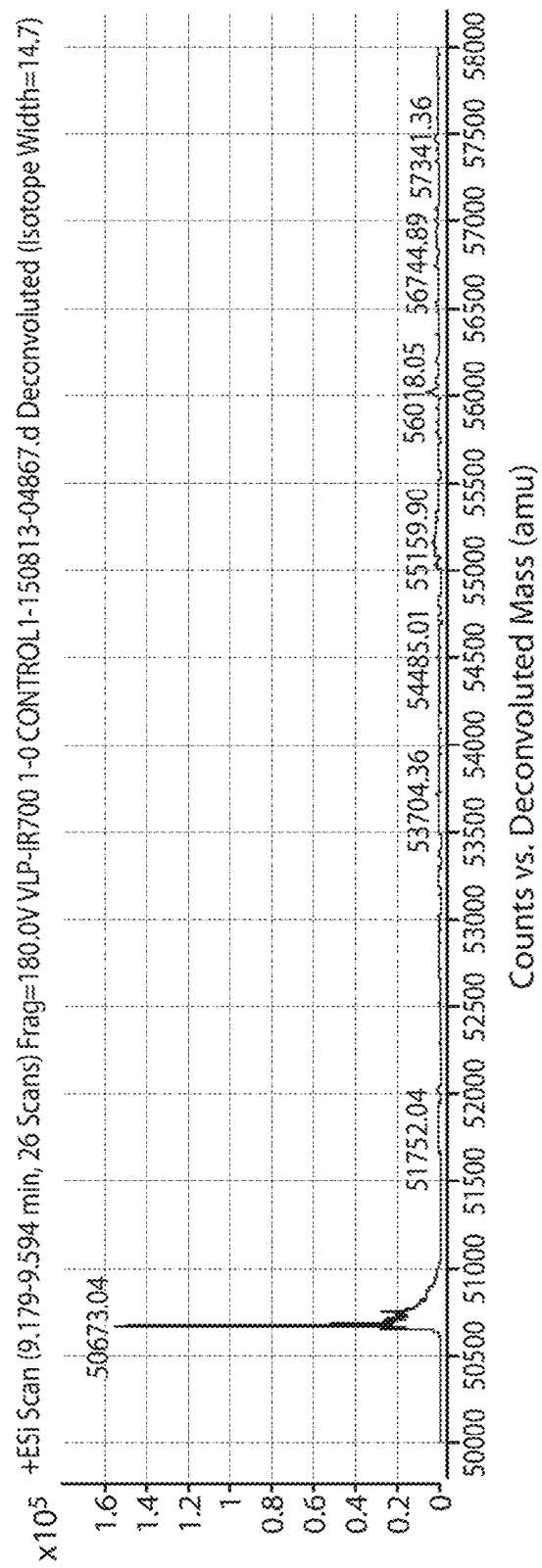
FIG. 6A shows an electrospray ionization-time-of-flight (ESI-TOF) analysis of control VLPs.
Figure 6B:
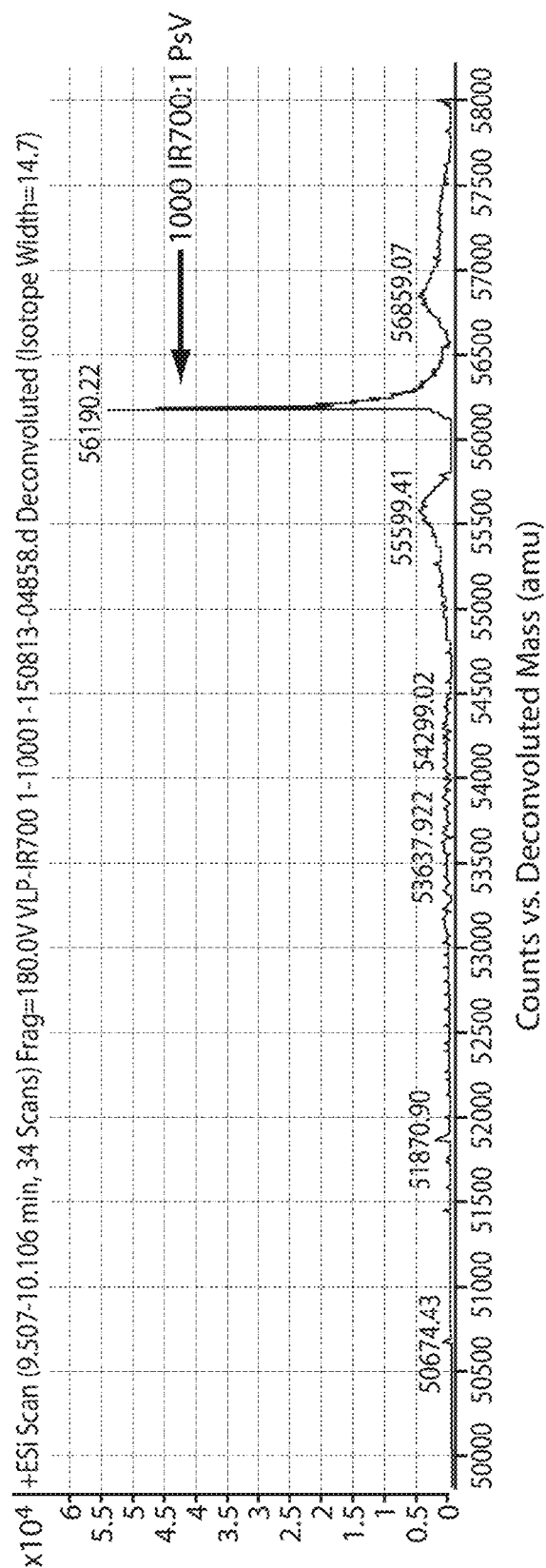
FIG. 6B shows an ESI-TOF analysis of VLPs (designated PsV in the figure) conjugated to 1000 molecules of IR700.

FIG. 6 shows an ESI-TOF analysis of control VLPs (PsV) (A) and IR700-conjugated VLPs (PsVs) (B). In FIG. 6B, the reaction was set up to achieve conjugation of each VLP (PsV) molecule with 1000 molecules of IR700. The signal spikes in the ESI-TOF scans correspond to the VLP L1 protein. A shift of 5517 amu was observed in conjugated samples relative to control samples, which conjugated samples correspond to an average of 3 conjugated IR700 molecules (1840 amu) per L1 protein or about 1000 molecules of IR700 per VLP (typically, there are 360 L1 per VLP).

Example 7—Agent Binding Determines Extent of Cell Death in an Ocular Melanoma Cell Line Ocular melanoma cell line (92.1; HER2⁻) in suspension were exposed to varying dilutions of either Herceptin® antibody conjugated to IR700 dye (e.g., IRDye® 700DX) or VLPs (e.g., viral-like nanoparticles containing a combination of variant HPV16/31 L1 proteins and HPV L2 proteins) conjugated to IR700 dye. Parallel cultures were then assessed for agent binding (FIG. 7C) or cell death in the absence (FIG. 7B) or presence (FIG. 7A) of 16 joules of 690 nm near-infrared light. FIG. 7C shows concentration-dependent VLP binding to the 92.1 ocular melanoma cells, while Herceptin® antibody binding is essentially absent. FIG. 7B shows that, in the absence of light, there is no cell death. FIG. 7A shows concentration-dependent cell death only in the photosensitive VLP-treated cells.

Example 8—Agent Binding Determines Extent of Cell Death in an Ovarian Cancer Cell Line SK-OV-3 cells (HER2⁻) in suspension were exposed to varying dilutions of either Herceptin® antibodies or VLPs particles (e.g., viral-like nanoparticles containing a combination of variant HPV16/31 L1 proteins and HPV L2 proteins) conjugated to IR700 dye (e.g., IRDye® 700DX). Parallel cultures were then assessed for Herceptin® or VLP binding (FIG. 8C) or cell death in the absence (FIG. 8B) or presence (FIG. 8A) of 16 joules of 690 nm near-infrared light. FIG. 8C shows that VLP binding is saturated in SK-OV-3 cells. Herceptin® binding is also concentration dependent, but to a lesser degree relative to the VLPs. FIG. 8B shows that, in the absence of light, there is no cell death. FIG. 8A shows concentration dependent cell death under both conditions, but similar to binding, the response is saturated with VLPs while there appears to be a concentration-dependent increase in cell death with Herceptin®. These data imply that the VLPs conjugated to IR700 (PsV-IR700) are more potent that the Herceptin® conjugated to IR700 (Herceptin-IR700).

Example 9—Vaccine Induced Anti-HPV16 Neutralizing Antibodies do not Block Binding of BPV*IR700 VLPs to the Ocular Melanoma Cell Line, 92.1

Figure 9:
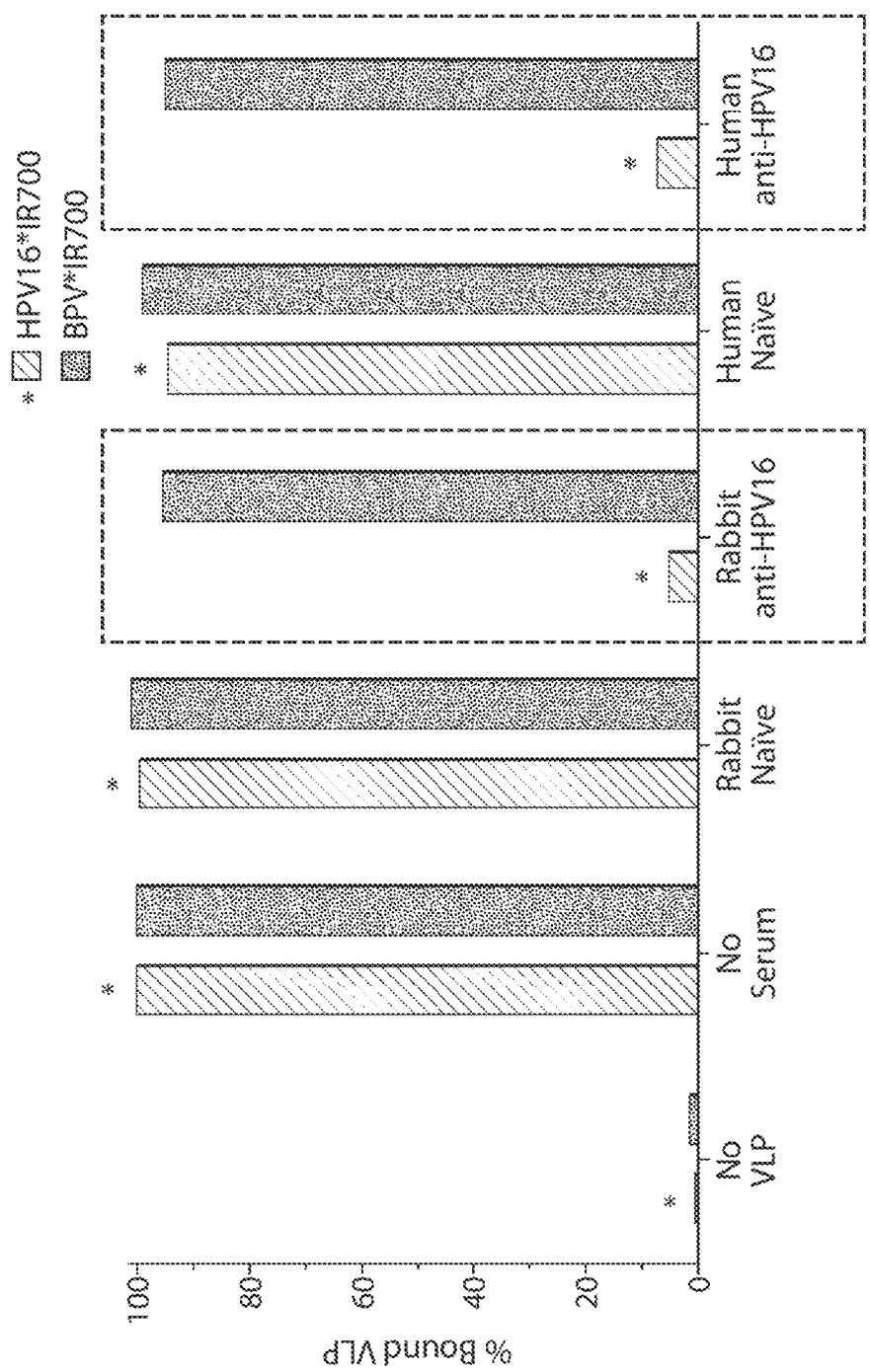
FIG. 9 shows a graph demonstrating vaccine induced anti-HPV16 neutralizing antibodies do not block binding of BPV*IR700 \TLPs to the ocular melanoma cell line, 92.1.

Samples of serum containing different antibodies were tested for the ability to inhibit photosensitive VLP particles (e.g., HPV16 VLPs or BPV VLPs) binding to the 92.1 ocular melanoma cell line. FIG. 9 shows that "no serum" or "naïve serum" conditions contain no activity that neutralizes VLP binding. Moreover, the blocking activity that was observed was specific for virus serotype. That is, only human papilloma virus-like particles conjugated to IR700 dye (HPV16-IR700) were neutralized with serum containing HPV16 antibodies. Bovine papilloma virus-like particles conjugated to IR700 (BPV-IR700) were not neutralized by serum containing HPV16-specific antibodies.

Example 10—Immunogenicity Evaluation

In a study similar to that described in Example 9, neutralizing titers were determined by serial dilution of sera containing antibodies against either HPV16 or BPV. The results described in Table 2 show that antibodies against HPV16 neutralize only HPV16. Moreover, antibodies against BPV neutralize only BPV. Thus, there is neither cross-reactivity of HVP16 antibodies against BPV nor BPV antibodies against HPV16.

TABLE 2

|  | HPV 16 | BPV |
| --- | --- | --- |
| Human anti-HPV16 | 1:57,759 | 1:24 |
| Rabbit anti-HPV16 | 1:2,876,000 | 1:21 |
| Rabbit anti-BPV | 1:83 | 1:14,332 |

Example 11—Binding Study

The goal of this Example was to assess the binding of viral-like nanoparticles containing human papilloma virus 16 (HPV16) capsid proteins, variant HPV16/31 L1 capsid proteins, and bovine papilloma virus (BPV) capsid proteins to various types of cancer cells. In addition, viral-like nanoparticles containing L1 and L2 capsid proteins, or only L1 capsid proteins, were tested to determine if there was a dependence on L2 for viral-like nanoparticle binding to cancer cells. Results of this study show that binding of BPV viral-like nanoparticles and HPV viral-like nanoparticles are comparable.

A large panel of cell lines was screened, which included: miscellaneous cell lines (e.g., 293TT, HaCaT, PAM-212 and TC-1), cervical cell lines (e.g., HeLa, SiHa, CaSki and C-33A), ovarian cell lines (e.g., MOSEC, SHIN-3, SK-OV- 3, WF-3, ES-2, A2780, OVCAR-3 and OVCAR-4), melanoma cell lines (e.g., B16F10, SKMEL-2, SKMEL-5, SKMEL-28 and UACC), ocular melanoma cell lines (e.g., 92.1. MKT-BR, OCM-1 and UW-1), lung cell lines (e.g., NCI-H23, NCT-H322M, NCI-H460 and NCI-H522), head and neck cell lines (e.g., CAL-33 (HPV−), FaDu (HPV−), HSC-3 (HPV−), SNU-1076 (HPV−), UM-SCC-47 (HPV+), UPCI-SSC-90 (HPV+) and UPCI-SCC-154 (HPV+), and bladder cell lines (e.g., 5637, J82, RT112, *SCaBER*, SVHUC, T24, UMUC-3, UMUC-5).

Prior to the experiment, viral-like nanoparticles were conjugated to AlexaFluor488 to allow for easy and direct analysis of viral-like nanoparticle binding to the cell surface. AlexaFluor488 was attached to the viral-like nanoparticle using N-Hydroxysuccinimide (NHS)-ester chemistry, which does not interfere with binding. Each of the viral-like nanoparticles was tested at a concentration of 10 µg/ml, 1 µg/ml and 0.1µ/ml.

Cells were trypsinized to remove them from the plastic surface of tissue culture plates, washed and allowed to recover for 4 hours at 37° C. in growth media on a rocking platform. The cells were then washed, counted and placed into a 96-well round bottom plate at $1\times10^5$ cells/well in phosphate buffered saline (PBS)/2% fetal bovine serum (FBS). The viral-like nanoparticles were added to the cells in a final volume of 100 µl PBS/2% FBS. Viral-like nanoparticles pre-incubated with heparin (1 mg/ml, 1 hour, 4° C.) were also added to wells as controls. The cells and viral-like nanoparticles were then incubated for 1 hour at 4° C. (in the dark), washed twice with PBS/2% FBS and fixed with 4% paraformaldehyde for 15 minutes at room temperature. Cells were finally washed again and resuspended in 200 µl PBS/2% FBS and analyzed on a BD FACS CANTO® II (BD Biosciences, San Jose, CA) using BD FACSDIVA™ (BD Biosciences, San Jose, CA) and FlowJo software.

Figure 12:
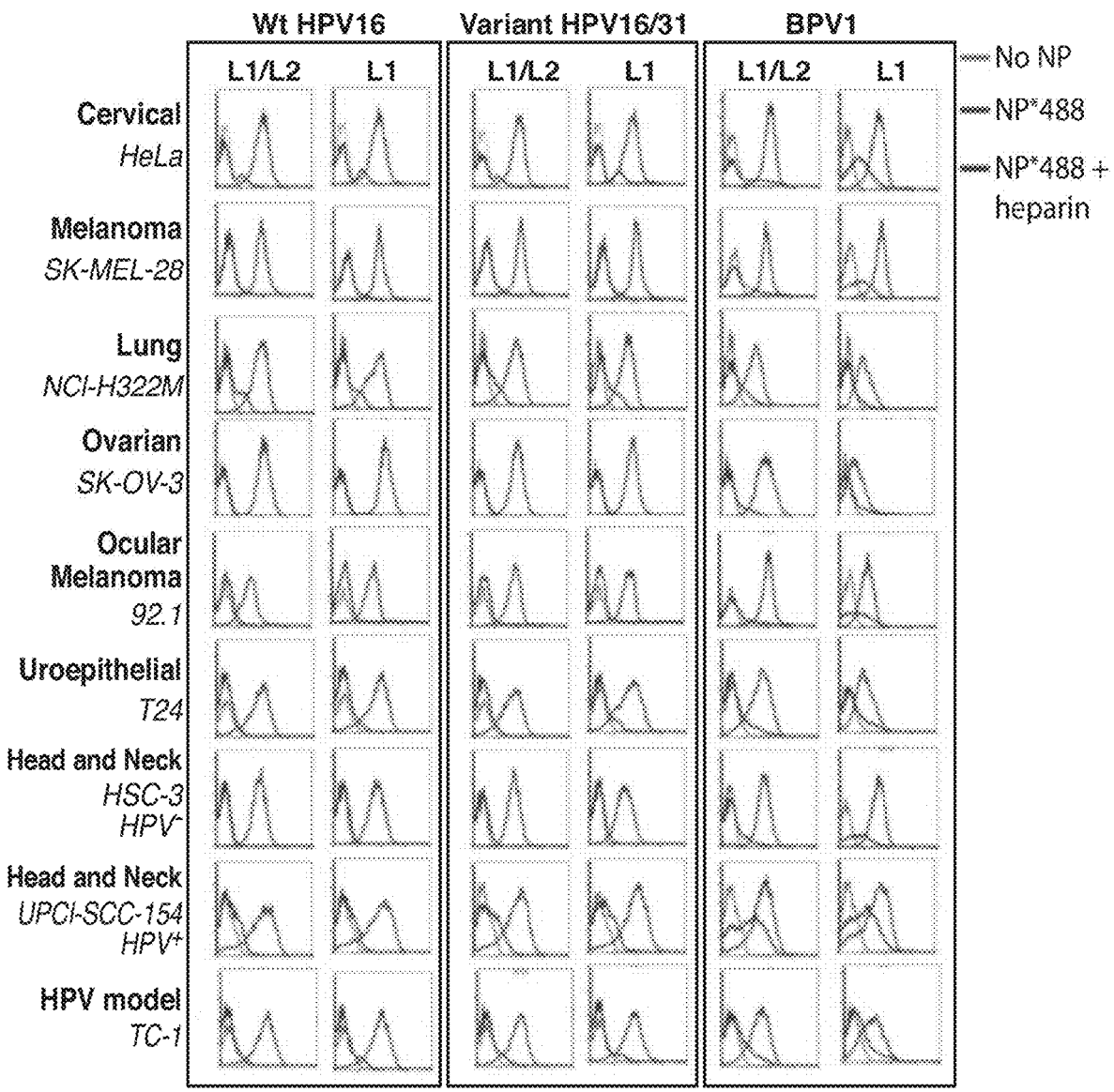
FIG. 12 shows histograms of representative samples of the HSPG-dependent binding of viral-like nanoparticles containing HPV16 capsid proteins, variant HPV16/31 capsid proteins and BPV1 capsid proteins or L1 and L2 proteins) binding to various types of cancer eel s.

Results using the TC-1, HeLa, SK-OV-3, SKMEL-28, 92.1, NCI-H322M, HSC-3, UPCI-SCC-154 and T24 cell lines are presented as histograms in FIG. 12. As evident from FIG. 12, all viral-like nanoparticles, regardless of their serotype or makeup (L1 versus L1/L2) bind to cancer cells in the binding assay. Moreover, heparin competes for binding, demonstrating that viral-like nanoparticle binding is specific and HSPG dependent.

Example 12—Biodistribution Time Course

The goal of this Example was to assess tumor localization and time course of clearance of viral-like nanoparticles following intravenous injection into tumor-hearing animals.

Purified viral-like nanoparticles were prepared by labeling viral-like nanoparticles (e.g., viral-like nanoparticles containing a combination of variant HPV16/31 L1 proteins and HPV L2) with IR700 dye (e.g., IRDye® 700DX) at a viral-like nanoparticle:dye ratio of 1:500. The photosensitive viral-like nanoparticles were purified by density gradient ultracentrifugation using OPTIPREP™ Density Gradient Medium.

Tumors were generated in albino C57Bl/6 mice by subcutaneous injection of $2\times10^5$ TC-1 cancer cells in 100 µl of PBS. After about two weeks, animals were randomized into treatment groups. Tumor-bearing animals received by intravenous injection either PBS or 200 µg of the photosensitive viral-like nanoparticles in a volume of 100 µl. Twelve or twenty-four hours following injection, the animals were euthanized. Following euthanasia, tumor tissue was harvested and imaged for fluorescence of the IR700 dye (e.g., IRDye® 700DX), indicating presence of the photosensitive viral-like nanoparticles.

Figure 13A:
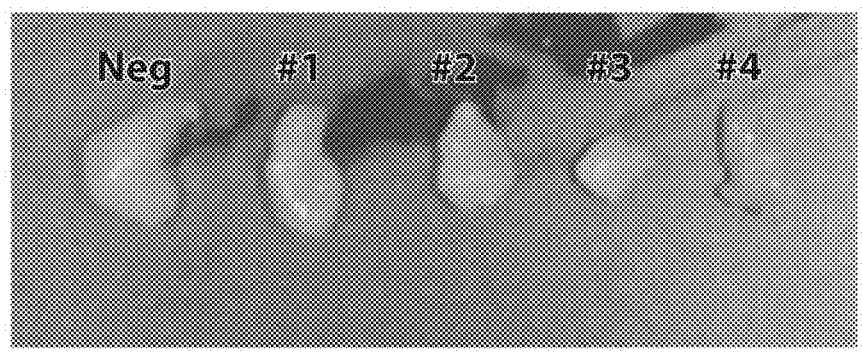
FIGS. 13A and 13B shows images of excised tumor tissue in bright field (FIG. 13A) and fluorescence (FIG. 13B) from PBS-injected negative control mice at 12 hours, photosensitive viral-like nanoparticle-injected mice at 12 hours (#3 and #4) and photosensitive viral-like nanoparticle-injected mice at 24 hours (#1 and #2) following injection.
Figure 13B:
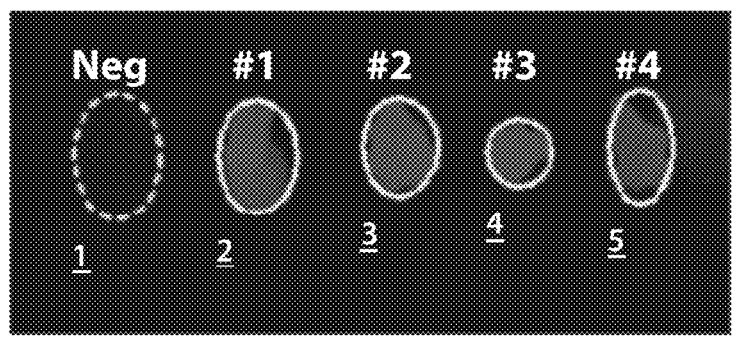
Figure 14:
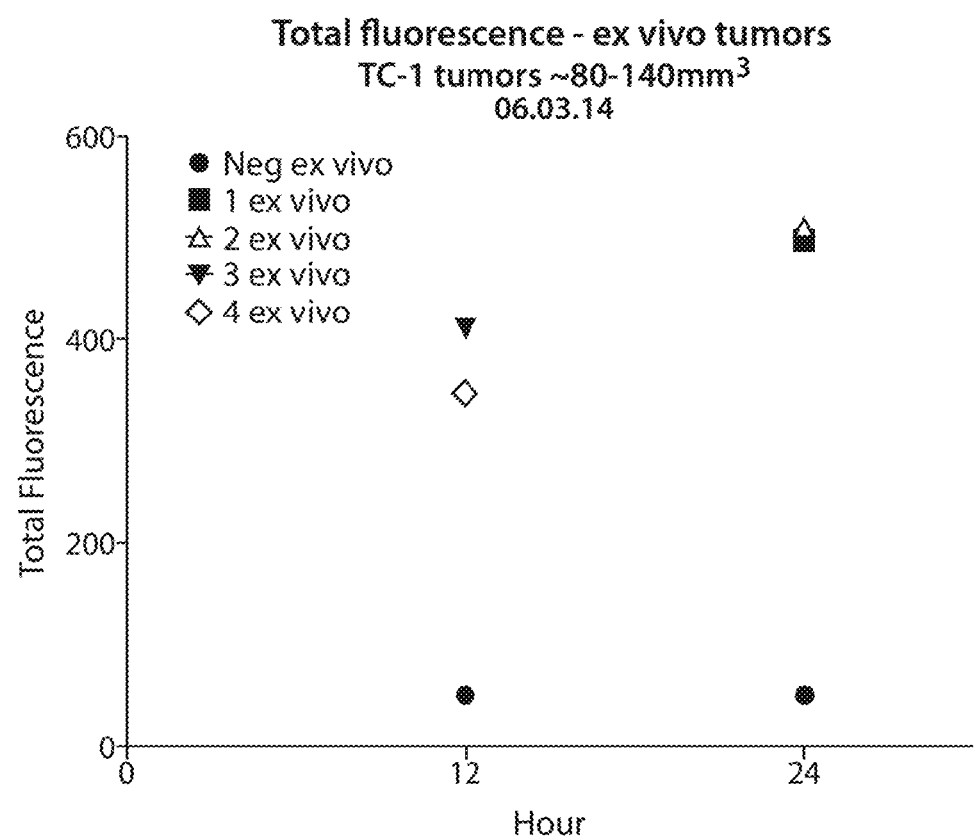
FIG. 14 shows a quantitative representation of total tumor associated viral-like nanoparticle-related fluorescence in ex vivo TC-1 tumor samples excised 0.12 and 24 hrs after intravenous injection of the VLPs (same tumors as FIG. 13)

FIG. 13B shows detectable IR700 dye (e.g., IRDye® 700DX) fluorescence in the tumor tissue obtained from both of the 12- and 24-hour time points, while fluorescence in the PBS control (12-hour time point) was not detected. The quantitative total fluorescence in the tumor tissue is plotted in the graph depicted in FIG. 14.

Example 13—Biodistribution Time Course

The goal of this Example was to assess tumor localization and time course of clearance of viral-like nanoparticles following intravenous injection into tumor-bearing animals.

Purified viral-like nanoparticles were labeled with AlexaFluor488 in lysate and purified by density gradient ultracentrifugation using OPTIPREP™ Density Gradient Medium.

Tumors were generated in albino C57Bl/6 mice by subcutaneous injection of $2\times10^5$ TC-1 cancer cells in 100 µl of PBS. After about 2 weeks, 200 µg of the photosensitive viral-like nanoparticles were delivered by intravenous injection in a volume of 100 µl. Tumors were harvested at the following time points following photosensitive viral-like nanoparticle injection: T=1, 2, 4, 8, 12, 24, 48 and 72 hours. Upon harvest, fragments of tumors were frozen for microscopic assessment. For this microscopic assessment, tissue sections were further stained. Rabbit polyclonal sera against HPV16 was used in conjunction with an AlexaFluor-488 secondary antibodies. Blood vessels were co-stained with a rat anti-CD31 antibody and an anti-rat AlexaFluor-594 secondary antibody. Nuclei where highlighted with DAPI.

Data (in situ images not shown) demonstrate the presence of the photosensitive viral-like nanoparticles at the 1-hour time point. The localization of the signal appeared to be associated within the blood vessels. The maximum level of staining appeared to occur at the 8-hour time point, and at the 8-hour time point, the photosensitive viral-like nanoparticles appeared to be diffusing from within the blood vessels to the tumor cells. Finally, at the 24-hour and 48-hour time points, there appeared to be little viral-like nanoparticle signal in the tumor.

Example 14—In Vivo Efficacy after Systemic Administration

The study presented in this Example was designed to measure tumor viability 24 hours after a single treatment. The study establishes guidelines for long-term in vivo studies.

Figure 15:
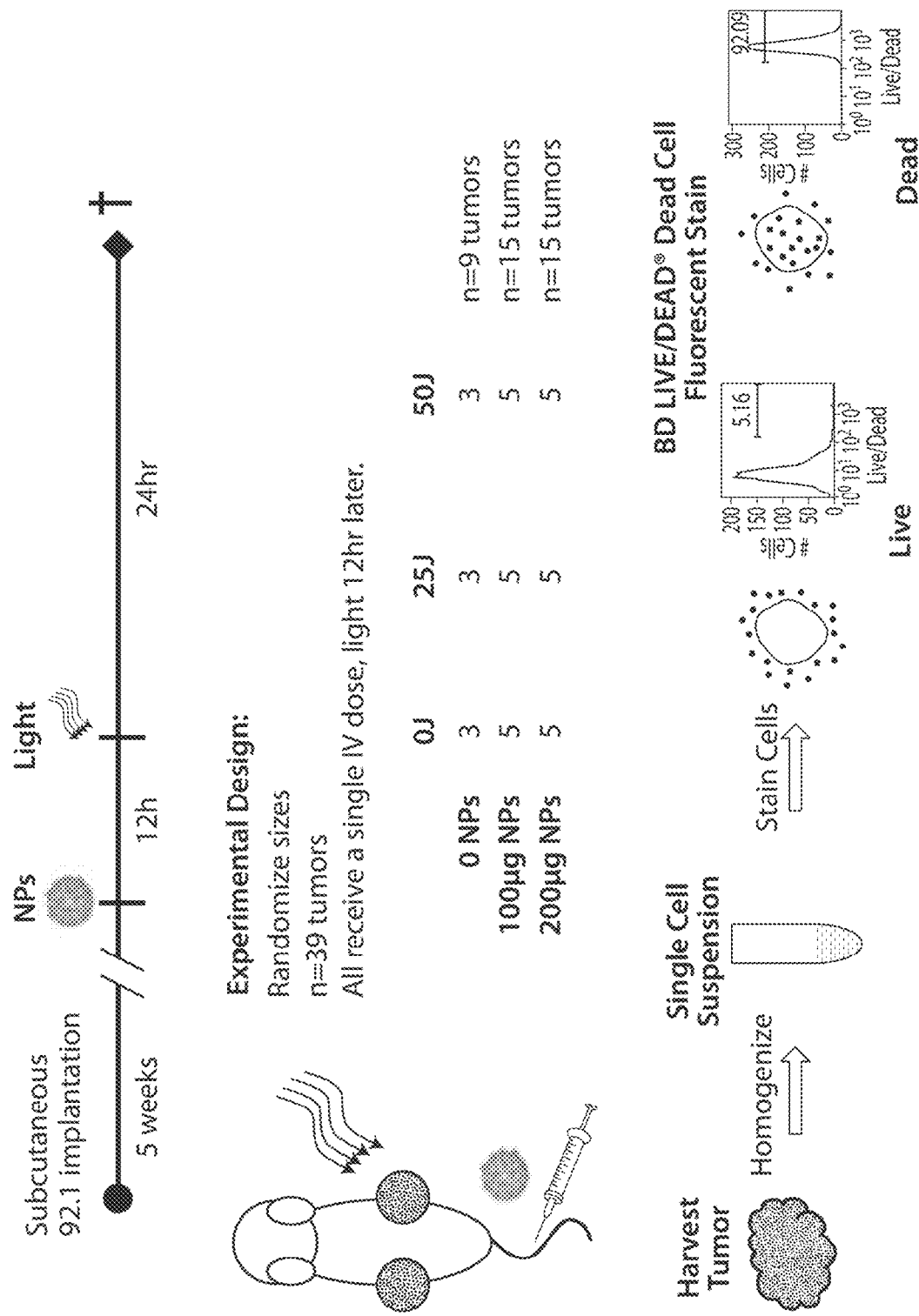
FIG. 15 shows a schematic of the experimental design for Example 14.
Figure 16A:
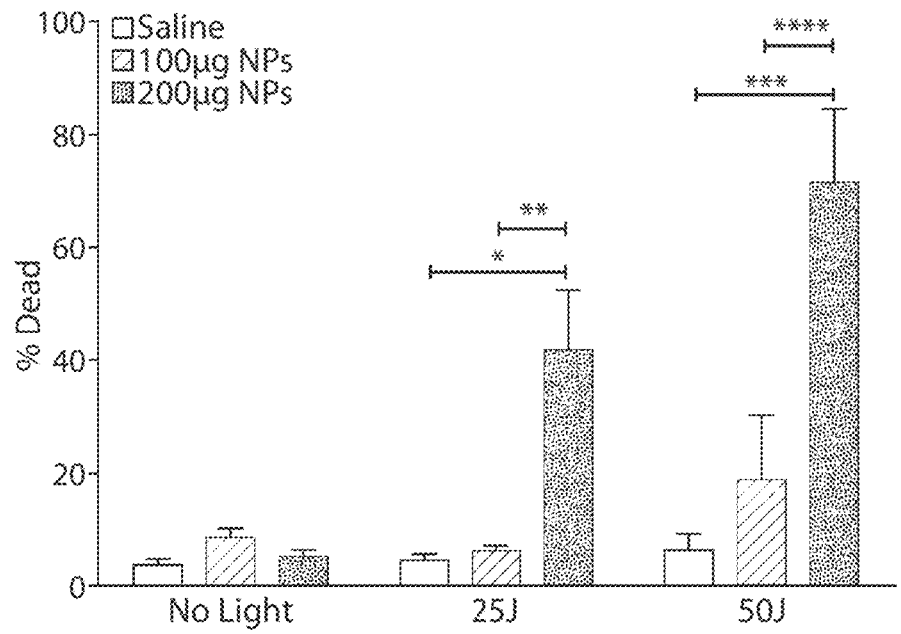
FIGS. 16A and 16B show graphs of percentage of cell death after in vivo administration of photosensitive viral-like nanoparticles (designate) NPs in the figure) and light titration on subcutaneous 92.1 ocular melanoma (OM) cells (cell viability measured 24 hours after light treatment)

Full study design is illustrated in FIG. 15. Due to the range in tumor sizes, animals were randomized such that an even distribution of large and small tumors were within each group of n=3 in the saline-treated groups and n=5 in the IR700 (e.g., IRDye® 700DX)-photosensitive viral-like nanoparticle-treated groups. Viral-like nanoparticles were administered intravenously 12 hours prior to light treatment. One hundred microgram (100 µg) and 200 µg doses were tested. Light treatment included of 25 J (62.3 s at 400 mW) or 50 J (125 s at 400 mW). After 24 hours, tumors were harvested and processed using collagenase and DNase to generate a single cell suspension. BD LIVE/DEAD® yellow stain was then applied, and cells were placed through a FACS CANTO™ II. Data are reported as percentage of dead cells as indicated by a shift in fluorescence in the Pacific orange channel (FIG. 16A).

Figure 16B:
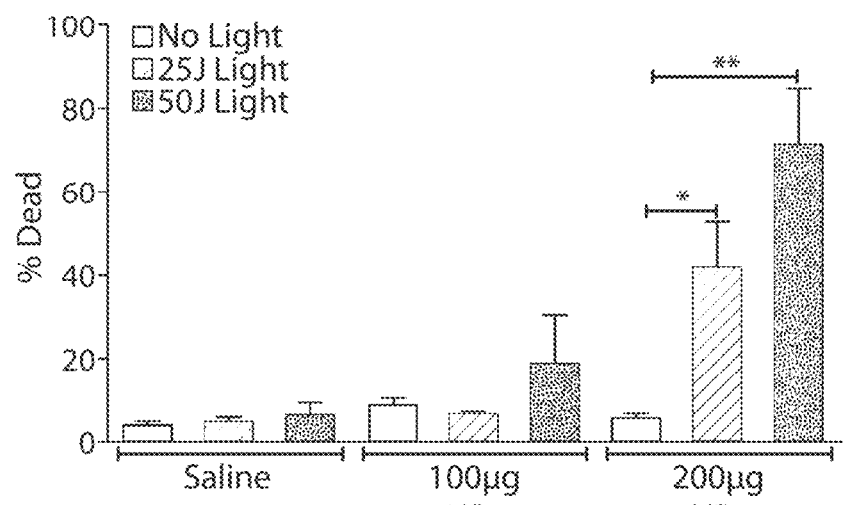
Figure 17A:
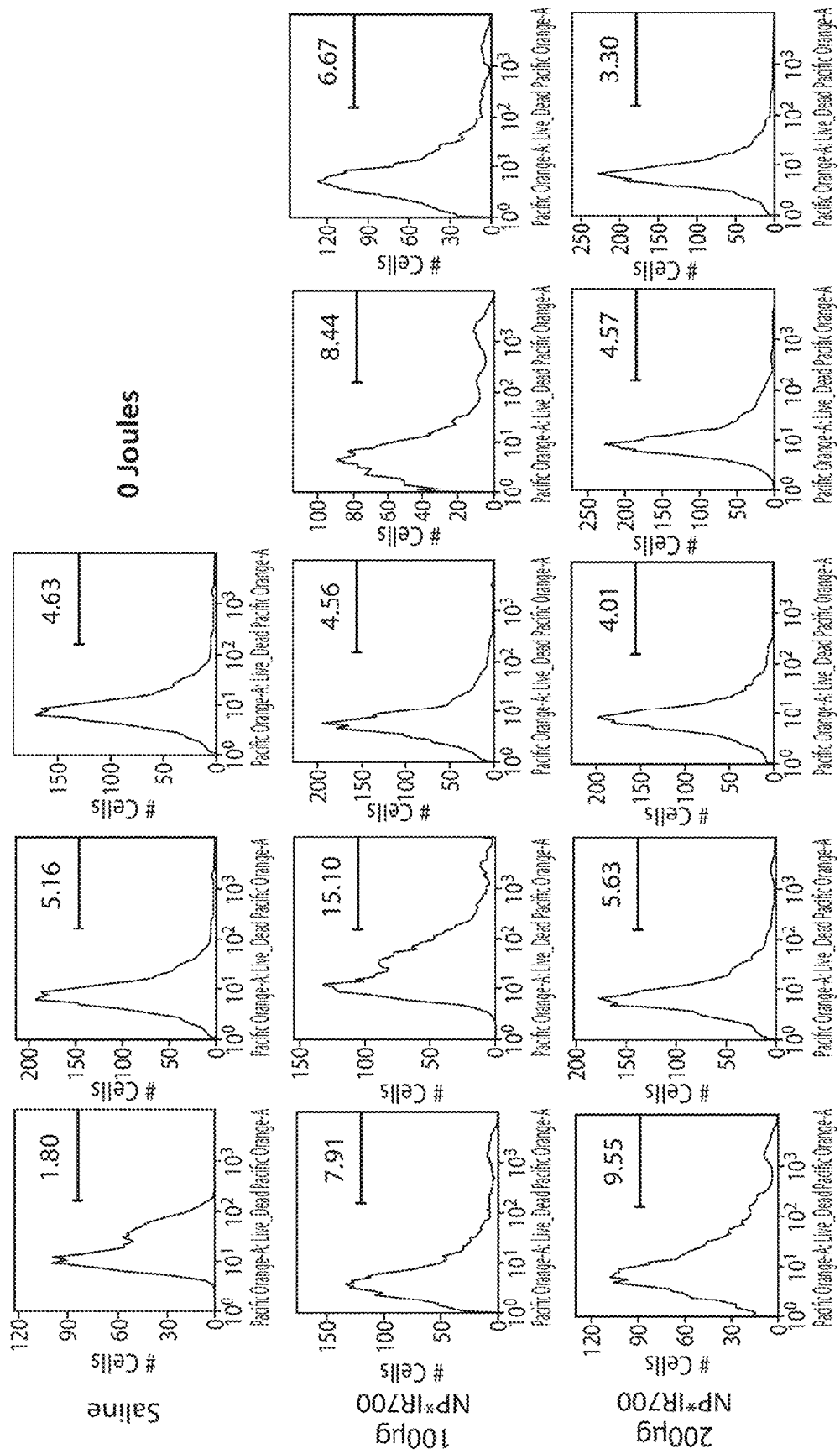
FIG. 17A-17C show raw histograms for data presented in FIGS. 16A and 16B.
Figure 17B:
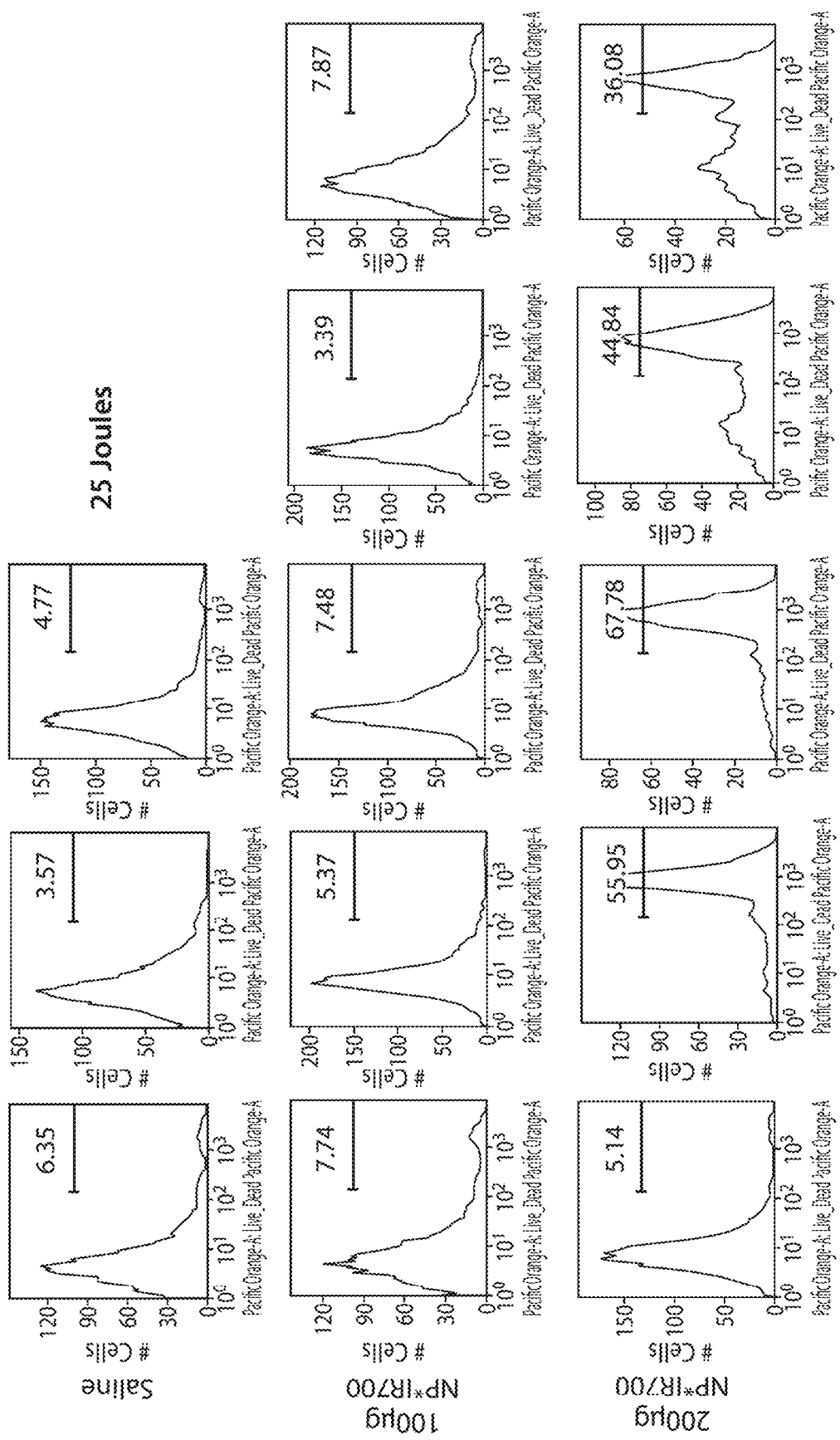
Figure 17C:
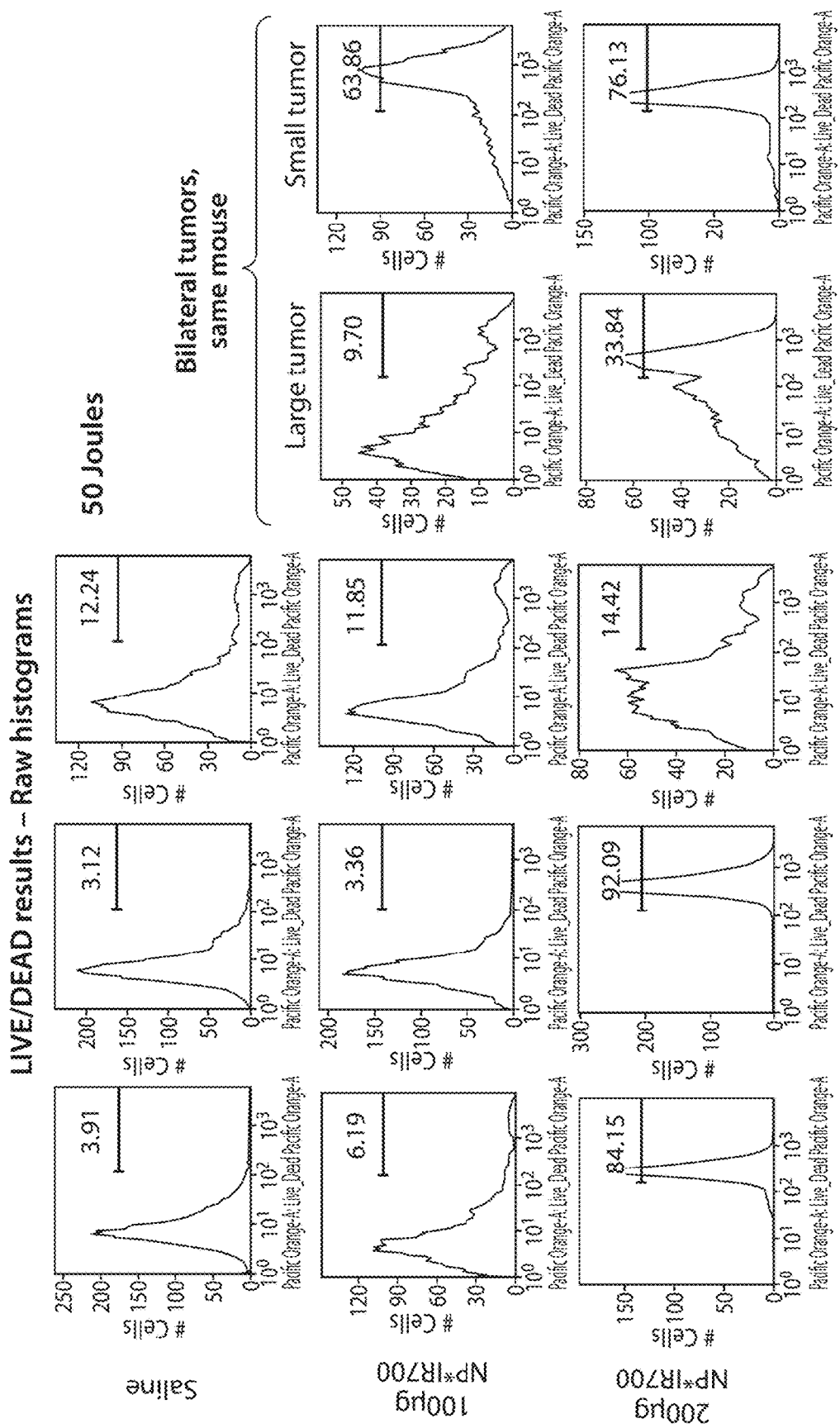

A single dose of 200 µg of IR700 (e.g., IRDye® 700DX) photosensitive viral-like nanoparticles (NPs) was capable of killing the majority of the tumor cells after treatment with 50 J of light (FIG. 16B and FIG. 17C). The level of killing with 200 µg of NPs was reduced by nearly half when the tumors were treated with 25 J of light (FIG. 16B and FIG. 17B). 100 µg of NPs was not enough to induce killing with 25 J of light (FIG. 16B and FIG. 17B); however, some tumor death was observed at 50 J dose (FIG. 16B and FIG. 17C). This study provided the necessary IR700 (e.g., IRDye® 700DX) photosensitive viral-like nanoparticles and light dosage information for in vivo studies.

Example 15—Immune System Activation Study

The TC-1 tumor model offers the ability to examine anti-tumor immune induction upon treatment with viral-like nanoparticles in immune competent animals. The TC-1 tumor line was developed from C57Bl/6 lung epithelial cells immortalized with HPV16 oncogenes E6 and E7 as well as a mutated gene expressing c-Ha-Ras (Lin K Y, et al., Cancer Research. 56(1):21-6, 1996). These cells can be implanted subcutaneously or, for studying metastatic models, they can be injected intravenously to seed cells in the lungs. For nearly twenty years these cells have been used to test E6 and E7 therapeutic vaccine efficacy. E7 has a distinctive MHC class I epitope on the C57Bl/6 background that has been shown to be protective if a CD8 T-cell response can be elicited against it (H-2D$^b$, aa 49-57 RAHYNIVTF (SEQ ID NO: 3)) (Feltkamp M C, et al. European Journal of Immunology. 23(9):2242-9, 1993). These responses are detected by both tetramer staining and re-stimulation of cells with the peptide followed by intracellular cytokine staining.

Figure 18:
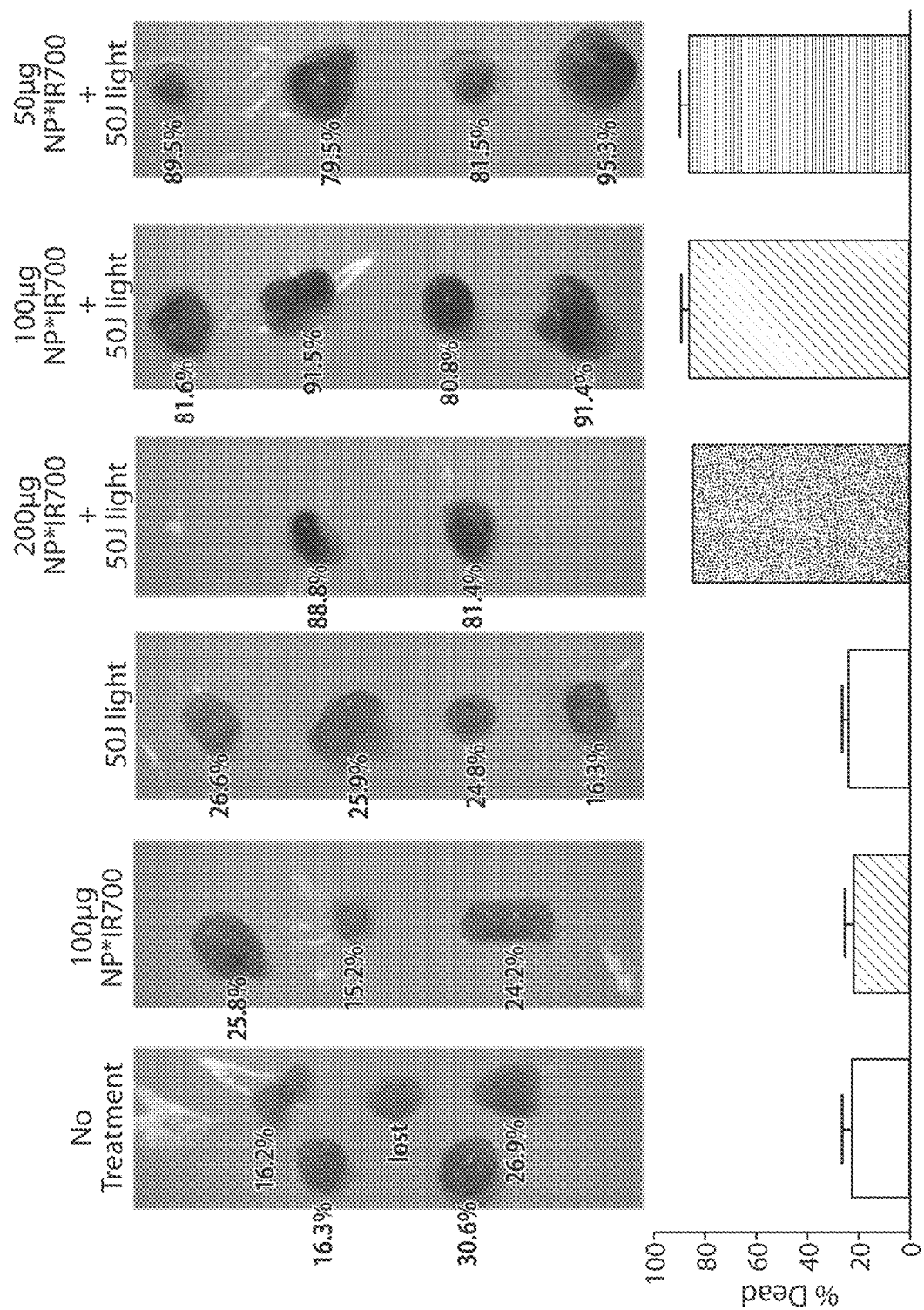
FIG. 18 (top panel) shows tissue samples obtained front animals inoculated subcutaneously with $2\times10^5$ TC-1 tumor cells in 100 µl of PBS and administered: (1) no treatment, (2) 100 µg viral-like nanoparticles (designated NPs in the figure) assembled from variant HPV16/31 L1 proteins and HPV L2 proteins, labeled with IRDye® 700DX [without light, (3) PBS with 50 J/cm$^2$ light, (4) 200 µg viral-like nanoparticles with 50 J/cm$^2$ light, (5) 100 µg viral-like nanoparticles with 50 J/cm$^2$ light and (6) 50 µg viral-like nanoparticles with 50 J/cm$^2$ light.

Does Response Study: Animals were inoculated subcutaneously with 2×10$^5$ TC-1 cells in 100 µl of PBS. Approximately two weeks after inoculating, animals were randomized into six groups: (1) no treatment controls, (2) 100 µg viral-like nanoparticles (containing a combination of variant HPV16/31 L1 proteins and HPV L2 proteins labeled with IRDye® 700DX) without light controls, (3) PBS with 50 J/cm$^2$ light controls, (4) 200 µg viral-like nanoparticles with 50 J/cm$^2$ light, (5) 100 jig n viral-like nanoparticles with 50 J/cm$^2$ light and (6) 50 µg viral-like nanoparticles with 50 J/cm$^2$ light. Mice received PBS or viral-like nanoparticles by intravenous injection of a 100 µl volume, and light was applied to the tumor 12 hours later using a 690 nm laser. Tumors were harvested 24 hours later, digested to generate a single cell suspension, and stained with a viability stain to measure the percentage of dead cells (FIG. 18, top).

Several animals in the high dose group experienced symptoms related to tumor lysis syndrome, likely due to the massive and rapid tumor necrosis and release of intracellular components into the animals' system. While none of the "100 µg nanoparticles with 50 J/cm$^2$ light" group died, mice in the group did display some signs of sickness (FIG. 18, top). The "100 µg nanoparticles without light" and the "PBS with 50 J/cm$^2$ light" groups did not display signs of sickness, indicating that the response observed was due to the combination of the viral-like nanoparticles and light. Overall, necrosis was apparent in all groups that received the viral-like nanoparticles and light. Maximal killing occurred in all groups, and no dose response was observed (FIG. 18, bottom).

Figure 19A:
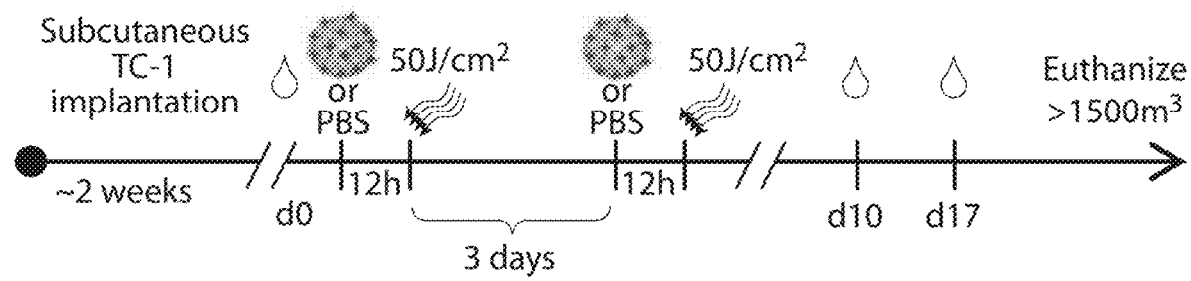
FIG. 19A shows a schematic of the experiment described in Example 15.

Survival Study: Animals were inoculated subcutaneously with 2×10$^5$ TC-1 cells in 100 µl of PBS. Approximately two to three weeks after inoculating, animals were randomized into the treatment group (25 µg viral-like nanoparticles) and the placebo group (PBS only). Mice received two rounds of treatment, three days apart. A treatment was considered a single intravenous injection of 100 µl of either 25 µg of viral-like nanoparticles or sterile PBS, followed 12 hours later by light treatment at 50 J/cm$^2$ using a 690 nm laser. Tumor volumes were measured every 3-4 days, and animals were euthanized when their tumors reached a size >1500 mm$^3$ (FIG. 19A).

Figure 19B:
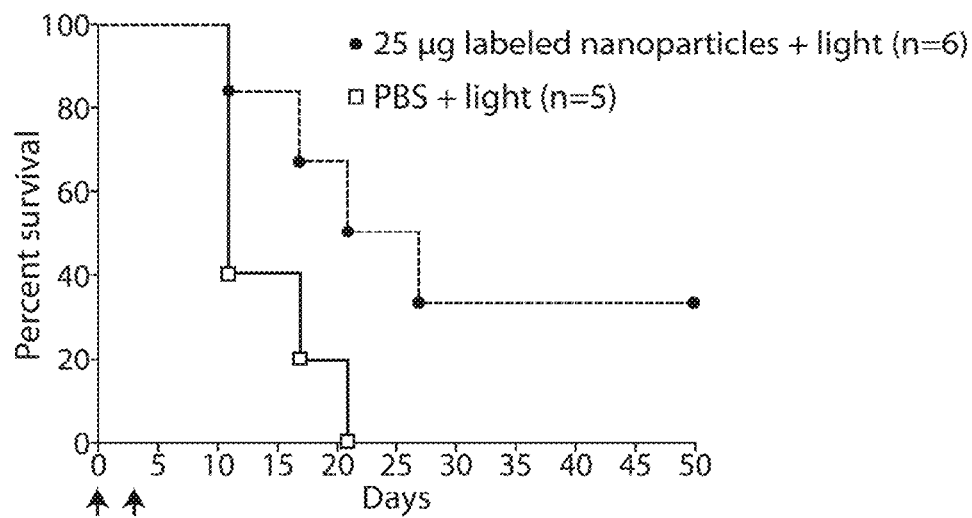
FIG. 19B shows a graph of percent survival in animals injected with viral-like nanoparticles designated nanoparticles in the figure) versus control (with fight)
Figure 19C:
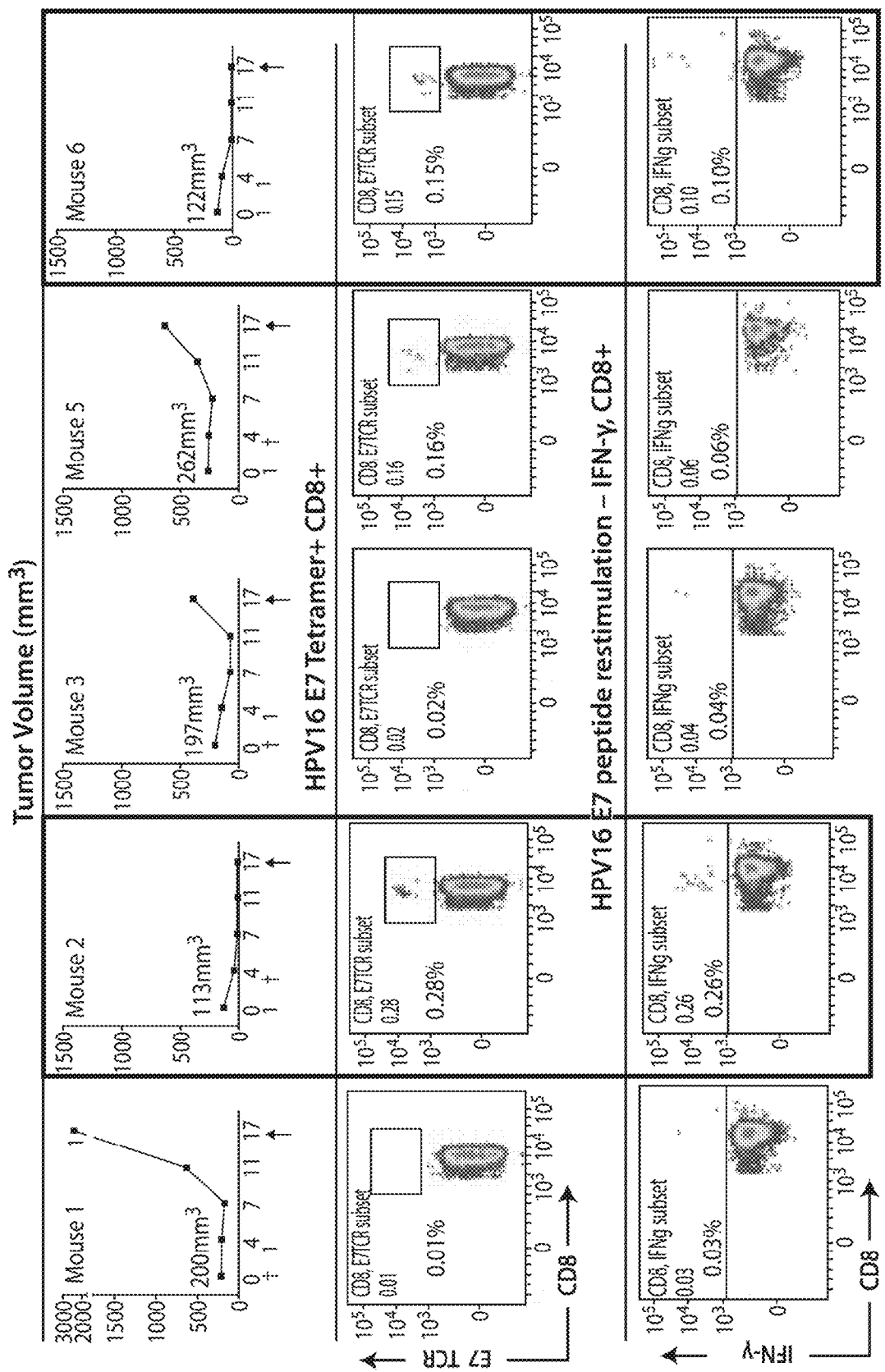
FIG. 19C shows tumor volume (top panel), "E7 tetramer$^+$ CD8$^+$ T-cells" and "TNF-gamma secreting CD8$^+$ cells" in individual mice.

Treatment with viral-like nanoparticles was able to delay growth or eradiate tumors in animals with tumors less than 500 mm$^3$ (FIGS. 19B and 19C). There was no effect on tumor growth kinetics in the placebo group. The two animals that started with the smallest tumors showed no evidence of tumors within 7 days of the first treatment, and three of the animals showed signs of tumor reduction (FIG. 19C).

Immunology Study: For the immunological readout, blood was collected on day 0 (prior to first treatment), day 10 and day 17. Red blood cells were lysed and the remaining cells were split into two, one half stained for cell surface markers (CD62L, CD127, CD103, CD69, CD4, CD8, CD3, H2-D b E7(49-57) tetramer). The other half was re-stimulated for 4.5 hours with HPV16 E7 peptide 49-57 followed by staining with antibodies against CD4, CD8 and IFN-gamma as well as a viability dye to discriminate live cells.

In the blood of the two animals with controlled tumor growth, both "E7 tetramer+CD8$^+$ T-cells" and "INF-gamma secreting CD8$^+$ cells" (after re-stimulation with E7 peptide) could be detected, indicating that a potential anti-tumor response had been elicited (FIG. 19C).

Example/6—Histological Analysis

The effects of photosensitive viral-like nanoparticles (e.g., viral-like nanoparticles containing a combination of variant HPV16/31 L1 proteins and HPV L2 proteins conjugated to IR700 dye) at the histological level were assessed using a murine xenograft model. Briefly, 1.5×10$^6$ 92.1 uveal melanoma cells were implanted into the subcutaneous space of the hind flank of nu/nu mice. The tumors were allowed to reach approximately 200 mm$^3$, at which time the animals were treated with an intravenous injection of 200 Ng of photosensitive viral-like nanoparticles. Twelve hours following the injection of photosensitive viral-like nanoparticles, the tumor site was irradiated with 50 J/cm$^2$ of 690 nm near-infrared light. After an additional 24 hours, the animals were euthanized, the tumor tissue excised, fixed in formalin, paraffin embedded and processed for standard histological examination.

The hematoxylin and eosin (H&E) images revealed a large degree of necrosis, when compared to untreated controls (images not shown). The tumor treated with photosensitive viral-like nanoparticles and laser had a pale appearance when compared to the control tumor. Upon examination at higher magnification, the cells of the photosensitive viral-like nanoparticle-treated tumors showed a dramatic loss of cytoplasm compared to the control treated tumor. Moreover, the extent of necrosis covered the entire tumor leading to the conclusion that the NIR light penetrates through the entire depth of tumor tissue.

Example 17—Viral-Like Nanoparticle Activity in an Orthotopic Xenograft Model of Uveal Melanoma The most common primary malignancy of the eye is uveal melanoma (UM). Approximately 2,000 patients present annually in the US, with more frequent occurrence in Europe. Though several treatment options exist for UM, no treatment reliably controls tumor growth, preserves vision, and minimizes the occurrence of radiation-related side effects.

Viral-like nanoparticle phototherapy (PT) is a novel molecular-targeted cancer therapy that involves a two-stage process requiring administration of both drug and light activation. The drug portion of viral-like nanoparticle PT is a photosensitive viral-like nanoparticle (NP) conjugated to IRDye®700 DX, a near-infrared (NIR) phthalocyanine dye that acts as a light sensitizer, followed by the application of non-thermal NIR light designed to treat adults with primary uveal melanoma.

In the current study the anti-cancer activity of the photosensitive viral-like nanoparticle was evaluated in an orthotopic xenograft model of uveal melanoma. In this model, human uveal melanoma cells were implanted into the choroidal space of immunosuppressed rabbits and allowed to grow. When tumors were observable by fundoscopy, the animals were assigned to treatment or control groups. In both cases, the animals were followed by fundoscopy and ultrasound for progressive tumor growth or response to treatment. Following termination of the study, the tumor-bearing eyes were also examined by gross and histopathology.

This study was carried out in using 20 total rabbits implanted with the 92.1 uveal melanoma cell line. In total, 11 of twenty animals developed tumors. Two animals died unexpectedly during the follow-up period prior to treatment; these animals were used as untreated controls. Several animals had extra-ocular tumors that were not lasered; these were used as internal controls. Animals with tumors in the anterior chamber were excluded from the study.

All treated tumors showed a major tumor response compared to control animals, demonstrated by fundoscopy, gross pathology and histopathology evaluation. Retinal tissues adjacent to tumors were not affected by the treatment.

In conclusion, based on the extent of the tumor response and necrosis seen following photosensitive viral-like nanoparticle administration and laser administration, the treatment methodology provided herein may be used for the treatment uveal melanoma tumors.

Study Schedule: Two treatment groups: 1) full tumor treatment; 2) No treatment.

TABLE 3

| | |
|---|---|
| Animals arrive | Apr. 22/23$^{rd}$, 2014 |
| Tumor cell implantation | Apr. 29/30$^{th}$, 2014 |
| Treatment start | May 20$^{th}$, May 27$^{th}$, Jun. 3$^{rd}$, 2014 |
| Study termination | Jun. 24$^{th}$, 2014 |
| Draft report | Jul. 25$^{th}$, 2014 |

Methods and Experimental Design:
Test System

TABLE 4

| | |
|---|---|
| Species: | Rabbit |
| Strain: | New Zealand Albino |
| Number and Sex | |
| Total ordered: | 20 |
| Proposed total in study: | 20 |
| Sex: | F |
| Age at Receipt: | 6 months |
| Source: | Charles River |
| Identification: | RFID and ear tag |

Model

Cell Culture

Human uveal melanoma cell line 92.1 (courtesy of Dr. Jerry Y. Niederkorn, University of Texas Southwestern Medical Center, Dallas, TX) were cultured at 37° C. in 5% $CO_2$ in complete culture medium (RPMI-1640 with 10% fetal bovine serum, 100 U/mL penicillin G. 250 ng/mL amphotericin B, and 100 µg/mL streptomycin solution).

Animals and Induction of Immunosuppression

New Zealand albino rabbits with a mean initial weight approximately 3 kg were used for this study. The rabbits were immunosuppressed with daily subcutaneous injections of cyclosporin A (CsA; Sandimmune 50 mg/mL; Novartis Pharmaceuticals, Cambridge, MA, USA). CsA administration was maintained throughout the experiment to prevent spontaneous tumor regression. The dosage schedule was 15 mg/kg per day for 3 days before cell inoculation and for 4 weeks thereafter, followed by 10 mg/kg per day until the end of the experiment. Dosage was further attenuated at the discretion of the veterinarian. CsA doses were adjusted daily according to each animal's body weight. The body weight was measured daily, and was posted in the room where the rabbits were housed.

During the follow-up, the animals were monitored daily for signs of CsA toxicity, such as gingival hypertrophy, drooling, diarrhea, and weight loss. If the animals showed early signs of CsA toxicity (e.g. loss of appetite), the vet staff was consulted immediately for supportive management, such as appetite stimulant and GI motility enhancer. Adjusting the injection dose was also considered according to the vet's recommendation.

Cell Implantation

On day 3 after CsA treatment, the animals were anesthetized with an intramuscular injection of ketamine (40 mg/kg) and xylazine (6 mg/kg). After anesthesia, 1-3 drops of 0.5% proparacaine hydrochloride were applied to the right eyes and $1.0 \times 10^6$ 92.1 human uveal melanoma cells in a volume of 100 µl suspension was injected into the suprachoroidal space of the right eye of the rabbits using a bent cannula. Briefly, a sterile drape was placed over the eye in order to avoid any contamination with hairs or eye lashes, and the conjunctiva was cleaned with 10% betadine solution. Next, the eye was rotated forward using sutures beneath the ocular muscles, and after dissecting the conjunctiva, a sclerotomy was performed approximately 10 mm from the limbus. The cannula was then inserted into the slerotomy (⅓-½ of its length) and the cells (100 µL containing $1.0 \times 10^6$ cells) were injected into the suprachoroidal space. The needle was slowly retracted, and sutures closing the sclerotomy were tightened to ensure minimal reflux at the injection site. A drop of antibiotic ophthalmic solution (erythromycin ointment) was applied over the surgical wound to prevent infection.

Housing, Feed, Water and Environmental Conditions, Acclimation

The animals were housed in group housing in groups of 6 and fed food that is fresh, palatable, and nutritionally adequate ad libitum. Water that is clean, potable, and uncontaminated was provided ad libitum. Environmental controls were set to maintain temperatures 22±4° C. (68±5° F.) with relative humidity of 50%±20%. A 12-hour light/dark cycle was maintained. The animals were acclimated for at least 5 days after arrival at the facility prior to baseline evaluation. Animals were assigned to test groups after baseline fundoscopic evaluations.

Test and Control Articles

TABLE 5

Vehicle of Test Article

| | |
|---|---|
| Identity: | PBS |
| Storage Conditions: | 4° C. for up to 3 months protected from light |
| Handling Precautions: | Standard PPE |

TABLE 6

Test Article

| | |
|---|---|
| Identity: | Nanoparticle labeled with IRDye ® 700 DX |
| Storage Conditions: | 4° C. for up to 2 months protected from light |
| Handling Precautions: | Standard PPE |

TABLE 7

Laser

| | |
|---|---|
| Power Setting: | 600 mW |
| Duration: | 83 s |
| Fluence: | 50 J/cm$^2$ |
| Spot size: | 5.0 mm |
| Wavelength: | 690 nm |

Preparation of Dose Formulations

The test article was diluted 1:1 in sterile water for injection.

Administration of Test/Control Articles

Dosing: Photosensitive viral-like nanoparticle or saline was administered by intraocular injection in the vitreous.

Laser administration: Laser treatment was applied using a slit lamp system with a Coherent Opal Photoactivator® laser delivering 690 nm light at a power of 600 mW over a duration of 83 seconds for a total fluence of 50 J/cm$^2$. The laser spot size was set to a diameter of 5 mm and as such, tumors that were greater than this size were lasered with overlapping spots. In cases where a clear distinction of the tumor border could not be delineated due to ocular complications (e.g., vitritis, retinal detachment) the entire suspicious area was lasered.

Mortality/Morbidity Checks: All animals remained in good health throughout the study, aside from the two animals that died due to CsA complications (see below).

Clinical Observations: All animals were observed daily by animal facility personnel; observations were recorded. Most animals experienced some degree of weight loss and loss of appetite, which was attributed to the CsA.

Ophthalmology

Frequency: Ophthalmic examination by fundoscopy and ultrasound was performed weekly.

Procedure: The animal was sedated and their right eye was dilated using ocular phenylephrine hydrochloride and tropicamide drops. Next, a fundoscopic examination of the eye was performed using an indirect binocular ophthalmoscope. The ophthalmologist recorded any ocular complications. When a tumor was identified, the size was estimated by comparing it to the optic disc (disc diameter [DD]; 1 DD=approximately 1.75 mm). For the ultrasound readings, immediately following fundus exam, an ultrasound probe was applied to the eye to visualize the location of the tumor as determined by fundus exam. Ultrasound measurements proved technically difficult, primarily because some of the tumors were located too peripherally to be properly visualized. As a result, it was not always possible to measure the largest tumor dimension; and in most cases only the height in was quantifiable.

Terminal Procedures and Anatomic Pathology

Unscheduled Deaths: Of the 20 animals used in this study, one was euthanized due to weight loss (>20% of weight upon arrival), as per the protocol guidelines. One animal died unexpectedly due to gastrointestinal stasis caused by CsA toxicity.

Scheduled Euthanasia: Upon the termination of the study, animals were euthanized in accordance with accepted American Veterinary Medical Association (AVMA) guidelines. The animals were exsanguinated with anesthesia using a combination of ketamine-xylazine-acepromazine (0.75 mg/kg, 5 mg/kg, and 20-35 mg/kg, respectively) and buprenorphine (0.2 mg/kg).

Results

Overall, 11 animals developed histopathologically evident tumors. As previously mentioned, two animals that died unexpectedly and were used as the untreated control. 9 animals with different tumor sizes received treatment with photosensitive viral-like nanoparticles. One animal was not included in the evaluation due to the extent of tumor in the anterior segment of the equator that could not be lasered.

For animals that had tumors in the back of the eye and received full treatment (photosensitive viral-like nanoparticle+laser) a noticeable tumor response was observed, which was characterized by three elements: 1) induction of extensive tumor necrosis; 2) change in the growth pattern, from diffuse to a "sleeve-like pattern"; and 3) sparing of the adjacent retina.

TABLE 8

| Animal number & tumor location and size | Fundoscopy and/or ultrasound: presence of tumor before treatment | Fundoscopy and/or ultrasound: tumor evaluation after treatment | Gross & histopathology |
|---|---|---|---|
| 3-Large tumor posterior to the equator | + | Tumor growth arrest | Intraocular tumor with overall necrotic consistency on gross pathology >50% necrosis by histopathology No damage to adjacent retina |
| 6-Large tumor posterior to the equator | + | Tumor growth arrest | Intraocular tumor disaggregated on gross pathology evaluation >70% necrosis by histopathology No damage to adjacent retina |
| 7-Medium size tumor posterior to the equator | + | Complete response | Non-pigmented tumor on gross pathology No tumor found on histopathology-suspicious area ~8.2 mm in length suspected to correspond to tumor location |

TABLE 8-continued

| Animal number & tumor location and size | Fundoscopy and/or ultrasound: presence of tumor before treatment | Fundoscopy and/or ultrasound: tumor evaluation after treatment | Gross & histopathology |
|---|---|---|---|
| 9-Small tumor posterior to the equator | + | Complete response | No tumor on gross pathology Complete response on histopathology; no damage to adjacent retina |
| 10-Medium sized tumor posterior to the equator | + | Tumor shrinkage | Non-pigmented tumor located at the equator on gross pathology ~70% necrosis on gross pathology |
| 11-Small tumor posterior to the equator | + | Complete response | No tumor on gross or histopathology |
| 15-Large tumor posterior to the equator | + | Complete response of treated nodule Partial necrosis in peripheral tumor | Non-pigmented tumor on gross pathology located at the periphery and additional adjacent tumor nodule on the posterior of the eye Histopathology revealed no tumor where the treated nodule was present. Other areas that were too peripheral were difficult to have full access with the laser and show some extent of necrosis at the apex of the tumor |
| 16-Tumor posterior to the equator | + | Complete response | Non-pigmented nodule identified on gross pathology No tumor on histopathology; scar (fibrosis and inflammation) measuring ~1.5 mm in the area where the tumor is believed to have been located |
| 19-Large tumor posterior to the equator | + | Tumor growth arrest | Large tumor on gross pathology with disaggregated/necrotic appearance Massive necrosis, sleeve-like pattern |

Untreated Controls

Rabbit #14 was euthanized on week 4 due to unacceptable weight loss (>20% of initial body weight). Fundus examination for the presence of tumor was inconclusive due to massive hemorrhage and retinal detachment. This animal received no treatment.

Ultrasound: This rabbit did not undergo an ultrasound examination due to the timing of death.

Gross/histopathology: On gross pathology, an intraocular tumor measuring 3 mm in height (H)×8 mm in the largest tumor dimension (LTD), and on histopathology an intraocular tumor measuring 2.2 mm H and 9.5 in largest tumor dimension, was noted. On gross pathology, an extraocular tumor measuring 1.4 mm in height and 9.4 mm in largest tumor dimension were noted. Approximately 10% of both the intra- and extraocular tumors were necrotic. No sleeve pattern was detected.

Full Treatment

Rabbit 9

Rabbit #9 had a clinically detectable tumor on fundus approximately 1 DD in size on week 4, which was treated immediately. The following week, the tumor was estimated as 0.5 DD. On week 6, the tumor was estimated at <0.5 DD and on the final week it was not detected.

Ultrasound: Ultrasound did not discern a tumor on week 3, but on weight 4 a mass measuring 1.04 mm in height was identified. On subsequent weeks, the measurements on ultrasound regressed until it was no longer visible by week 6 and thereafter.

Gross/Histopathology: Histopathology revealed no tumor or cells. However, serial sections of the entire eye and immunohistochemical results are pending to further confirm this result.

Rabbit 6

There was a clinical suspicion of a tumor on week 4 (elevated mass beneath the retina), but subretinal hemorrhage, fluid, and retinal detachment precluded clinical size estimation for the duration of the experiment.

Ultrasound: By ultrasound, on week 3 a large 4.88 mm mass was detected, which grew to 5.29 mm on week 4, at which point we commenced treatment. On week 5, the tumor measured 4.88 mm, while on weeks 6 and 7 the tumor measured 4.02 and 4.98 mm, respectively.

Gross/histopathology: On gross pathology, two distinct tumors were identified: an intraocular tumor and a conjunctival tumor, the latter suspected to be a result of reflux during cell implantation. Owing to the location of the conjunctival tumor, it was not treated, and thus we consider it as an internal control. The intraocular tumor was disaggregated and measured 7 mm H×11 mm LTD. An extraocular extension measuring 6 mm H×9 LTD mm was also identified, which had a characteristic texture. On histopathology, the intraocular tumor measured 4.9 mm H×8.3 LTD mm and was >70% necrotic, with most of the remaining viable cells forming the aforementioned sleeve-like pattern. The untreated conjunctival tumor exhibited far less necrosis (~15%) and the sleeve pattern was not evident.

The goal of this study was to explore the activity of photosensitive viral-like nanoparticles+NIR light in an orthotopic xenograft model of uveal melanoma in the rabbit eye. All tumors that received photosensitive viral-like nanoparticles+laser treatment responded favorably to the treatment. This is particularly evident for small to medium tumors that had evident tumor shrinkage as a response of treatment and complete histopathological responses. In rabbit 9, for example, that presented with a small tumor at week 4, the tumor was completely eradicated by the first two doses of the treatment and was no longer detectable either clinically or histopathologically two weeks after the second treatment. In bigger tumors, for example rabbit 4, most of the tumor was necrotic, this is in stark contrast to the untreated control (rabbit 14), which only exhibited necrosis in approximately 10% of the tumor volume, a clear indication of the efficacy of the treatment. Moreover, several animals that had intraocular tumors that received full treatment had extraocular extensions that were not lasered; these fractions showed substantially less necrosis than treated tumor fractions, which is further evidence supporting the efficacy of laser activated photosensitive viral-like nanoparticles for the treatment of uvea melanoma. Retinal areas adjacent to tumors were not affected by the treatment.

Based on the intraocular tumor response following treatment, especially compared to the controls (untreated, extraocular fractions), the data provided herein support a selective and potent anti-cancer activity for photosensitive viral-like nanoparticles, in the presence of a tumor, for the treatment of ocular melanoma.

Example 18—In Vitro Potency Assay Comparing HPVL1 vs BPV L1

Photosensitive viral-like nanoparticles (e.g., viral-like nanoparticles containing a combination of variant HPV16/31 L1 proteins and HPV L2 proteins conjugated to IR700 dye) potency was assayed by an in vitro cell killing assay. Uveal melanoma cells (e.g., cell line OCM-1 or 92.1) were harvested by routine methods using a solution of EDTA and trypsin. Once removed from the tissue culture plastic, the cells were suspended in complete growth media and were allowed to recover for approximately 30 minutes at 37° C. During this recovery period, serial dilutions of the photosensitive viral-like nanoparticle were made in approximately ½ log increments (2000 pM, 600 pM, 200 pM, 60 pM, 20 pM, 6 pM, 2 pM and 0.6 pM) in PBS+2% fetal bovine serum. Following the recovery period, the cells were counted, centrifuged and suspended in PBS+2% FBS to a cell density of $3\times10^6$/ml. An equal volume of cell suspension was added to the viral-like nanoparticle dilutions to yield $1.5\times10^6$ cells per ml in the appropriate concentration (1000 pM, 300 pM, 100 pM, 30 pM, 10 pM, 3 pM, 1 pM and 0.3 pM) of viral-like nanoparticle. These conditions (e.g., 360 µl) were incubated on ice for about 1.5 to 2 hours.

Following this incubation, the tubes were centrifuged to collect the cells and the cells were subsequently washed twice with PBS+2% FBS, without the photosensitive viral-like nanoparticles. After the final centrifugation, the cells were suspended in 200 µl of PBS+2% FBS. A 100 µl of each sample is removed and transferred to the well of a 96-well, ½ area plate. Each sample was then irradiated with 25 J/cm² (600 mW, 43 seconds) of near infrared light (689 nm) using a Coherent Opal Photoactivator ophthalmic laser. Following the irradiation, the sample of cells was then transferred to a new tube. Both the light irradiated and non-irradiated samples were placed at 37° C. for an additional 1 to 2 hours.

Figure 20:
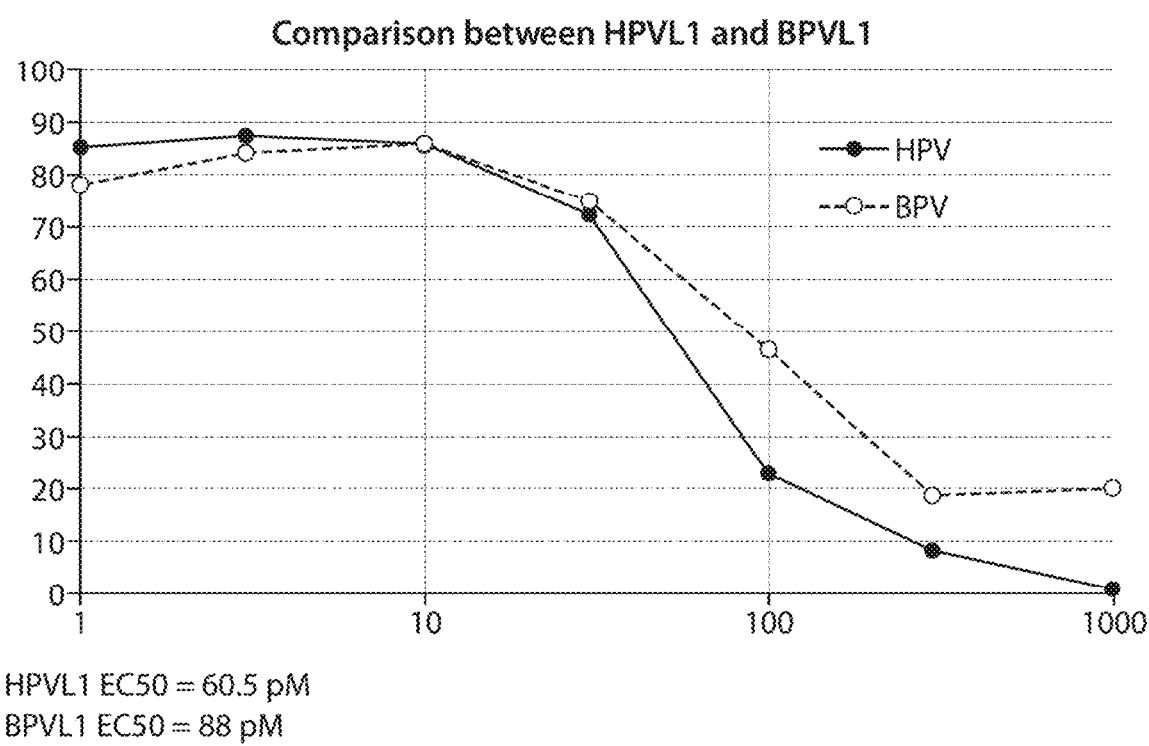
FIG. 20 shows a graph of results from a potency assay, comparing the effects of photosensitive BPV viral-like nanoparticles and photosensitive HPV viral-like nanoparticles on cell viability.

Following this incubation a final 20 µl sample of cells were mixed 1:1 with AOPI stain (Acridine Orange and Propidium Iodide) and the viability of the cells was evaluated using a Nexcelom Cellometer Auto 2000. FIG. 20 shows comparable effects of BPVL1 and HPVL1 on cell viability at half maximal effective concentration (EC50) (BPVL1=88 pm; HPVL1=60.5 pm), indicating that the potencies of the photosensitive molecules are comparable to each other.

Figure 21:
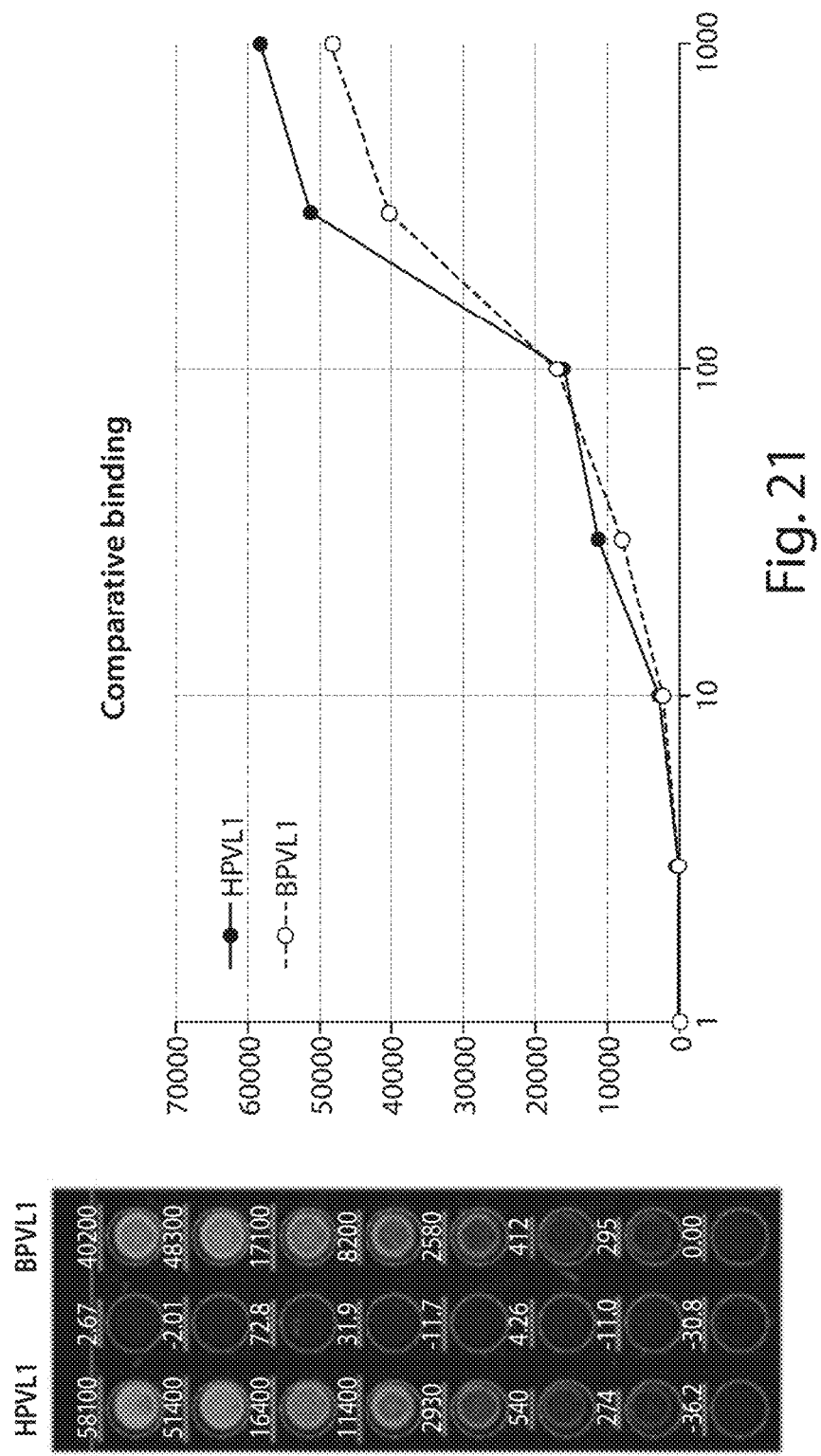
FIG. 21 shows a graph of results form a binding assay, comparing binding of photosensitive BPV viral-like nanoparticles and photosensitive HPV viral-like nanoparticles to cells.

FIG. 21 shows a sample of cells from the killing assay described in FIG. 20 analyzed for photosensitive viral-like nanoparticle binding. Cells from the killing assay were scanned on an Odyssey Clx gel/plate scanner. The Odyssey Clx is specifically designed for the detection and quantitation of a series of infrared dyes, including, IR700 dye (e.g., IRDye® 700DX). Thus, in this assay, the cells that were treated with different concentrations of the photosensitive viral-like nanoparticles show a concentration dependent amount of fluorescence associated with the cells, indicating that the cells bound both BPV-L1-IR700 and HPV-L1-IR700.

Example 19—Activity of Photosensitive Viral-Like Nanoparticles in a Xenograft Model of Head and Neck Cancer Head & Neck cancer cells were implanted in the dorsal lateral flank of nu/nu mice. Tumors were allowed to grow for two weeks. Once the tumor reached an average size of 150 mm³, the animals were randomized into 6 study groups (7 animals per group), as follows: Saline; photosensitive viral-like nanoparticles (HPV16/31 L1/L2; 200 µg dose); Saline+NIR light (50 J/cm²); photosensitive viral-like nanoparticles (200 µg dose)+NIR light (50 J/cm²); photosensitive viral-like nanoparticles (100 µg dose)+NIR light (50 J/cm²); and photosensitive viral-like nanoparticles (50 µg dose)+NIR light (50 J/cm²). Dosing and NIR light treatment was performed every three days. Tumor measurements were recorded every 3-5 days.

Figure 22:
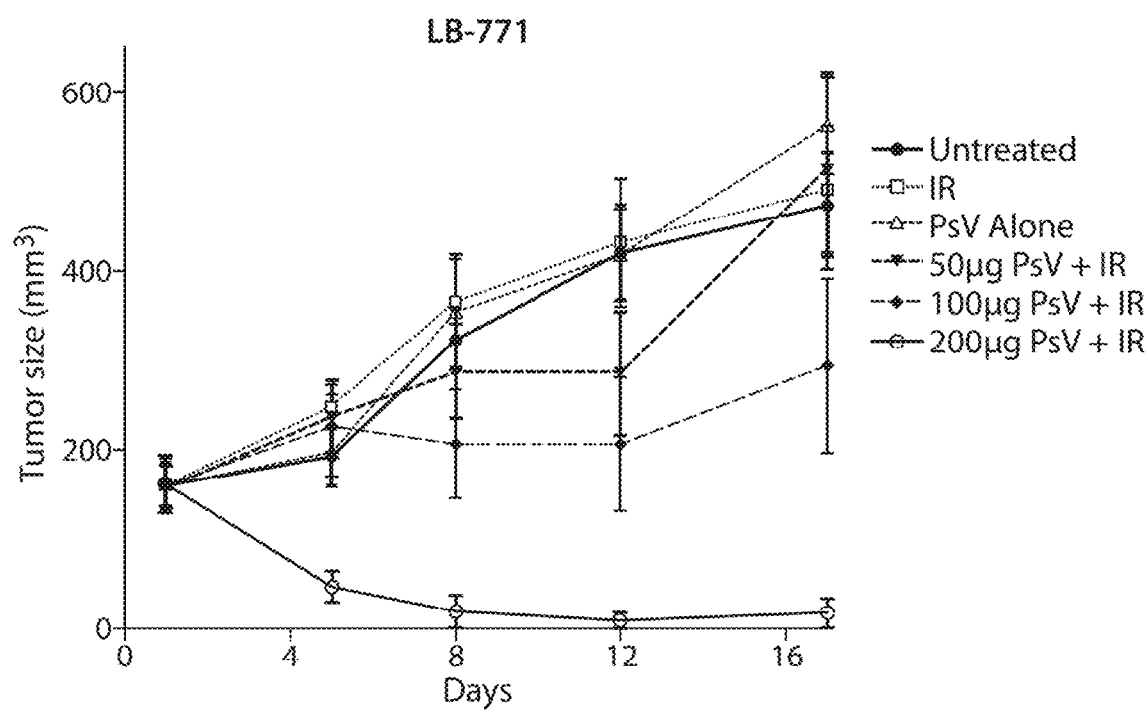
FIG. 22 shows a graph Or tumor growth curve of head and neck cancer cells following treatment with photosensitive viral like nanoparticles (designated PsV in the figure).

While all the controls showed no substantial effect for their respective treatments, there was a significant tumor growth inhibition observed in all of the dose groups (FIG. 22). The observed tumor growth inhibition was dose dependent. There was a response of the tumors in the high dose group. Two animals died in the 200 µg treatment group associated with massive cell death and potentially Tumor Lysis Syndrome related toxicities.

Example 20—Production of Photosensitive Viral-Like Nanoparticles

To produce photosensitive viral-like nanoparticles of the present disclosure, HEK293F were grown in suspension culture and were transiently transfected with a hi-cistronic plasmid DNA encoding L1 (or L1 and L2) capsid proteins. This induces the formation of proto-capsids (as described in Buck et. al. Current Protocols in Cell Biology 26.1.1-26.1.19, December 2007). Following cell mass recovery and disruption, the proto-capsids went through benzonase treatment to eliminate the host DNA contaminants and a subsequent maturation process in vitro to form viral-like nanoparticles stable for conjugation. Following purification, the viral-like nanoparticles were chemically conjugated with IR700 NHS ester to produce the photosensitive viral-like nanoparticles. FIG. 23 shows a schematic representation of an a production process.

Photosensitive viral-like nanoparticles produced from the process described in this Example have been characterized using SDS-PAGE, SE-HPLC and DLS and show purities of 90-95%. Histones from the HEK293 cells are present as part of the viral-like nanoparticle composition and comprise of 10-15% of the total protein of the viral-like nanoparticle.

What is claimed is:

1. A method comprising:
   administering to a subject a virus-like particle (VLP) comprising viral capsid proteins and about 50 to about 1000 photosensitizer molecules, wherein the subject has cancerous cells; and
   applying to the cancerous cells an infrared, near-infrared, or ultraviolet light that activates cytotoxicity of the photosensitizer molecules.

2. The method of claim 1, wherein the photosensitizer molecules comprise dye molecules that are activated by infrared, near-infrared, or ultraviolet light.

3. The method of claim 1, wherein the photosensitizer molecules are conjugated to the viral capsid proteins.

4. The method of claim 3, wherein the photosensitizer molecules are covalently conjugated to lysine residues in the viral capsid proteins.

5. The method of claim 4, wherein the photosensitizer molecules are covalently conjugated to lysine residues in the viral capsid proteins through an amide bond.

6. The method of claim 1, wherein the VLP comprises about 100 to about 1000 photosensitizer molecules.

7. The method of claim 1, wherein the VLP comprises about 50 to about 500 photosensitizer molecules.

8. The method of claim 1, wherein the VLP comprises about 100, about 200, or about 300 photosensitizer molecules.

9. The method of claim 1, wherein cytotoxicity of the photosensitizer molecules is activated by infrared light.

10. The method of claim 1, wherein cytotoxicity of the photosensitizer molecules is activated by near-infrared light.

11. The method of claim 1, wherein cytotoxicity of the photosensitizer molecules is activated by ultraviolet light.

12. The method of claim 1, wherein the VLP has a diameter of 20 to 60 nm.

13. The method of claim 1, wherein the administering comprises injecting the VLP into the subject.

14. The method of claim 1, wherein the cancerous cells form a tumor, and the administering comprises injecting the VLP into the tumor.

15. The method of claim 1, wherein the cancerous cells are in an eye, lung, pleura, liver, pancreas, stomach, esophagus, colon, breast, ovary, prostate, brain, meninges, testis, kidney, bladder, head, neck, cervix, larynx, or skin of the subject.

16. The method of claim 1, wherein the applying is 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, or 3 days after the administering.

17. The method of claim 1, wherein the applying is for about 5 seconds to about 5 minutes.

18. A method comprising:
   injecting into a tumor of a subject a virus-like particle (VLP) comprising viral capsid proteins and about 100 to about 500 photosensitizer molecules, wherein the photosensitizer molecules are conjugated to the viral capsid proteins; and
   applying to the tumor an infrared, near-infrared, or ultraviolet light that activates cytotoxicity of the photosensitizer molecules.

19. The method of claim 18, wherein the infrared, near-infrared, or ultraviolet light has a wavelength of about 700 nm.

20. The method of claim 18, wherein the infrared, near-infrared, or ultraviolet light has a wavelength of about 800 nm.

21. The method of claim 18, wherein the photosensitizer molecules are covalently conjugated to lysine residues in the viral capsid proteins through an amide bond.

22. The method of claim 18, wherein the tumor is in an eye, lung, pleura, liver, pancreas, stomach, esophagus, colon, breast, ovary, prostate, brain, meninges, testis, kidney, bladder, head, neck, cervix, larynx, or skin of the subject.

23. A method comprising:
   administering to a subject a virus-like particle (VLP) comprising viral capsid proteins and about 100 to about 500 photosensitizer molecules, wherein the photosensitizer molecules are conjugated to the viral capsid proteins; and
   exposing the VLP to an infrared or near-infrared light that activates cytotoxicity of the photosensitizer molecules.

24. The method of claim 23, wherein the infrared or near-infrared light has a wavelength of about 700 nm.

25. The method of claim 23, wherein the infrared or near-infrared light has a wavelength of about 800 nm.

26. The method of claim 23, wherein the photosensitizer molecules are covalently conjugated to lysine residues in the viral capsid proteins through an amide bond.

27. The method of claim 23, wherein the subject has cancerous cells.

28. The method of claim 23, wherein the subject has a tumor.

* * * * *

SEQUENCE LISTING

<160> NUMBER OF SEQ ID NOS: 3

<210> SEQ ID NO 1
<211> LENGTH: 1518
<212> TYPE: DNA
<213> ORGANISM: Artificial Sequence
<220> FEATURE:
<223> OTHER INFORMATION: Synthetic Polynucleotide

```
<400> SEQUENCE: 1
atgagcctgt ggctgcccag cgaggccacc gtgtacctgc ccccgtgcc cgtgagcaag      60 gtggtgagca ccgacgagta cgtggccagg accaacatct actaccacgc cggcaccagc     120
aggctgctgg ccgtgggcca cccctacttc cccatcaaga agcccaacaa caacaagatc     180
ctggtgccca aggtgagcgg cctgcagtac agggtgttca ggatccacct gcccgacccc     240
aacaagttcg gcttccccga caccagcttc tacaaccccg acacccagag gctggtgtgg     300
gcctgcgtgg gcgtggaggt gggcaggggc cagcccctgg gcgtgggcat cagcggccac     360 ccctgctga caagctgga cgacaccgag aacgccagcg cctacgccgc caacgccggc      420
gtggacaaca gggagtgcat cagcatggac tacaagcaga cccagctgtg cctgatcggc     480
tgcaagcccc ccatcggcga gcactgggc aagggcagcc cctgcaccaa cgtggccgtg     540
aaccccggcg actgccccc cctggagctg atcaacaccg tgatccagga cggcgacatg     600
gtggacaccg gcttcggcgc catggacttc accaccctgc aggccaacaa gagcgaggtg     660
cccctggaca tctgcaccag catctgcaag taccccgact acatcaagat ggtgagcgag     720
ccctacggcg acagcctgtt cttctacctg aggagggagc agatgttcgt gaggcacctg     780
ttcaacaggg ccggcgccgt gggcgagaac gtgcccaccg acctgtacat caagggcagc     840
ggcagcaccg ccaccctggc caacagcaac tacttcccca cccccagcgg cagcatggtg     900
accagcgacg cccagatctt caacaagccc tactggctgc agagggccca gggccacaac     960
aacggcatct gctggggcaa ccagctgttc gtgaccgtgg tggacaccac caggagcacc    1020
aacatgagcc tgtgcgccgc catcagcacc agcgagacca cctacaagaa caccaacttc    1080
aaggagtacc tgaggcacgg cgaggagtac gacctgcagt tcatcttcca gctgtgcaag    1140
atcaccctga ccgccgacgt gatgacctac atccacagca tgaacagcac catcctggag    1200
gactggaact tcggcctgca gccccccccc ggcggcaccc tggaggacac ctacaggttc    1260
gtgaccagcc aggccatcgc ctgccagaag cacacccccc ccgcccccaa ggaggacccc    1320
ctgaagaagt acaccttctg ggaggtgaac ctgaaggaga agttcagcgc cgacctggac    1380
cagttccccc tgggcaggaa gttcctgctg caggccggcc tgaaggccaa gcccaagttc    1440
accctgggca agaggaaggc cacccccacc accagcagca ccagcaccac cgccaagagg    1500
aagaagagga agctgtga                                                 1518

<210> SEQ ID NO 2
<211> LENGTH: 1488
<212> TYPE: DNA
<213> ORGANISM: Artificial Sequence
<220> FEATURE:
<223> OTHER INFORMATION: Synthetic Polynucleotide

<400> SEQUENCE: 2
atggccctct ggcagcaggg gcagaaactc tacctgccac ccacacccgt gtcaaaagtc      60
ctgtgttccg agacatacgt ccagcggaag tcaatcttct accacgccga gaccgaaagg     120
ctcctcacca tcggccaccc ctactacccc gtcagcattg cgctaagac cgtgcccaaa      180 gtctccgcca accaataccg cgtgttcaag atccagctgc cgacccaaa ccagttcgcc      240 ctgcccgatc gcaccgtgca taacccctcc aaggaaagac tcgtctgggc cgtgatcggc     300
gtccaagtct cacgggggcca accctgggc ggcaccgtga ccggcatcc aaccttcaac     360 gccctcctgg acgccgagaa cgtcaaccgg aaagtcacaa cacaaaccac cgacgatcgc     420
```

```
aagcagaccg ggctggacgc caaacagcag caaatcctcc tcctggggtg cacacccgct    480
gagggcgagt actggaccac cgctcggccc tgcgtgaccg acaggctgga gaacggggct    540
tgtccccccc tggagctgaa gaataagcat atcgaggacg gcgacatgat ggagatcggc    600
ttcggcgccg ctaacttcaa ggagatcaac gcctccaaga gcgacctgcc cctggatatc    660
cagaacgaaa tttgtctcta tcccgattat ctgaagatgg ccgaagatgc cgccggcaac    720
tcaatgtttt tcttcgcccg caaggagcaa gtctacgtgc ggcatatttg gacacggggc    780
gggagcgaaa aggaggctcc cacaaccgac ttctacctga aaaacaacaa gggcgacgct    840
acactgaaga tcccatccgt ccacttcggc tccccatccg ggagcctcgt cagcaccgac    900
aaccagatct tcaacagacc atattggctg tttagggctc aagggatgaa taacggcatc    960
gcttggaaca acctgctctt cctgaccgtc ggcgataaca ccaggggcac caacctgaca   1020
atctccgtgg ctagcgacgg cacacccctg accgaatacg actcaagcaa gtttaacgtg   1080
tatcaccggc acatggagga gtacaaactg gctttcatcc tggaactgtg tagcgtcgag   1140
attaccgccc agaccgtcag ccacctccag ggcctgatgc caagcgtcct ggagaactgg   1200
gagatcggcg tccaaccacc aacaagcagc atcctggaag atacatacag atacatcgaa   1260
agccccgcca ccagtgcgc ctcaaacgtg atccccgcca aggaggatcc ctacgccggc   1320
ttcaaattct ggaatatcga cctgaaggag aaactgagcc tcgatctgga ccagttccca   1380
ctcggccggc ggttcctggc ccaacagggc gctggctgca gcaccgtccg gaagaggcgg   1440
atctcacaaa agaccagttc caaacccgcc aagaagaaga agaagtag               1488
```

```
<210> SEQ ID NO 3
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 3

Arg Ala His Tyr Asn Ile Val Thr Phe
1               5
```